(12) United States Patent
Berg et al.

(10) Patent No.: US 7,087,088 B2
(45) Date of Patent: Aug. 8, 2006

(54) METHODS AND APPARATUS FOR REGULATING THE FLOW OF MATTER THROUGH BODY TUBING

(75) Inventors: Todd A. Berg, Plymouth, MN (US); James Berg, White Bear Lake, MN (US)

(73) Assignee: Torax Medical, Inc., Stillwater, MN (US)

( * ) Notice: Subject to any disclaimer, the term of this patent is extended or adjusted under 35 U.S.C. 154(b) by 297 days.

(21) Appl. No.: 10/134,306

(22) Filed: Apr. 26, 2002

(65) Prior Publication Data

US 2003/0018377 A1 Jan. 23, 2003

Related U.S. Application Data

(60) Provisional application No. 60/350,394, filed on Jan. 22, 2002, provisional application No. 60/293,345, filed on May 24, 2001.

(51) Int. Cl.
*A61F 2/04* (2006.01)
*A61F 2/06* (2006.01)

(52) U.S. Cl. ................... 623/23.64; 623/1.15

(58) Field of Classification Search ............ 623/23.64, 623/23.65–23.7, 1.26, 1.24, 1.19; 600/37, 600/29, 30; 680/32
See application file for complete search history.

(56) References Cited

U.S. PATENT DOCUMENTS

| 4,271,827 | A | 6/1981 | Angelchik | 128/1 R |
|---|---|---|---|---|
| 5,234,447 | A | 8/1993 | Kaster et al. | 606/153 |
| 5,234,448 | A | 8/1993 | Wholey et al. | 606/153 |
| 5,387,235 | A | 2/1995 | Chuter | 623/1 |
| 5,397,355 | A * | 3/1995 | Marin et al. | 623/1.2 |
| 5,411,552 | A | 5/1995 | Andersen et al. | |
| 5,695,504 | A | 12/1997 | Gifford, III et al. | 606/153 |
| 5,827,321 | A * | 10/1998 | Roubin et al. | 623/1.16 |
| 5,843,164 | A | 12/1998 | Frantzen et al. | 623/1 |
| 5,861,036 | A | 1/1999 | Godin | |
| 5,876,448 | A | 3/1999 | Thompson et al. | 623/12 |
| 5,957,949 | A | 9/1999 | Leonhardt et al. | 606/194 |
| 6,015,431 | A * | 1/2000 | Thornton et al. | 623/1.14 |
| 6,019,789 | A | 2/2000 | Dinh et al. | |
| 6,056,744 | A | 5/2000 | Edwards | 606/41 |
| 6,106,548 | A | 8/2000 | Roubin et al. | |

(Continued)

FOREIGN PATENT DOCUMENTS

WO    WO 00/59398    10/2000

*Primary Examiner*—Alvin J. Stewart
(74) *Attorney, Agent, or Firm*—Fish & Neave IP Group Ropes & Gray LLP; Robert R. Jackson; Hong S. Lin

(57) ABSTRACT

A self-retracting body, which may have a bore, may be inserted into a biological passage. A dilating balloon may be used to expand the body toward an inner wall of the passage. The body may include an anchor that may engage the wall. The anchor may include a tip that is within the body before the body expands and extends away from the body during expansion. The body may include an opening that may receive a portion of the wall. The portion may be fixed to the body. The body may retract toward a central portion of the passage after the anchor engages the wall. The wall may be drawn toward the central passage and the diameter of the passage may be reduced. In some embodiments, a liner may be provided for the passage. In some embodiments, a baffle may be provided for the passage.

6 Claims, 36 Drawing Sheets

U.S. PATENT DOCUMENTS

| | | |
|---|---|---|
| 6,136,006 A | 10/2000 | Johnson et al. .............. 606/108 |
| 6,146,416 A | 11/2000 | Andersen et al. ........... 623/1.15 |
| 6,168,621 B1 * | 1/2001 | Vrba ........................... 623/1.2 |
| 6,190,406 B1 * | 2/2001 | Duerig et al. ................. 623/1.2 |
| 6,203,569 B1 | 3/2001 | Wijay |
| 6,231,561 B1 * | 5/2001 | Frazier et al. ............... 604/500 |
| 6,254,642 B1 | 7/2001 | Taylor |
| 6,264,687 B1 * | 7/2001 | Tomonto ................... 623/1.16 |
| 6,302,917 B1 | 10/2001 | Dua et al. ................. 623/23.68 |
| 6,451,048 B1 * | 9/2002 | Berg et al. ................. 623/1.13 |
| 6,475,236 B1 | 11/2002 | Roubin et al. |
| 6,511,491 B1 * | 1/2003 | Grudem et al. ............. 606/153 |
| 6,558,429 B1 | 5/2003 | Taylor |
| 6,695,878 B1 | 2/2004 | McGuckin et al. |
| 6,764,518 B1 | 7/2004 | Godin |
| 2001/0020189 A1 | 9/2001 | Tayor |
| 2003/0199987 A1 * | 10/2003 | Berg et al. ................ 623/23.64 |
| 2004/0107004 A1 | 6/2004 | Levine et al. |
| 2004/0143342 A1 | 7/2004 | Stack et al. |

\* cited by examiner

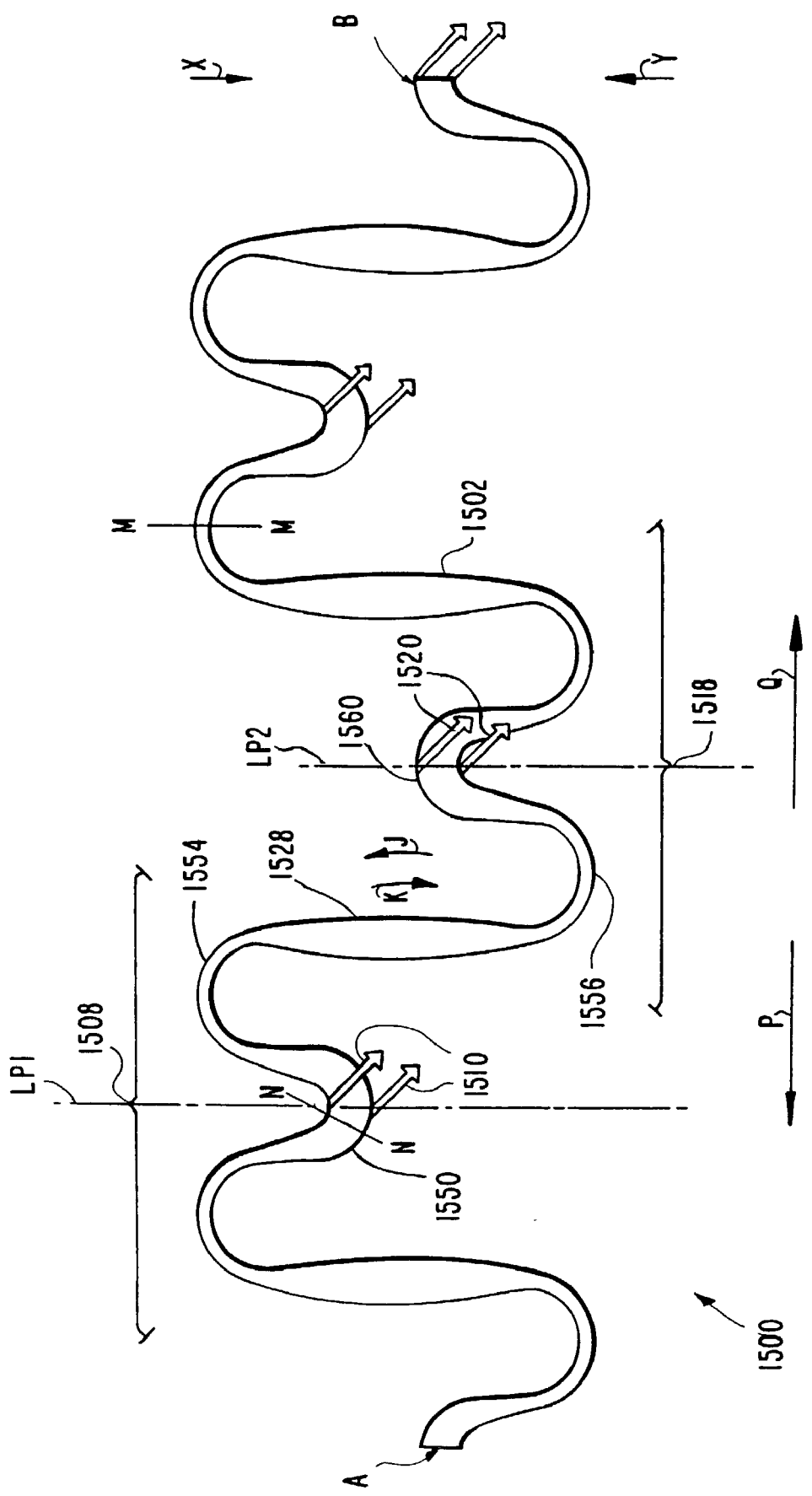

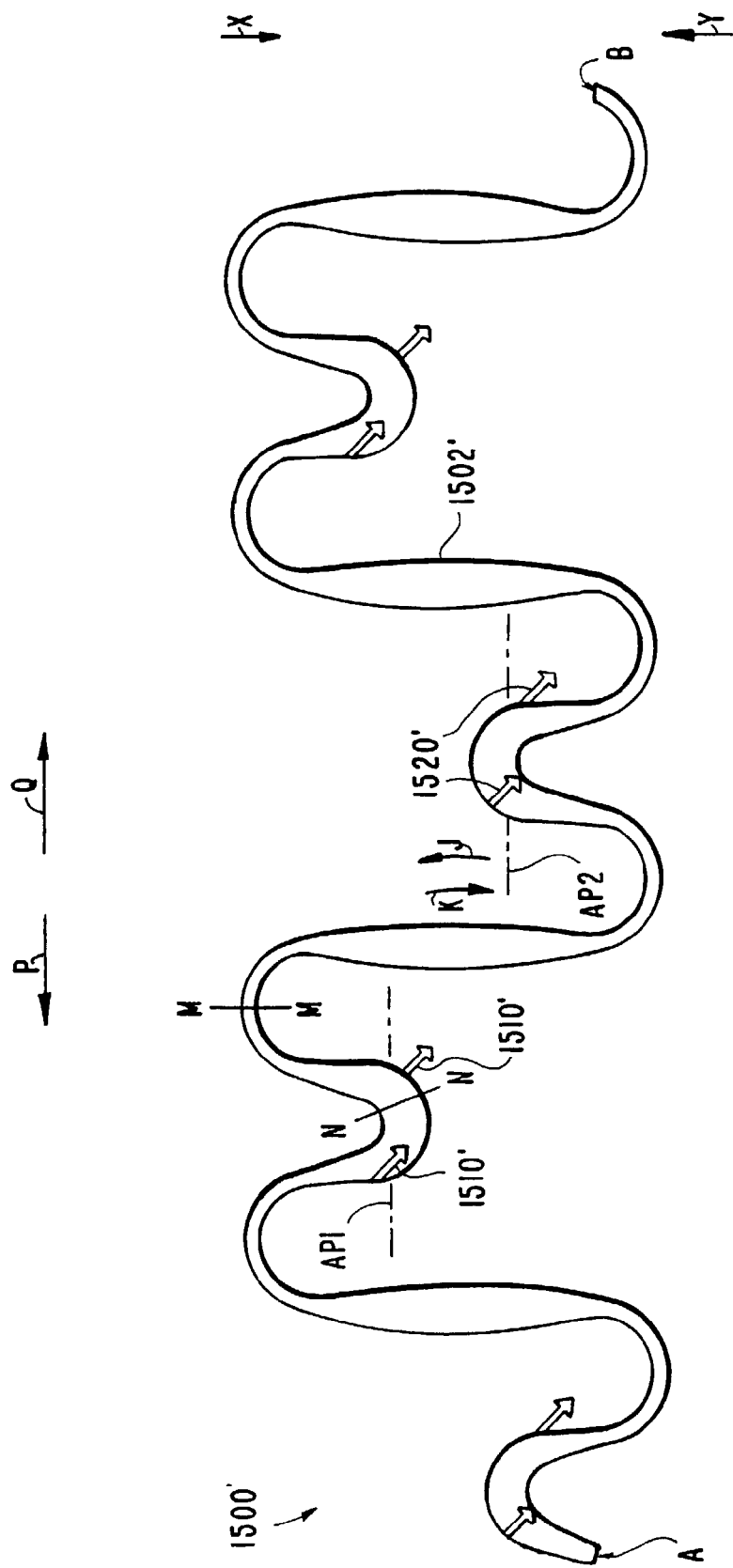

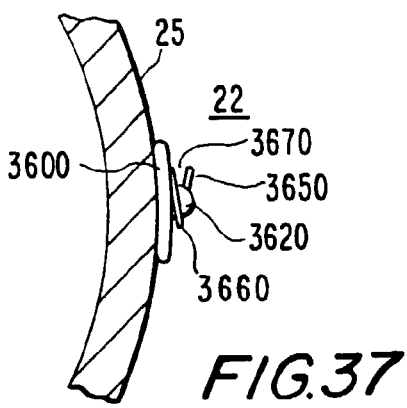
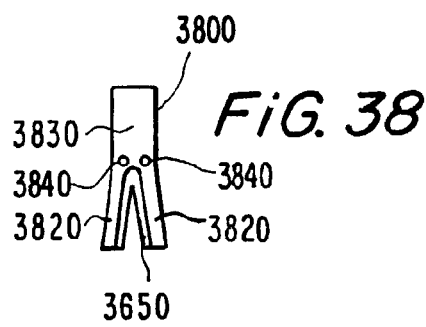
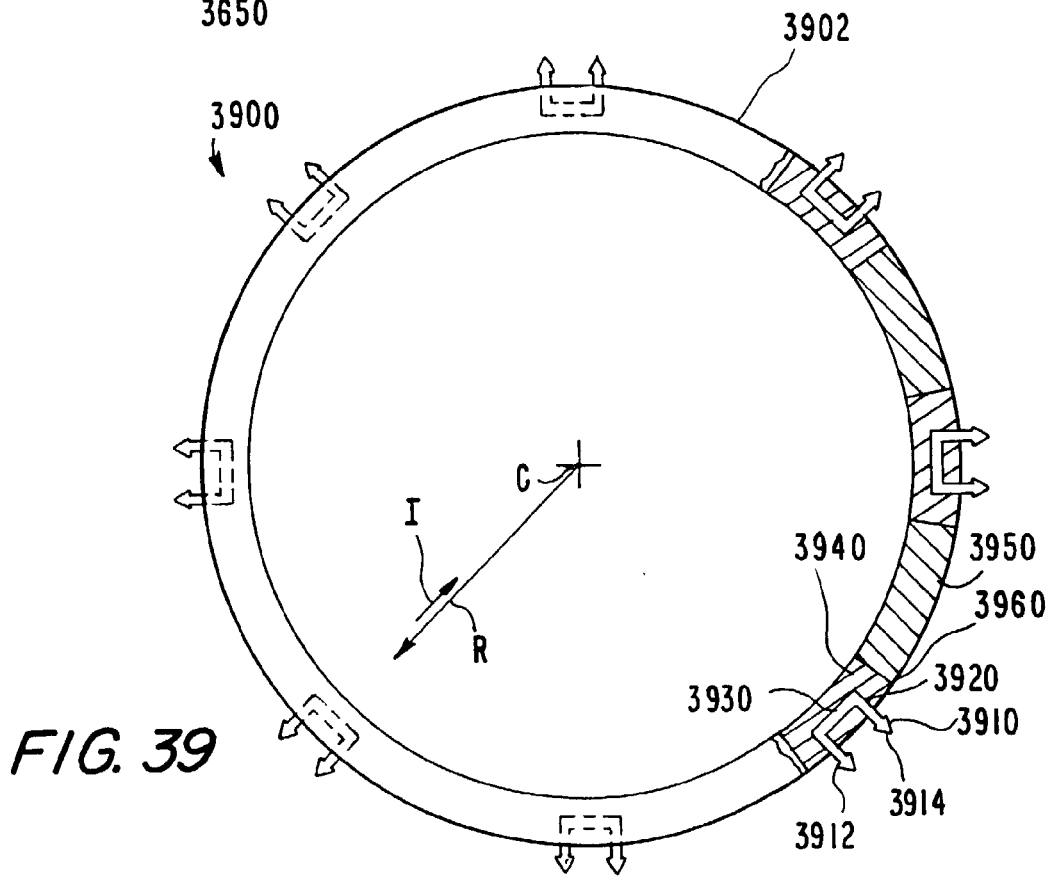

METHODS AND APPARATUS FOR REGULATING THE FLOW OF MATTER THROUGH BODY TUBING

This claims the benefit of copending U.S. Provisional Patent Applications Nos. 60/293,345, filed May 24, 2001, and 60/350,394, filed Jan. 22, 2002, which are hereby incorporated by reference herein in their entireties.

BACKGROUND OF THE INVENTION

The present disclosure concerns apparatus and methods for improving the function of biological passages. The ability of biological passages to expand and contract actively or passively to regulate the flow of solids, liquids, gases, or combinations thereof, may be compromised by defects or disease. One example of a condition associated with decreased functionality of a body passage is Gastro Esophageal Reflux Disease (hereinafter, "GERD"), which effects the esophagus. Other body passages that may be subject to dysfunction, defect, and disease include, but are not limited to, a fallopian tube, a urethra (for example, in the case of incontinence), and a blood vessel (for example, in the case of an aneurysm). GERD and esophageal dysfunction will be further described herein for the sake of illustration.

The normal healthy esophagus is a muscular tube that carries food from the mouth through the chest cavity and into the upper part of the stomach. A small-valved opening in the distal esophagus, called the lower esophageal sphincter (hereinafter, "LES"), regulates the passage of food into the stomach. When functioning properly, the LES muscle presents a barrier to the reflux of acid or food back into the esophagus. The LES also regulates the stomach intra-gastric pressures, regulating acidic gases from refluxing from the stomach back into the esophagus. The LES, when functioning properly, will open to allow gases to be vented from the stomach. A healthy LES at rest can resist pressure from stomach gases that are at least 10 mm Hg greater than normal intragastric pressure. This pressure difference can regulate the amount of acidic fluid that refluxes from the stomach into the esophagus. The LES is controlled largely by two components. The primary component is intrinsic smooth muscle of the distal esophagus wall. The second component is the skeletal muscle of the crural diaphragm or esophageal hiatus. The diaphragm is a muscle separating the stomach from the chest. Studies have shown that the diaphragm may act as a sphincter around the lower end of the esophagus. The esophageal hiatus is the opening in the diaphragm where the esophagus attaches to the stomach.

If the LES relaxes, atrophies, or degrades for any reason, the contents of the stomach, which may be acidic, are allowed back into the esophagus resulting in reflux symptoms. The major mechanism for esophageal reflux, which may be associated with GERD, is the relaxation of one or both of the LES or hiatal diaphragm sphincter mechanisms. Normally occurring mechanisms that diminish or prevent GERD include peristaltic squeezing by the esophageal body, gravity (when a person is in an upright position), and neutralization by saliva.

Chronic or excessive acid reflux exposure may cause esophageal damage. Drugs may be required to manage symptoms of the damage and medical intervention, including surgical or endoscopic procedures, may be required to repair the damage.

The lining of the esophagus is called mucosa. Chronic exposure to stomach gases may cause the mucosa to become inflamed or ulcerated. Inflamed or ulcerated mucosa may lead to problems that may require medical intervention.

Hiatal hernias are often associated with GERD. If the esophageal hernia becomes enlarged (herniated), the LES function may be compromised and the risk of GERD increased. (A hiatal hernia occurs when the upper potion of the stomach moves up through an opening in the diaphragm.)

Barrett's Esophagus is a disease of the esophagus that may compromise esophageal function. This disease may occur when the tissue that ordinarily lines the esophagus migrates away from the lower part of the esophagus to avoid exposure to the acidic fluids against the sensitive mucosa. Barrett's Esophagus is often a precursor to esophageal cancer.

The most common symptom of GERD is dyspepsia (commonly known as "heartburn"). Dyspepsia may be defined as an acute burning sensation in the chest area typically, behind the sternum. Other symptoms of GERD may include hemorrhage, pulmonary disorders, chronic cough, intermittent wheezing, ulcers, Barrett's esophagus, and esophageal cancer.

One conventional surgical treatment for GERD is fundoplication. In this procedure the upper part of the stomach is wrapped around the lower part of the esophagus. This highly invasive procedure is often initially successful, but has a high risk of morbidity (including, e.g., infection and bleeding).

Another conventional treatment for GERD is surgical suturing of a pleat of tissue between the LES and stomach to make the lower esophagus tighter. Suturing may be performed endoscopically using a suturing device on the end of an endoscope inserted into the esophagus through the mouth. Endoscopic procedures are less invasive than open surgery, but still require surgical incisions and great skill.

Surgery, whether endoscopic or open (such as fundoplication) may provide a basic mechanical correction. Surgical procedures may relocate and affix existing tissue of the stomach, esophagus, or both to add support and structure to the LES. LES strength is increased by the added support, thus reducing the incidence of reflux.

Yet another conventional treatment for GERD includes the use of pharmaceutical drugs. The drugs may include acid blockers that may reduce the production of acid by the stomach. The drugs may be effective to reduce the symptoms of mild GERD, but do not treat LES dysfunction. In general, the drugs must be administered indefinitely to maintain their efficacy.

Currently, according to the American Gastroenterological Association, over $12 billion is estimated to be spent on the treatment of GERD annually in the USA alone. It is estimated that $8 billion is spent on drugs. According to a Gallup® poll, 45% of patients taking heartburn drugs report that current remedies do not relieve all symptoms and more than half agree that they would try anything new to relieve their heartburn.

Therefore, it would be desirable to provide improved apparatus and methods for the treatment of a dysfunctional body passage.

BRIEF DESCRIPTION OF THE DRAWINGS

The above and other objects and advantages of the invention will be more apparent upon considering the following detailed description taken in conjunction with the accompanying drawings, in which like reference characters refer to like parts throughout, and in which:

FIG. 15 is a perspective view of apparatus in accordance with the principles of the invention;

FIG. 15A is a perspective view of apparatus in accordance with the principles of the invention;

FIG. 37 is a partial sectional view of apparatus in accordance with the principles of the invention disposed in the biological passage shown in FIG. 20;

FIG. 38 is an elevational view of apparatus in accordance with the principles of the invention;

FIG. 39 is a sectional view of apparatus in accordance with the principles of the invention;

DETAILED DESCRIPTION OF THE INVENTION

Figure 1:
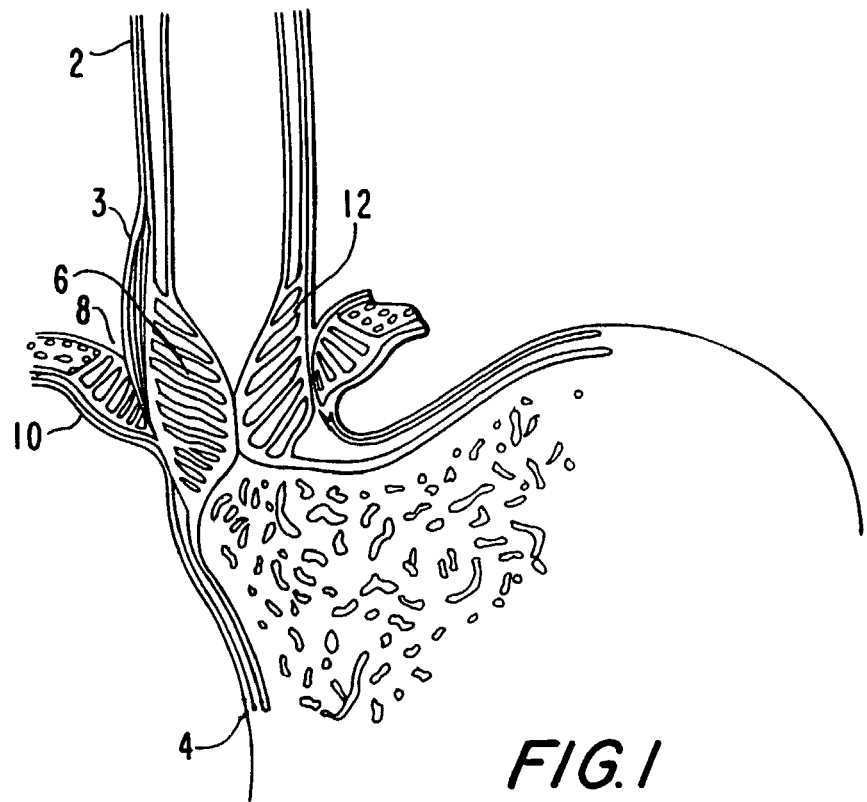
FIG. 1 is a sectional view of an illustrative healthy biological passage.

The invention may provide apparatus and methods for reducing the diameter or providing inwardly directed radial support to a portion of a biological passage. The invention may be used in a wide variety of biological passages including, but not limited to, passages that may be present in the alimentary canal, the digestive system, the respiratory system, the circulatory system, the reproductive system, and the excretory system.

Some embodiments of the invention may include a body having a bore that defines a central axis. (The axis may follow an approximately central path through the body and in some embodiments may not be a straight line.) The central axis may define an axial, or longitudinal, direction. A plane perpendicular to or nearly perpendicular to the central axis may be referred to herein as an axial plane. The body may be configured to expand away from the axis. The body may be configured to contract toward the axis.

At least one anchor may be coupled to the body. The anchor may be configured to engage a portion of the passage, for example, a portion of a passage wall. The anchor may be configured to engage a portion of a passage inner wall. The body may be allowed to contract to pull the wall toward the axis. In some embodiments, the body may be a "reverse stent." In some embodiments, the body may be a band.

In some embodiments, the body may include an elastic material. In some embodiments, the body may include a metal. In some embodiments, the body may include an alloy. In some embodiments, the body may include an inert material. In some embodiments, the body may include a moldable material. As used herein, a material that is biocompatible and resistant to reaction with biochemical solids, liquids, and gases may be an inert material. Stainless steel, nickel titanium alloy, tantalum and other non-reactive metals may be inert. Polymers such as PTFE, polyurethane, polyamide, and those sold under the trademark PEBAX by Elf Atochem North America may be inert. Medical grade metals and polymers may be inert.

The anchor may extend radially away from the axis. The anchor may extend in a non-radial direction away from the axis. The anchor may extend in a curved path away from the axis. The anchor may be pushed radially outward into the inner wall. The anchor may be twisted or rotated about the axis to engage the inner wall.

In some embodiments, the anchor may include an elastic material. In some embodiments, the anchor may include a metal. In some embodiments, the anchor may include an alloy. In some embodiments, the anchor may include a polymer. The anchor may include inert material. Some embodiments may include one or more anchors having more than one of the foregoing features. The anchor may be any suitable type of anchor, including any of the anchors described herein.

In some embodiments of the invention, one or more anchors may be present in or near an axial plane of the body. The axial plane may remain stationary or nearly stationary in the longitudinal direction when the body is deformed in the radial direction. This feature may reduce stress on the passage wall near an anchor if the body deforms in connection with deployment in the passage. The feature may reduce stress on the passage wall near the anchor if the body deforms in response to deformation of the biological passage. The biological passage may deform in response to muscular action, physiological processes, or any other processes. For example, the passage may deform in response to peristalsis, circulatory pumping, excretory processes, reproductive processes, or other physiological processes.

In some embodiments of the invention, the anchor may be shaped like a dart. In some embodiments, the anchor may be include a "catch". As used herein, a catch is a feature of an anchor that may be used to resist the withdrawal of the anchor from tissue. In some embodiments, a catch may be used to pinch or pin tissue. In some embodiments, a catch may hook into tissue (for example, as does a barb). In some embodiments, the anchor may include a staple. The staple may be C-shaped.

In some embodiments, the invention may include a sheath that may be drawn over the body to protect the inner wall from the anchor, for example, when the body is being inserted into the biological passage. The sheath may deflect the anchor away from a direction extending radially away from the body axis. The sheath may be removed to engage the anchor with the inner wall.

Some embodiments of the invention may include a lining. The lining may cover the entire surface of the body. The lining may cover a portion of the body. The lining may cover the anchor. In some embodiments, the lining may include an inert material.

Some embodiments of the invention may include a therapeutic substance. The substance may be present in or on the body. The substance may be present in the anchor, on the anchor, or both. The substance may be present in or on the lining. The substance may be embedded in a porous portion of the invention. The substance may elute from a portion of the invention into the tissue of the biological passage. The substance may include an agent configured to heal the tissue from a disease, defect, infection, inflammation, trauma, or any combination thereof. The substance may include an agent configured to physically protect the tissue from acidic compounds. The substance may include an agent configured to chemically protect the tissue from acidic compounds. For example, the substance may act to neutralize an acidic compound. The substance may be a drug. The substance may include a steroid. The substance may include an antibiotic.

Some embodiments of the invention may include first and second crimping members. The crimping members may be configured to apply force to the anchor to crimp the anchor to the inner wall of the biological passage. In some of these embodiments, the anchor may have prongs and be shaped like a staple, a "C", a "U", or any other suitable form. The crimping members may be used to bend the prongs to engage the biological passage. The crimping members may be used to secure the prongs to the biological passage.

In embodiments of the body that include a moldable material, the anchor may be insert molded into a portion of the body. In some of these embodiments, the anchor may be wholly or partially embedded in the polymer. The anchor may be made from a material that is less elastic than the polymer. When the body is expanded away from the axis, the body portion housing the anchor may become thinner in the radial dimension. As the body portion thins, the anchor may protrude through and extend radially beyond the portion. This feature may permit the device to be inserted into the passage with the anchor in a retracted position. The feature may permit the anchor to be exposed or "activated" automatically as the body is expanded. In embodiments having an anchor with a catch, this feature may permit the anchor to pinch a portion of the biological passage inner wall against the body when the body contracts.

In some embodiments, the body may include portions having different relative flexibilities. Some portions may have high flexibility. Some portions may have low flexibility. One or more anchors may be coupled to a low flexibility portion. One or more anchors may be coupled to a high flexibility portion. When the body expands, contracts, or otherwise deforms (for example, in response to peristalsis or other motion), the deformation may be concentrated in the portions having high relative flexibility. An anchor or anchors coupled to a low flexibility portion may be subject to less stress, less displacement, or both than if coupled to a relatively high flexibility portion.

High flexibility portions may be, for example, thin, long, elastic, extensible, rotatable, or otherwise compliant. Low flexibility portions may be, for example, thick, short, inelastic, fixed against rotation or shorter, or otherwise noncompliant.

Portions having low flexibility may be referred to as "nodal" portions. Nodal portions may be coupled to high flexibility portions that may be referred to as "transitional" portions. In some embodiments, the body may include a series of alternating nodal and transitional portions arranged in a loop around the central axis. The longitudinal extension of a portion (i.e., the extension in a direction parallel or approximately parallel to the axis) may be referred to as an "axial spread." In some of these embodiments, transitional portions may undergo rotation to reduce the displacement of nodal portions when the body is deformed.

In some embodiments, a node may be a portion of a relatively inflexible band. The node may be joined to another node by a transition member that bridges a gap between the nodes. The bridge member may include or be configured as a spring.

In some embodiments, the body may have the shape of a lobed strip. The strip may have a sinusoidal or wave-like form. The strip may form a closed ring or band. In some embodiments, the strip may form a ring or band that is not completely closed. In some embodiments having lobes, a lobe may be sutured to the biological passage.

In some embodiments, the body may include an opening that may receive a portion of the inner wall when the body contracts. As the body draws the passage toward the axis, inner wall material may be forced into an increasingly small volume and portion may intrude into the opening. Both open and closed cell bands (described below) and any other suitable type of band, may have an opening through which inner wall tissue may intrude. Some of these embodiments may include a fastener, a suture, or both fasteners and sutures that may be used to secure the portion of the body passage that intrudes through the opening. A clip may be attached to intruded tissue within the lumen of the band to prevent the tissue from receding back through the opening. In some embodiments, the portion received by the openings may be permanently secured.

In some embodiments, the invention may include a catheter for inserting the body into the biological passage.

In some embodiments, the body may be installed in the biological passage by placing the body in a portion of the passage, expanding the body, engaging the anchor or anchors with the passage inner wall, and allowing the body to contract. In some embodiments, the body may be expanded and the anchor or anchors secured in the inner wall using a balloon. In some embodiments, the body may be expanded sufficiently to partially engage the anchor or anchors with the wall. In some of these embodiments, a crimping device may be used to complete the engagement of the anchor or anchors with the wall. In some embodiments, the crimping device may be used to secure the anchor or anchors in the wall without previous partial engagement of the anchor or anchors.

In some embodiments, the body may be expanded without a balloon. For example, an expansion wedge may be passed through the bore. The wedge may have an outside diameter greater than the inside diameter of the bore in a contracted state. The wedge may be tapered to facilitate entry into the bore. The diameter of the wedge may be selected or adjusted to provide a selected expansion of the body. In some of these embodiments, the minimum outward radial displacement of an anchor or anchors may be selected.

In some embodiments, the invention may include a liner for a portion of the biological passage. Some of those embodiments may include one or more anchors to secure the liner to the biological passage. The liner may include a first plurality of anchors, a second plurality of anchors, and a sleeve. The sleeve may extend from the first plurality of anchors to the second plurality of anchors. The sleeve may be configured to conform to the inner wall of the biological passage. The liner may include a polymer such as PTFE, polyurethane, polyamide, and PEBAX®. The liner may include any suitable medical polymer. The liner may include any suitable material that does not readily react with biological fluids such as stomach acid, biological waste, or other materials that may be present in a biological passage.

In some embodiments, the invention may include a baffle for a portion of a biological passage. The baffle may include a body that has an inner wall that defines a bore. The baffle may include at least one projection or finger that extends from the inner wall into the bore. The bore may be configured to be secured in the passage, for example, using an anchor or anchors. The finger may obstruct the flow of matter through the passage. The finger may provide surface area that may promote biological or biochemical processes that neutralize or otherwise transform compounds that may be undesirable or harmful to the passage or other biological entities. The baffle may include an inert material.

Figure 2:
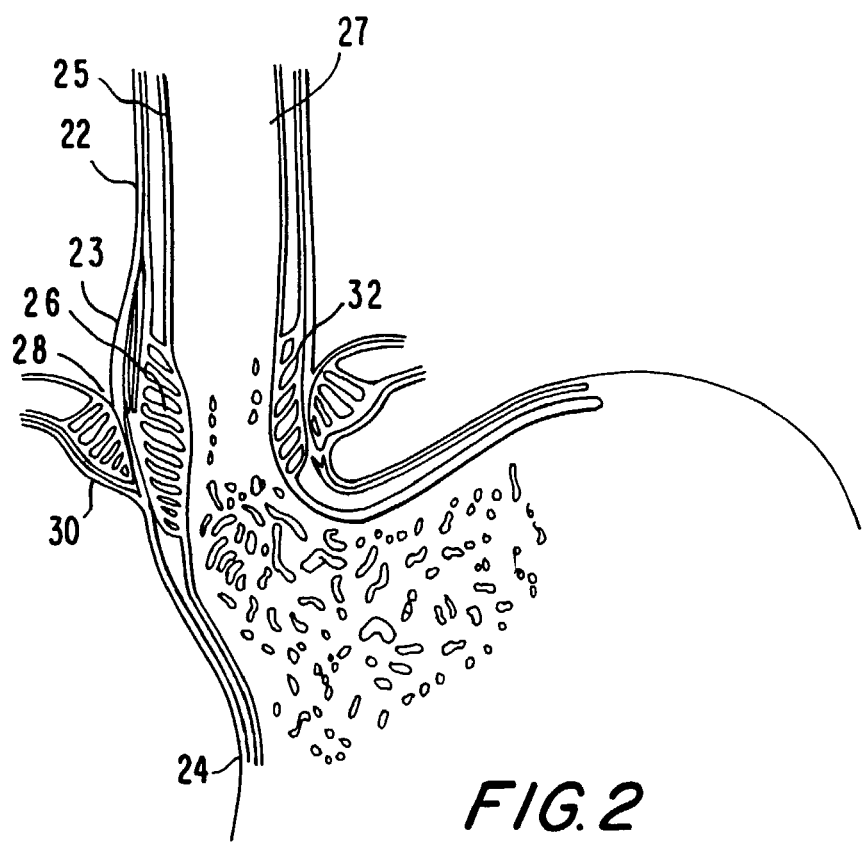
FIG. 2 is a sectional view of a defective biological passage.

FIGS. 1 and 2 show esophageal anatomy. FIG. 1 shows healthy esophagus 2, including distal esophagus 3 connected to stomach 4. LES 6 is located at the junction of esophagus 2 and stomach 4 where esophagus 2 passes through hiatus 8 in hiatal diaphragm 10. Sling fibers 12 in LES 6 are smooth muscle tissue that may regulate distal esophagus 3. Hiatus 8 may externally support and regulate LES 6. LES 6 is normally open at rest.

FIG. 2 shows esophagus 22, which may be diseased, defective, or otherwise dysfunctional, including lumen 27 and distal esophagus 23 connected to stomach 24. LES 26 is located at the junction of esophagus 22 and stomach 24 where esophagus 22 passes through hiatus 28 in hiatal diaphragm 30, which may be diseased or defective. Sling fibers 32 in LES 26 may be unable to regulate distal esophagus 23 and LES 26 may be unable to be closed or may be too easily opened. Hiatal diaphragm 30 may not externally support esophagus 22 adjacent LES 26.

Figure 3:
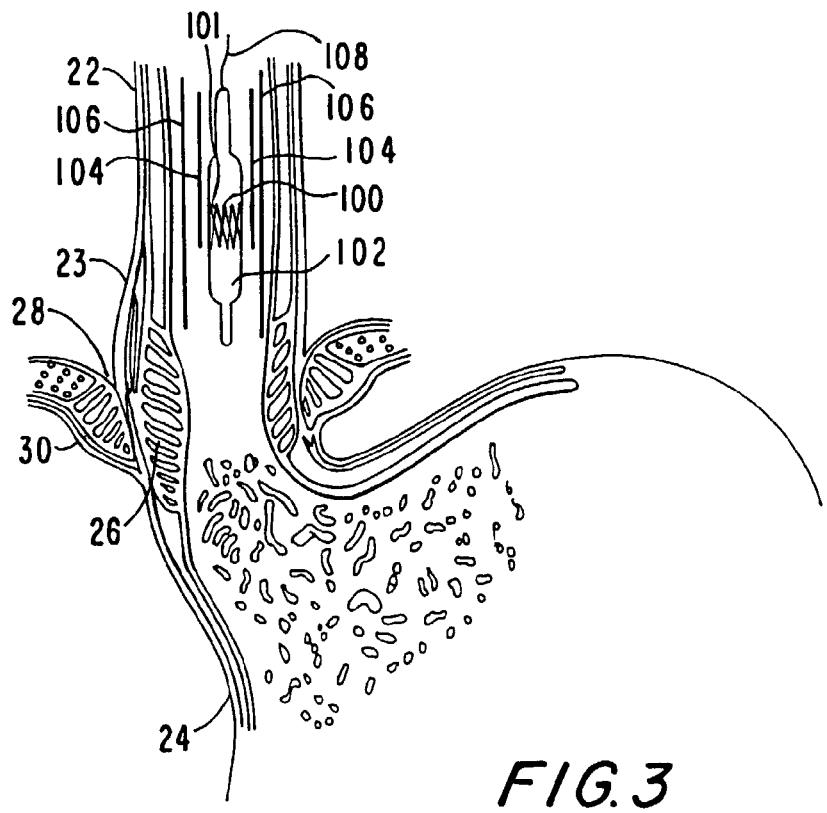
FIG. 3 is a partial sectional view of apparatus in accordance with the principles of the invention disposed in the biological passage shown in FIG. 2.
Figure 69:
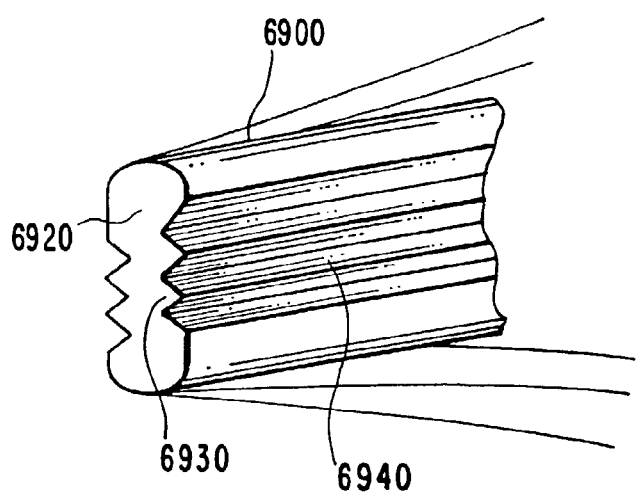
FIG. 69 is a perspective view of an apparatus in accordance with the principles of the invention.

Illustrative examples of embodiments in accordance with the principles of the present invention are shown in FIGS. 3–69.

FIG. 3 shows band 100, which may include one or more members such as member 101, positioned in distal esophagus 23 above LES 26. Band 100 may be installed in distal esophagus 23 to make it easier for LES 26 to close. Band 100 may be supported by balloon 102, which may be at least partially inflated. Sheath 104 may be present around band 100 to deflect anchors (not shown) that may be coupled to the outside of band 100. Catheter 106 may be used to deliver or guide band 100, balloon 102, and shield 104 to distal esophagus 23. Balloon 102 may be positioned using catheter shaft 108.

Figure 4:
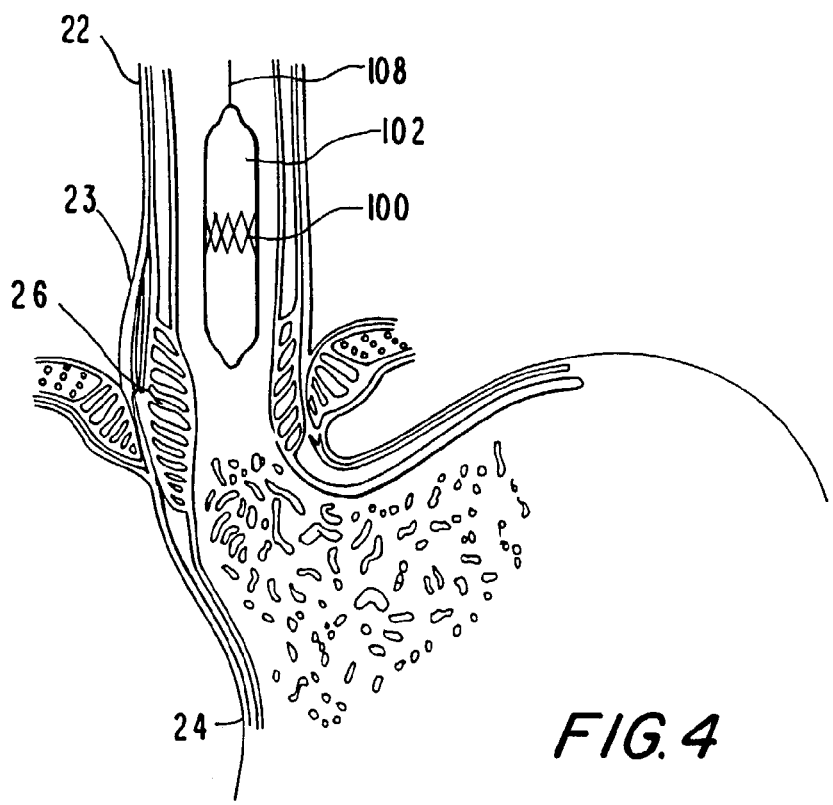
FIG. 4 is an elevational view of apparatus in accordance with the principles of the invention disposed in the biological passage shown in FIG. 2.

FIG. 4 shows band 100 positioned in distal esophagus 23 above LES 26. Sheath 104 and catheter 106 (shown in FIG. 3) have been removed in preparation for deployment of band 100. Band 100 may be supported by balloon 102, which may be inflated minimally to retain band 100. Balloon 102 may be inflated to a more advanced degree to begin installing band 100.

Figure 5:
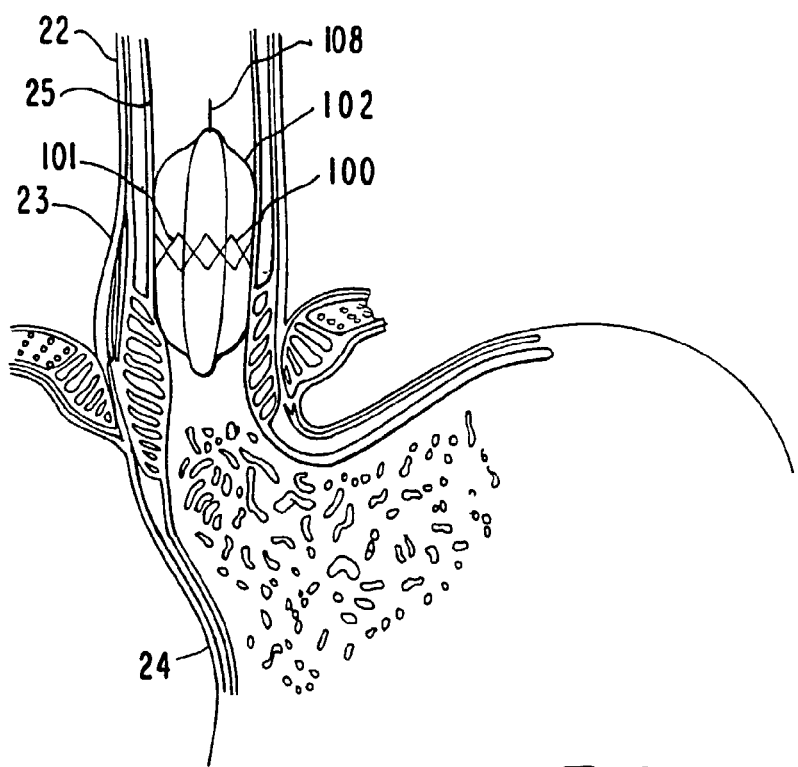
FIG. 5 is an elevational view of apparatus in accordance with the principles of the invention disposed in the biological passage shown in FIG. 2.

FIG. 5 shows band 100 in an advanced stage of deployment in distal esophagus 23. Balloon 102 is shown in an advanced stage of inflation to expand band 100 into proximity with wall 25 of esophagus 22. An anchor or anchors (not shown), which may be coupled to band 100, may be pushed into and engaged with wall 25 by the expansion of band 100. The anchor or anchors may be secured to wall 25 by crimping.

Figure 6:
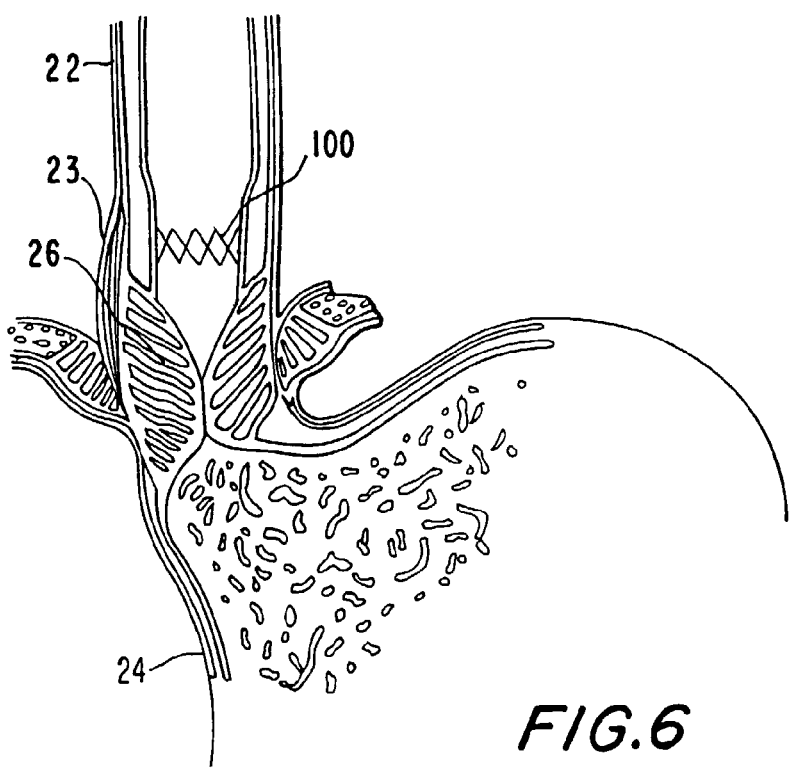
FIG. 6 is an elevational view of apparatus in accordance with the principles of the invention disposed in the biological passage shown in FIG. 2.

FIG. 6 shows band 100 in a state of contraction or partial contraction in distal esophagus 23 after balloon 102 has been removed. Balloon 102 may be deflated or partially deflated before withdrawal from band 100 or esophagus 22. An anchor or anchors (not shown) that may secure band 100 to wall 25 may reduce the diameter of distal esophagus 23 as band 100 contracts. FIG. 6 shows that by reducing the diameter of distal esophagus 23, LES 26 may close.

Figure 7:
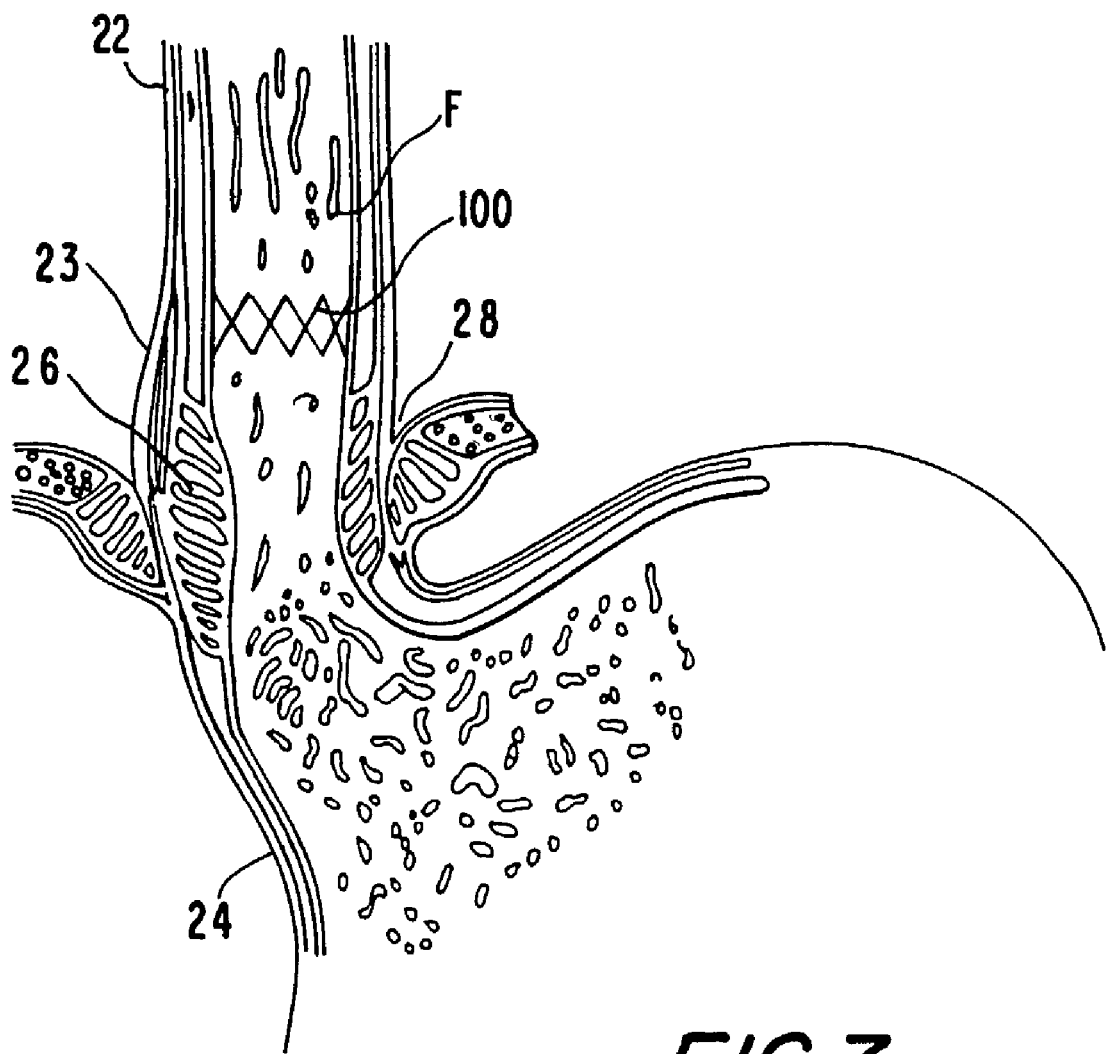
FIG. 7 is an elevational view of apparatus in accordance with the principles of the invention disposed in the biological passage shown in FIG. 2.

FIG. 7 shows band 100 deployed in distal esophagus 23. LES 26 is in an open state and may allow the passage of matter such as food F between esophagus 22 and stomach 24. The force with which band 100 contracts may be selected (by selecting band flexibility, material properties, or both, for example) to provide a selected degree of support to LES 26. The force may be selected to compensate for a particular degree of deficiency in LES 26 or hiatus 28. The force may be selected to allow LES 26 to open in response to a particular degree of muscular forcing, peristalsis, passage of matter along esophagus 22, reflux of matter from stomach 24, or any combination thereof. The anchor or anchors may be axially stationary or nearly axially stationary with respect to distal esophagus 23 when band 100 radially expands or radially contracts.

Figure 8:
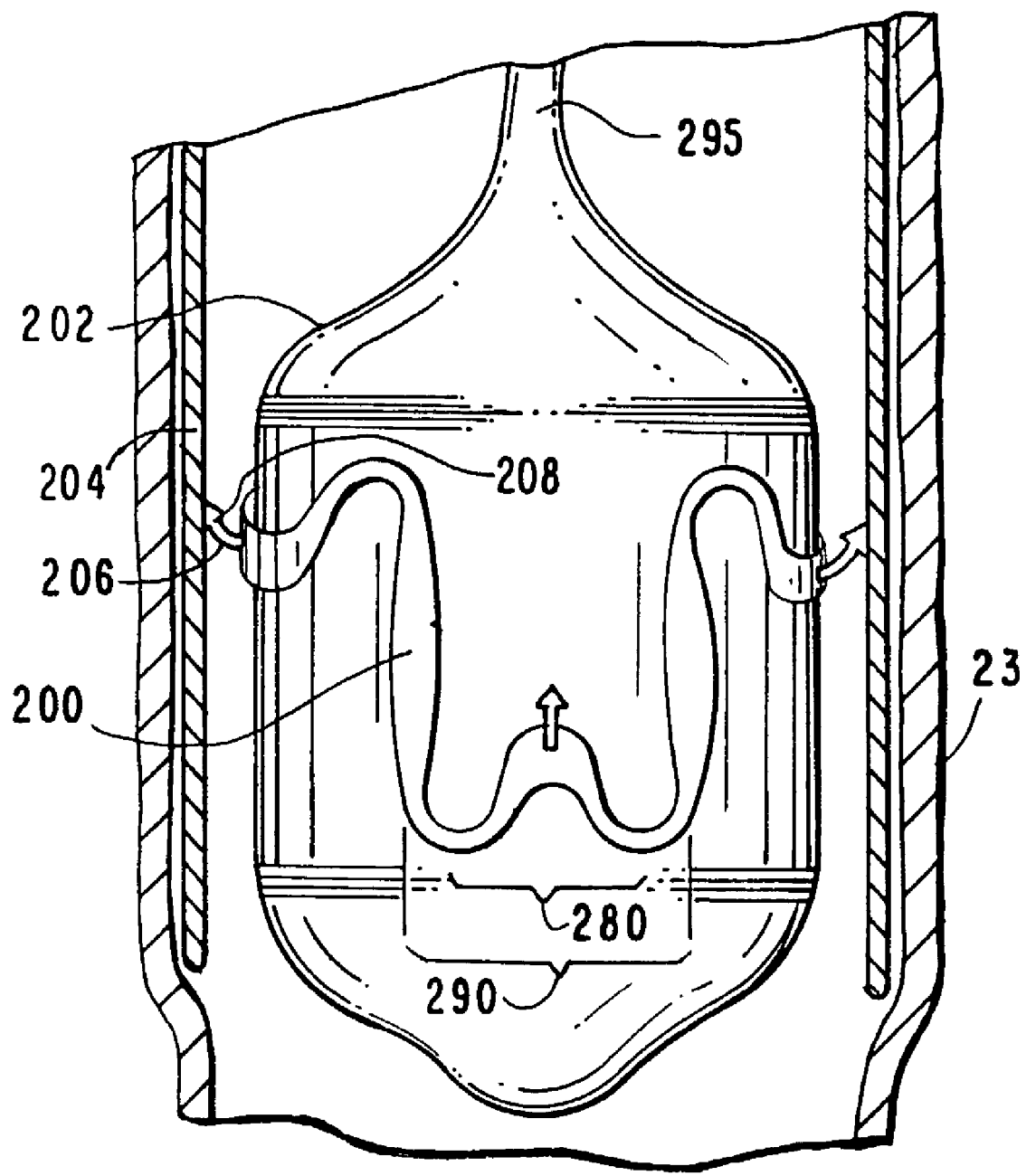
FIG. 8 is a partial perspective view of apparatus in accordance with the principles of the invention in the biological passage shown in FIG. 2.

FIG. 8 shows band 200 which may support anchor 206. Anchor 206 may engage distal esophagus 23. Band 200 may support more than one anchor having the features of anchor 206. Band 200 may include one or more lobes such as lobe 290. Lobe 290 may include one or more curved portions such as curved portion 280. Curved portion 280 may support one or more anchors. Anchor 206, which may include one or more barbs such as barb 208, may be maintained in a retracted state by delivery sheath 204. Balloon 202 may be at least partially inflated to retain and/or position band 200. The position of balloon 202 may be controlled by catheter shaft 295.

Figure 9:
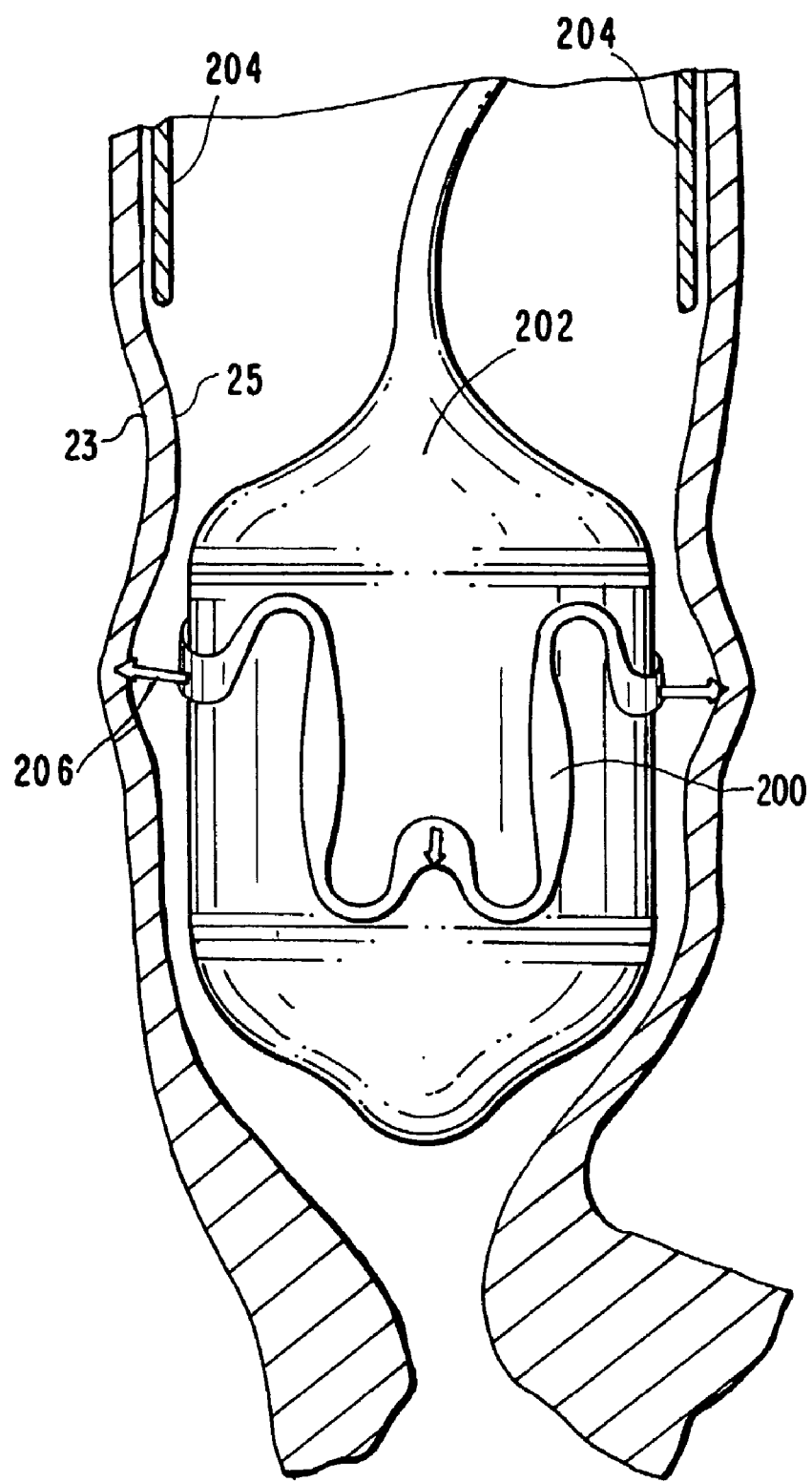
FIG. 9 is a partial perspective view of apparatus in accordance with the principles of the invention in the biological passage shown in FIG. 2.

FIG. 9 shows band 200 positioned in distal esophagus 23. Balloon 202 is in an at least partially expanded state. Anchor 206 is in contact with wall 25 of distal esophagus 23. Delivery sheath 204 is withdrawn in a proximal direction from band 200 allowing anchor 206 to relax to a direction facing wall 25. (As used herein, the proximal direction is toward the point of entry of the apparatus into the biological passage. The distal direction is opposite the proximal direction. In this example, the point of entry may be the mouth.)

Figure 10:
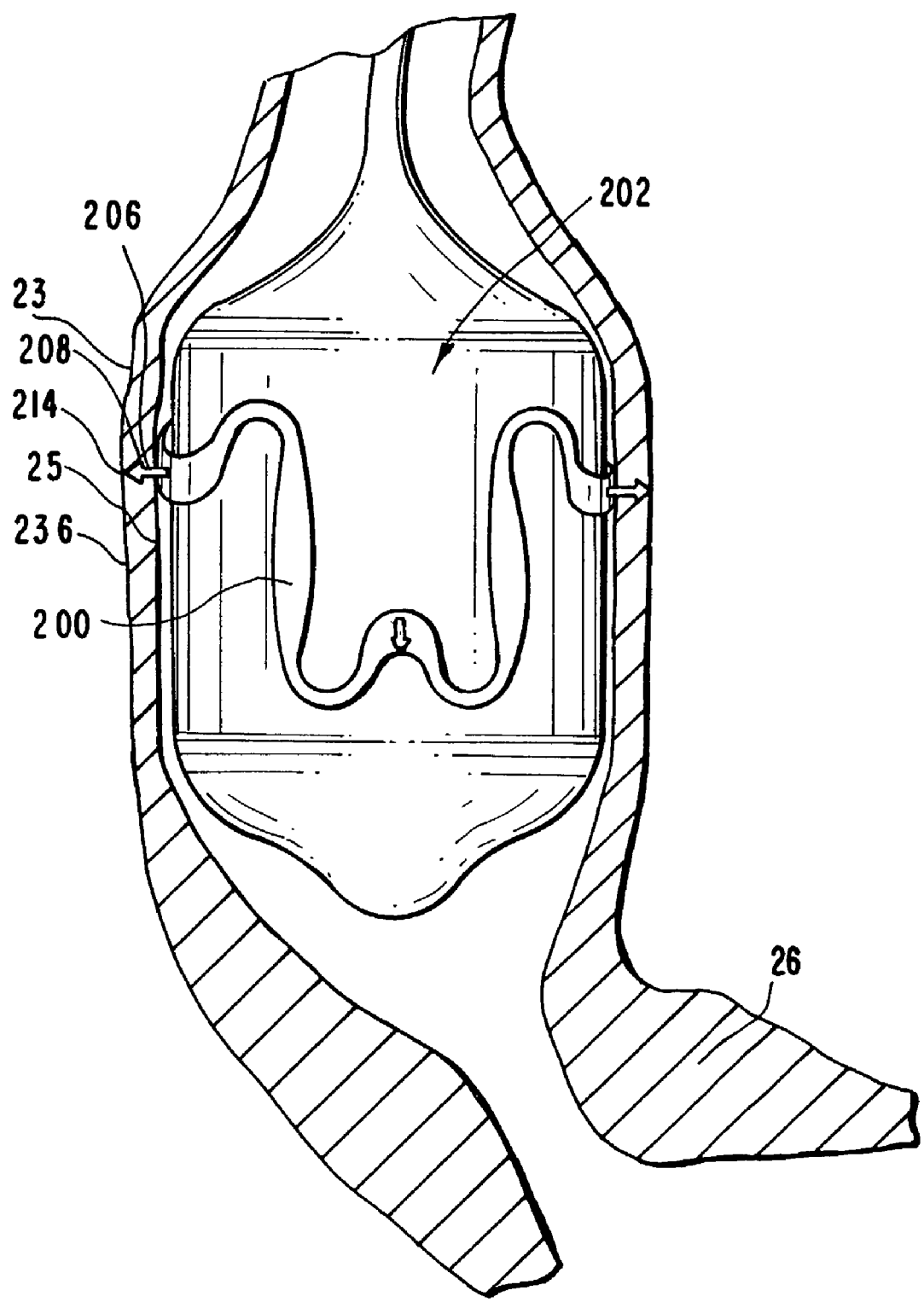
FIG. 10 is a partial perspective view of apparatus in accordance with the principles of the invention in the biological passage shown in FIG. 2.

FIG. 10 shows that balloon 202 may be further expanded to drive anchor 206 into the tissue of distal esophagus 23. Barb 208 may engage anchor 206 with distal esophagus 23. Head 214 of anchor 206 may be positioned throughout the thickness of distal esophagus 23. In some embodiments, head 214 may emerge through outer wall 236 of distal esophagus 23.

Figure 11:
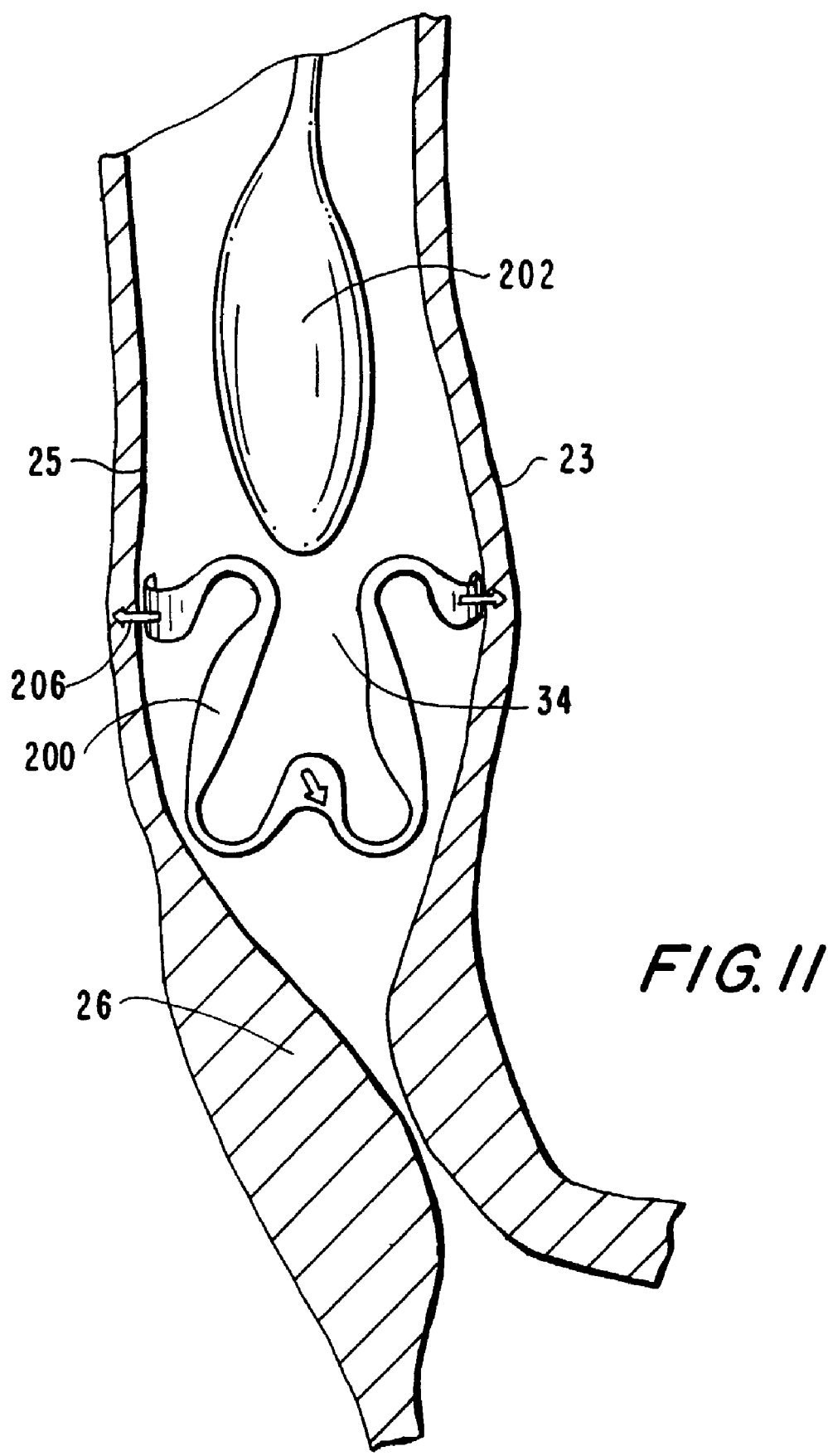
FIG. 11 is a partial perspective view of apparatus in accordance with the principles of the invention in the biological passage shown in FIG. 2.

FIG. 11 shows balloon 202 in a deflated or partially deflated state. Balloon 202 may be withdrawn from band 200 to allow band 200 to retract toward central region 34 of distal esophagus 23. Anchors such as anchor 206 secured to distal esophagus 23 may draw wall 25 toward central region 34. When wall 25 is drawn toward central region 34, LES 26 may be sufficiently supported to achieve the closed state shown in FIG. 11.

Figure 11A:
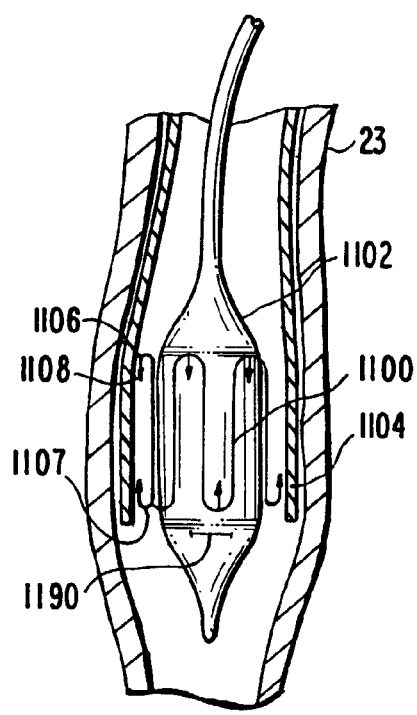
FIG. 11A is a schematic view of apparatus in accordance with the principles of the invention in the biological passage shown in FIG. 2.

FIGS. 11A–11D show an illustrative embodiment of the invention in stages of deployment in distal esophagus 23 that correspond to the stages shown in FIGS. 8–11 in connection with band 200 and apparatus associated therewith. FIG. 11A shows band 1100 which may include an anchor or anchors such as anchors 1106 and 1107 for engagement with distal esophagus 23. Band 1100 may include one or more lobes such as lobe 1190. In some embodiments, lobe 1190 may not have a curved portion such as curved portion 280 (shown in FIG. 8). Lobe 1190 may support one or more anchors. Anchors 1106 and 1107, which may include one or more barbs such as barb 1108, may be maintained in a retracted state by delivery sheath 1104.

In some embodiments, a retracted anchor may extend in the distal direction as does anchor 1106. In some embodiments, a retracted anchor may extend in the proximal direction as does anchor 1107. In some embodiments, a retracted anchor may extend in the radial direction (not shown). Balloon 1102 may be partially inflated to retain and position band 1100. The position of balloon 1102 may be controlled by catheter shaft 1108.

Figure 11B:
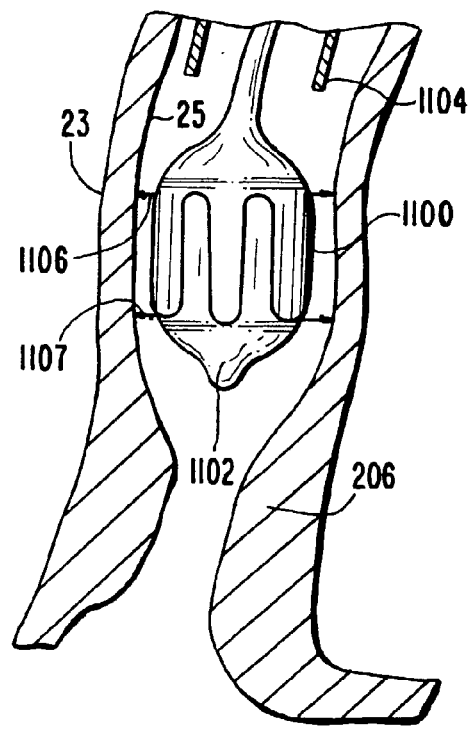
FIG. 11B is a schematic view of apparatus in accordance with the principles of the invention in the biological passage shown in FIG. 2.

FIG. 11B shows band 1100 positioned in distal esophagus 23. Balloon 1102 may be at least partially expanded. Delivery sheath 1104 may be withdrawn in a proximal direction from band 1100 allowing anchors 1106 and 1107 to relax to a direction facing wall 25. One or both of anchors 1106 and 1107 may contact wall 25 of distal esophagus 23.

Figure 11C:
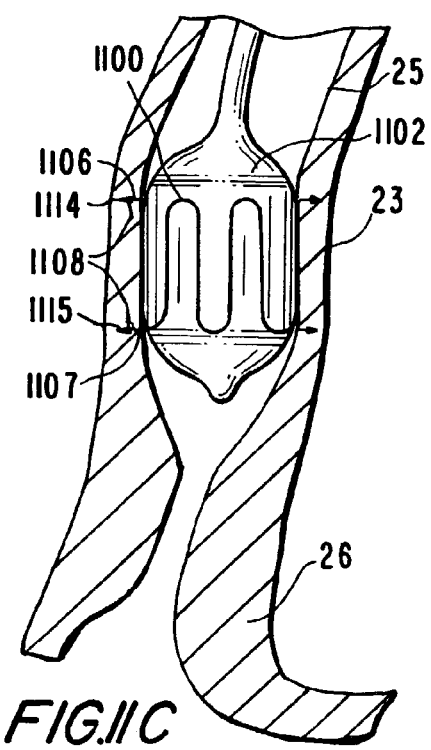
FIG. 11C is a schematic view of apparatus in accordance with the principles of the invention in the biological passage shown in FIG. 2.

FIG. 11C shows that balloon 1102 may be further expanded to drive one or both of anchors 1106 and 1107 into distal esophagus 23. Barbs 1108 may engage one or both of anchors 1106 and 1107 with the tissue of distal esophagus 23. Heads 1114 and 1115 of anchors 1106 and 1107, respectively, may be positioned throughout the thickness of distal esophagus 23. In some embodiments, one or both of heads 1114 and 1115 may extend through the outer wall of distal esophagus 23.

Figure 11D:
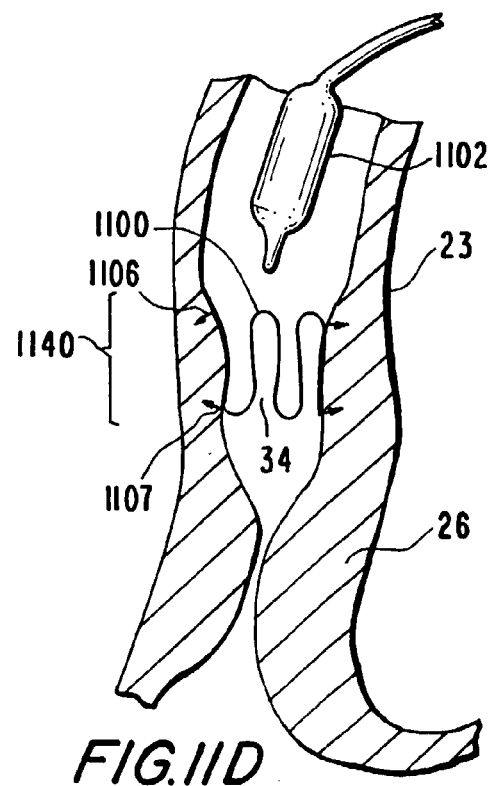
FIG. 11D is a schematic view of apparatus in accordance with the principles of the invention in the biological passage shown in FIG. 2.

FIG. 11D shows balloon 1102 in a deflated or partially deflated state. Balloon 1102 may be withdrawn from band 1100 to allow band 1100 to retract toward central region 34 of distal esophagus 23. Anchors such as anchors 1106 and 1107 secured to distal esophagus 23 may draw wall 25 toward central region 34. Anchors 1106 and 1107 may pull in a portion of wall 25 that extends at least along region 1140. When wall 25 is drawn toward central region 34, LES 26 may be sufficiently supported to achieve the closed state shown in FIG. 11.

Figure 12:
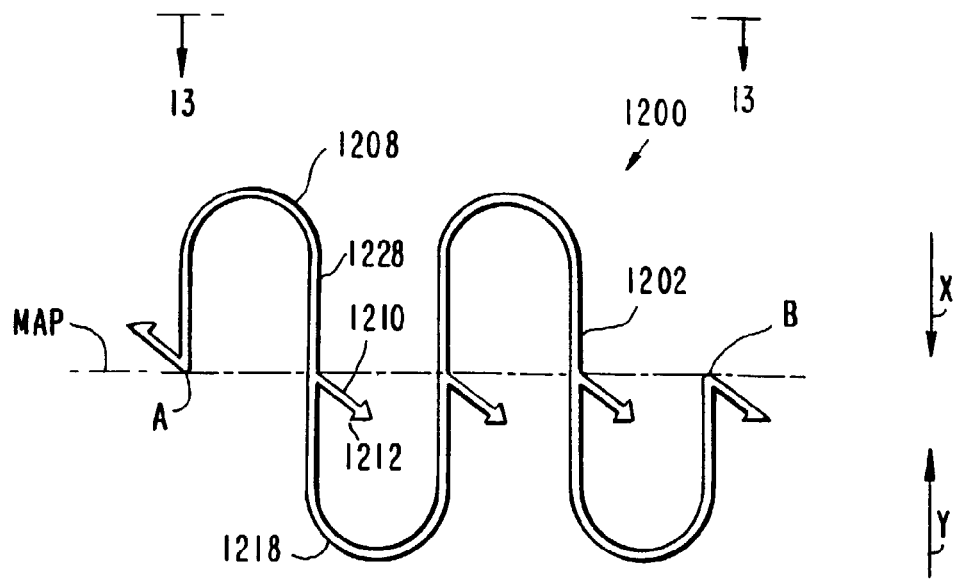
FIG. 12 is a perspective view of apparatus in accordance with the principles of the invention.

FIGS. 12–17 show illustrative examples of bands. FIG. 12 shows illustrative apparatus 1200 in unrolled form for the sake of illustration. In use, ends A and B may be joined to form a continuous band 1200 into a continuous undulating loop. Apparatus 1200 may include band 1202. In some embodiments, band 1202 may be formed from a tube, in which case ends A and B may be part of a continuous piece of material. Apparatus 1200 may include one or more anchors such as 1210. Anchor 1210 may include one or more barbs such as barb 1212. Band 1200 may include one or more upper lobes such as upper lobe 1208. Band 1202 may include one or more lower lobes such as lower lobe 1218.

In some embodiments, anchor 1210 may be present on or near medial axial plane MAP. Plane MAP may be on or near the longitudinal center of apparatus 1200. In some embodiments, one or more anchors may be present on band 1202 not on or near plane MAP. In some of those embodiments, one or more anchors may be present on the lobes. (Although plane MAP is shown in connection with apparatus 1200, plane MAP may be shown in connection with other embodiments of the invention to illustrate aspects of those embodiments that may correspond to aspects of apparatus 1200.)

Lower lobe 1218 and upper lobe 1208 may be open in directions Y and X, respectively. The presence of open lobes is a feature that may be referred to as "open cell" design. The number of upper and lower lobes present between ends A and B may be less than or greater than the number shown. Lower lobe 1218 may be coupled to upper lobe 1208 by a connecting portion such as connecting portion 1228. In some embodiments, one or more anchors may be present on one or more connecting portions.

Figure 13:
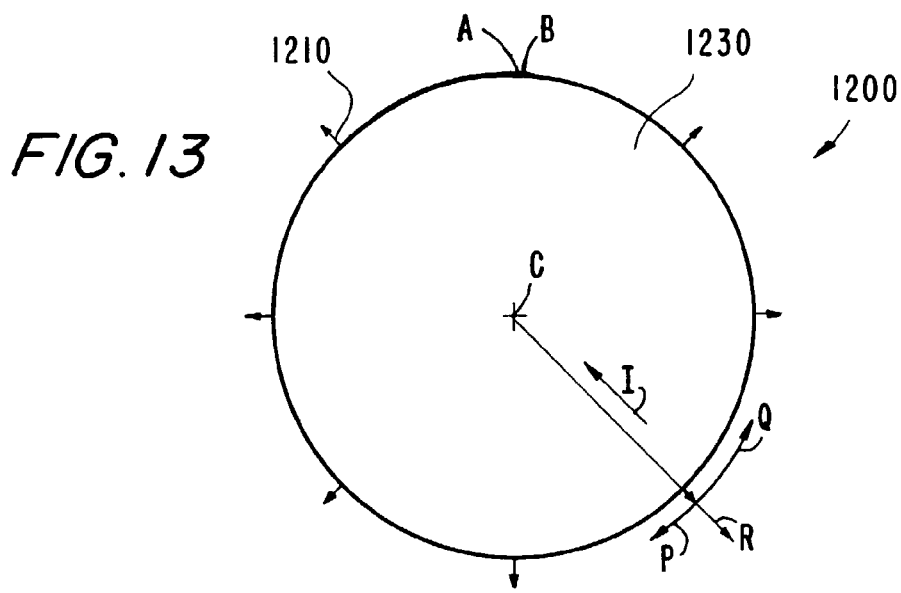
FIG. 13 is a view taken from line 13—13 in FIG. 12 as it would appear after the apparatus shown in FIG. 12 is formed into a closed loop.

FIG. 13 schematically shows illustrative band apparatus 1200 viewed from line 13—13 in FIG. 12, but with ends A and B joined together. Longitudinal or nearly longitudinal directions X and Y are shown in FIG. 12 in connection with apparatus 1200. Axis C and directions R, I, P, and Q are shown in FIG. 13 in connection with apparatus 1200. For the sake of simplicity, the axis and the directions will be used to illustrate aspects of other embodiments of the invention that may correspond to aspects of apparatus 1200. Direction R is a direction that extends radially outward from axis C. Direction I is a direction that extends radially inward toward axis C. In some embodiments, axis C may not be in the exact center of a band. In some embodiments, direction R may be an approximately radially outward direction. In some embodiments, I may be an approximately radially inward direction. For the sake of clarity, direction I may be shown separate from direction R.

Similarly, ends A and B will be used to illustrate aspects of other embodiments of the invention that may correspond to aspects of apparatus 1200.

Central axis C passes through bore 1230 of band 1202. In some embodiments, anchor 1210 may extend in a direction that has components parallel to axis C and radial direction R. In some embodiments, anchor 1210 may extend in a direction that is extends in (or nearly in) radial direction R.

Band 1202 may be expanded in direction R to engage anchors 1210 and 1220 with biological tissue of a biological passage. When band 1202 expands in direction R, it may also expand in directions P. When band 1202 expands in directions P, upper lobes such as lobe 1208 may move farther apart from each other, lower lobes such as lobe 1218 may move farther apart from each other, and connecting portions such as portion 1228 may move farther apart from each other. During the expansion of band 1200, upper lobe 1208 and lower lobe 1218 may move in directions X and Y (shown in FIG. 12), respectively. During expansion of band 1202, plane MAP, and any anchor or anchors positioned in or near plane MAP, may be stationary or nearly stationary with respect to the biological passage in which apparatus 1200 is deployed.

One or more anchors 1210 and 1220 may engage biological tissue. Band 1202 may be allowed to contract in direction I to draw the tissue toward axis C. (Direction I is the opposite of radial direction R, but is shown separately from direction R for the sake of clarity.) During contraction, upper lobes such as lobe 1208 may move closer to each other, lower lobes such as lobe 1218 may move closer to each other, and connecting portions such as portion 1228 may move closer to each other. During contraction of band 1202, plane MAP, and any anchor or anchors positioned in or near plane MAP, may be stationary or nearly stationary with respect to the biological passage in which apparatus 1200 is deployed. Barb 1212 may secure tissue to anchor 1210 during contraction. Barb 1212 may continue to secure tissue to anchors 1210 after contraction is complete.

Figure 13A:
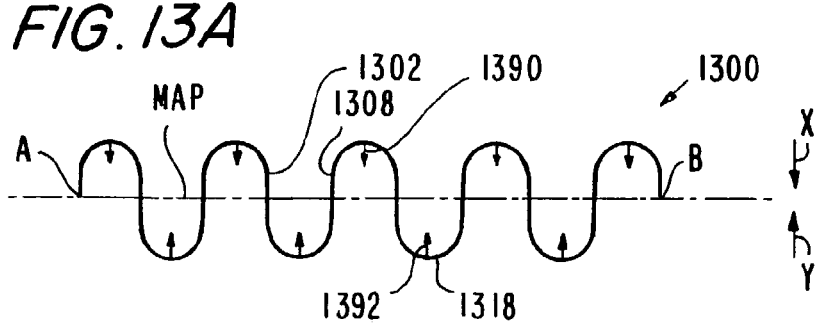
FIG. 13A is a schematic view of apparatus in accordance with the principles of the invention.

FIG. 13A shows illustrative apparatus 1300 in unrolled form for the sake of illustration. Apparatus 1300 may include band 1302. In use, ends A and B may be joined to form band 1302 into a continuous undulating loop. Band 1302 may include one or more upper lobes such as lobe 1308. Band 1302 may include one or more lower lobes such as lobe 1318. One or more upper anchors such as anchor 1390 may be present on upper lobe 1308. One or more lower anchors such as anchor 1392 may be present on lower lobe 1318. In some embodiments, during expansion, upper anchor 1390 and lower anchor 1392 may move in directions X and Y, respectively. In embodiments in which anchors 1390 and 1392 extend in a direction having components parallel to both C and R, the opposing movement of the anchors 1390 and 1392 may help anchors 1390 and 1392 engage biological tissue disposed between them.

Figure 14:
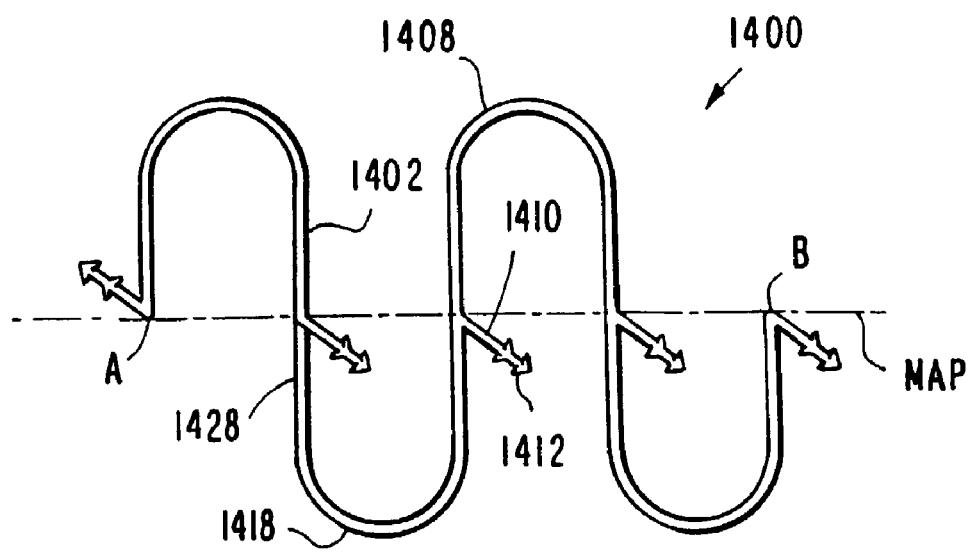
FIG. 14 is a perspective view of apparatus in accordance with the principles of the invention.

FIG. 14 shows illustrative open cell apparatus 1400 unrolled for the purpose of illustration. Apparatus 1400 may include band 1402. Band 1402 may include one or more upper lobes such as upper lobe 1408. Band 1402 may include one or more lower lobes such as lower lobe 1418. One or more anchors such as anchor 1410 may be present on band 1402. Anchor 1410 may be present on or near medial axial plane MAP. In some embodiments, band 1402 may have more lobes than are shown in FIG. 14. In some embodiments, band 1402 may have fewer lobes than are shown in FIG. 14. Double barbs 1412 may be present on anchor 1410. Some embodiments may include one or more anchors that include more than or less than two barbs.

Figure 14A:
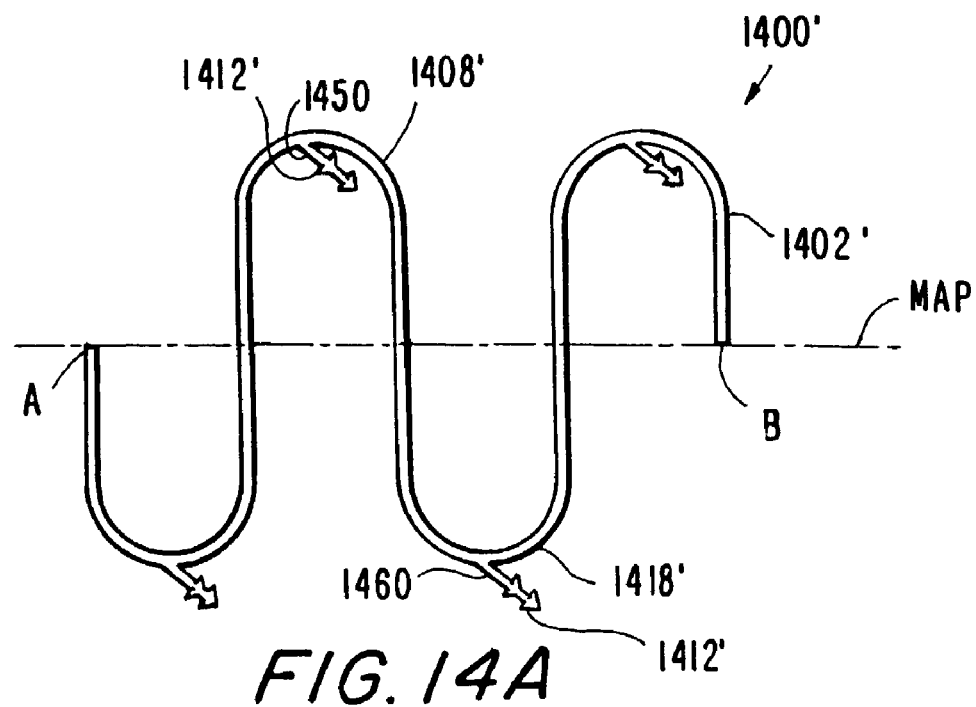
FIG. 14A is a perspective view of apparatus in accordance with the principles of the invention.

FIG. 14A shows illustrative open cell apparatus 1400' unrolled for the purpose of illustration. Apparatus 1400' may include band 1402'. Band 1402' may include one or more upper lobes such as upper lobe 1408'. Band 1402' may include one or more lower lobes such as lower lobe 1418'. One or more upper anchors such as upper anchor 1450 may be present on upper lobe 1408'. One or more lower anchors such as lower anchor 1460 may be present on lower lobe 1418'. In some embodiments, one or both of anchors 1450 and 1460 may not be present on medial axial plane MAP. In some embodiments, band 1402' may have more lobes than are shown in FIG. 14. In some embodiments, band 1402' may have fewer lobes than are shown in FIG. 14. Double barbs 1412' may be present on one or both of anchors 1450 and 1460. Some embodiments may include one or more anchors that include more than or less than two barbs.

FIG. 15 shows illustrative open cell apparatus that may include band 1502. Band 1502 is shown unrolled between ends A and B. Lobes such as upper lobe 1508 may include a rigid portion such as portion 1550. Lobes such as lower lobe 1518 may include a rigid portion such as portion 1560. One or more anchors such as anchors 1510 may be present on rigid portion 1550. One or more anchors such as anchors 1520 may be present on rigid portion 1560.

During expansion, flexible portions 1554 and 1556 may deform to allow connecting member 1528 to rotate in direction J. The deformation of portions 1554 and 1556 may allow lobes 1508 and 1518 to move away from each other along directions P and Q, respectively, without causing rigid portions 1550 and 1560 to migrate toward each other in directions X and Y (shown also in FIG. 12), respectively. The deformation of portions 1554 and 1556 may allow lobes 1508 and 1518 to move away from each other along directions P and Q, respectively, without causing anchors 1510 and 1520 to migrate toward each other in directions X and Y (shown also in FIG. 12), respectively.

During contraction, flexible portions 1554 and 1556 may deform to allow connecting member 1528 to rotate in direction K. The deformation of portions 1554 and 1556 may allow lobes 1508 and 1518 to move toward each other along directions Q and P, respectively, without causing rigid portions 1550 and 1560 to migrate away from each other in directions Y and X (shown also in FIG. 12), respectively. The deformation of portions 1554 and 1556 may allow lobes 1508 and 1518 to move toward each other along directions Q and P, respectively, without causing anchors 1510 and 1520 to migrate toward each other in directions Y and X (shown also in FIG. 12), respectively.

FIG. 15 shows rigid portions 1550 and 1560 shaped and sized to make them more rigid than flexible portions 1554 and 1556. Some embodiments of the invention may include rigid portions that are made of less pliant material than flexible portions 1554 and 1556. In some of those embodiments, rigid portions 1550 and 1560 and flexible portions 1554 and 1556 may have equivalent shapes or dimensions. For example, if a rigid portion includes material that is less elastic than a flexible portion, dimensions such as cross sections M and N shown in FIG. 15 for rigid portion 1550 and flexible portion 1554, respectively, may be made approximately the same. In some embodiments, rigid portions 1550 may be referred to as "nodes."

Any suitable mechanism for allowing a connecting member such as 1528 to reduce movement in directions X and Y when band 1502 expands or contracts may be used. For example, a connecting member may be a flexible coil coupled to rigid members 1550 and 1560. When band 1502 expands, the coil may expand. When band 1502 contracts, the coil may contract. Some embodiments of the invention may include a connecting member that has reciprocating elements that may cause the connecting member to lengthen or shorten in response to 20 band expansion and contraction, respectively. In some embodiments, connecting members 1528 may be referred to as "transition" members.

FIG. 15A shows apparatus 1500' that, in some embodiments, may be similar to apparatus 1500 (shown in FIG. 15) with the exception of the arrangement of anchors. Some or all of upper anchors 1510' may be present on band 1502' in or near axial plane AP1. Some or all of lower anchors 1520' may be present on band 1502' in or near axial plane AP2. Axial planes AP1 and AP2 may be positioned at any suitable axial positions.

Figure 16:
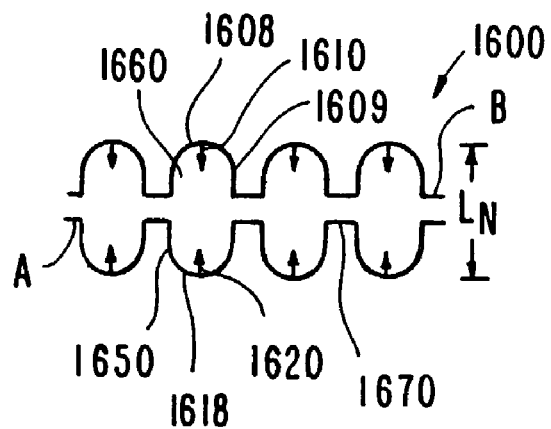
FIG. 16 is a schematic view of apparatus in accordance with the principles of the invention.

FIG. 16 shows illustrative band 1600 unrolled between ends A and B. Band 1600 may include one or more upper lobes such as upper lobe 1608. Band 1600 may include one or more lower lobes such as lower lobe 1618. One or more anchors such as anchor 1610 may be present on upper lobe 1608. One or more anchors such as anchor 1620 may be present on lower lobe 1618. Upper lobe 1608 may be directly opposite lower lobe 1618 to form a closed "cell" such as closed cell 1650. Closed cell 1650 may include opening 1660. The presence of closed cells is a feature that may be referred to as "closed cell" design. Any suitable number of closed cells may be present in band 1600.

Figure 17:
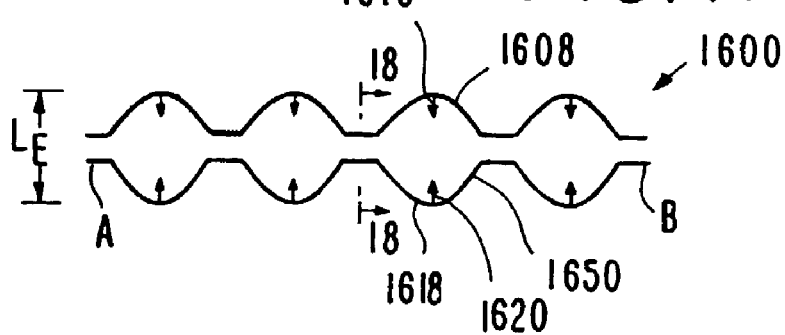
FIG. 17 is a schematic view of apparatus in accordance with the principles of the invention.

FIG. 17 shows band 1600 in an expanded state. Band 1600 has been radially expanded (in direction R as shown in FIG. 12). Axial spread $L_E$ of band 1600 in the expanded state is less than axial spread $L_N$ (shown in FIG. 16) of band 16 in the normal state.

Figure 18:
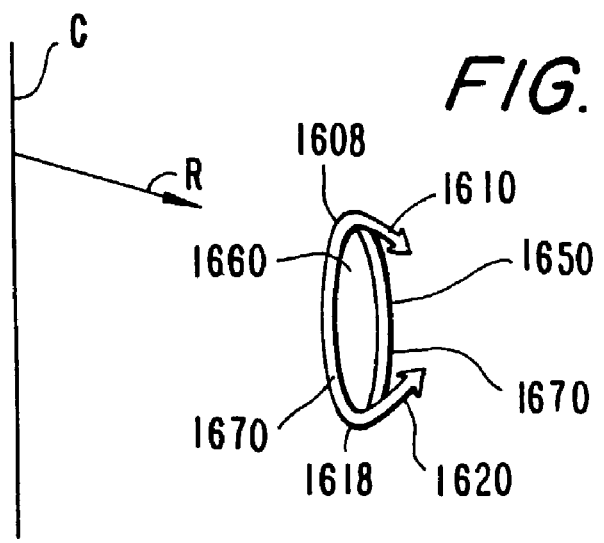
FIG. 18 is a perspective view of apparatus in accordance with the principles of the invention.

FIG. 18 shows one of closed cells 1650 as viewed from line 18—18 in FIG. 17. Closed cell 1650 may include upper lobe 1608 and lower lobe 1618. One or more anchors such as anchor 1610 may be present on upper lobe 1608. One or more anchors such as anchor 1620 may be present on lower lobe 1618. One or more anchors on closed cell 1650 may extend away from axis C in a direction that has a component parallel to the direction R (also shown in FIG. 12). One or more anchors on closed cell 1650 may extend away from axis C in a direction that has a component parallel to axis C.

Figure 19:
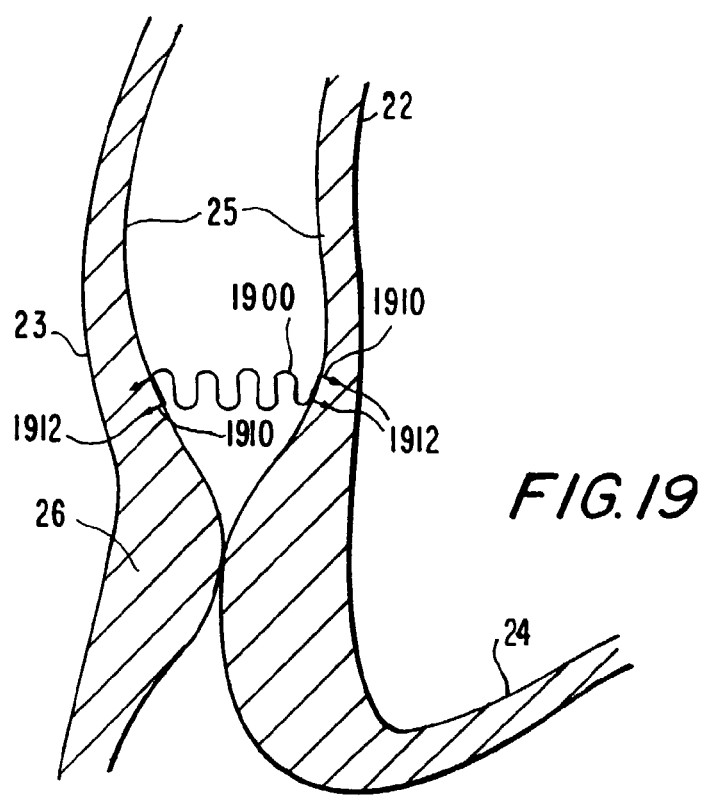
FIG. 19 is a schematic view of apparatus in accordance with the principles of the invention disposed in the passage shown in FIG. 2.

FIG. 19 shows (schematically) illustrative open cell device 1900 deployed in distal esophagus 23 above LES 26. Anchors 1910, which may include barbs 1912, are engaged with distal esophagus 23. Any suitable number of anchors 1910 may be present on device 1900. Any suitable type or types of anchors may be present on band 1900. Anchors may be located on any suitable portion of device 1900.

Figure 20:
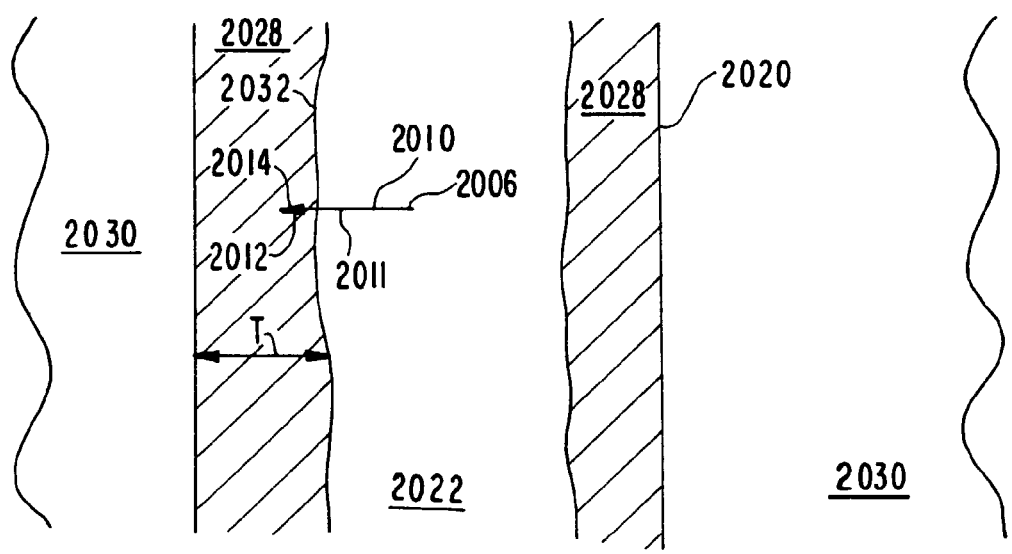
FIG. 20 is a schematic view of an apparatus in accordance with the principles of the invention disposed in a biological passage.

FIGS. 20–23 show illustrative examples of the placement of anchors accordance with the principles of the invention. FIG. 20 shows anchor 2010 present in biological tubing 2020 passing through body cavity 2030. Anchor 2010 may be referred to as a "dart." Anchor 2010 may include stem 2011 in lumen 2022 and head 2014 embedded in wall 2028. Base 2006 may be attached to apparatus for reducing the diameter of tubing 2020. One or more barbs such as 2012 may secure head 2014 in the tissue of wall 2028. Head 2014 may be embedded anywhere along thickness T of wall 2028.

In some embodiments, head 2014 may be positioned in wall 2028 near inner face 2032 to avoid applying stress to the portion of wall 2028 near outer surface 2036 when anchor 2110 is drawn toward lumen 2022. In some embodiments, head 2014 may be positioned in wall 2028 near outer surface 2036 to enable head 2014 to be supported by a large portion of the tissue of wall 2028 when anchor 2110 is drawn toward lumen 2022.

Figure 21:
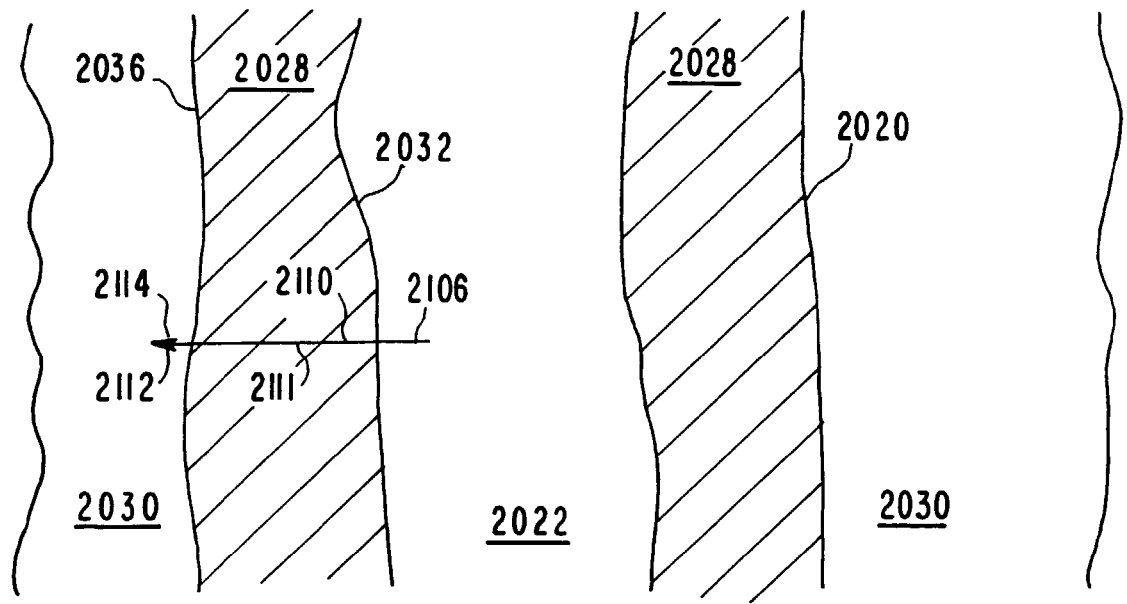
FIG. 21 is a schematic view of an apparatus in accordance with the principles of the invention disposed in the biological passage shown in FIG. 20.

FIG. 21 shows anchor 2110 partially present in tubing 2020 that may be present in body cavity 2030. Anchor 2110 may include stem 2111 passing through wall 2028 and head 2114 that may be present in cavity 2030. Head 2114 may have been pushed through wall 2028 into cavity 2030. One or more barbs such as 2112 may engage outer wall 2036 of tubing 2020 to prevent anchor 2110 from withdrawing from wall 2028 and passing back toward lumen 2022. Base 2106 may be coupled to apparatus for reducing the diameter of tubing 2020. Base 2106 may be coupled to apparatus for reducing the diameter of lumen 2022.

Figure 22:
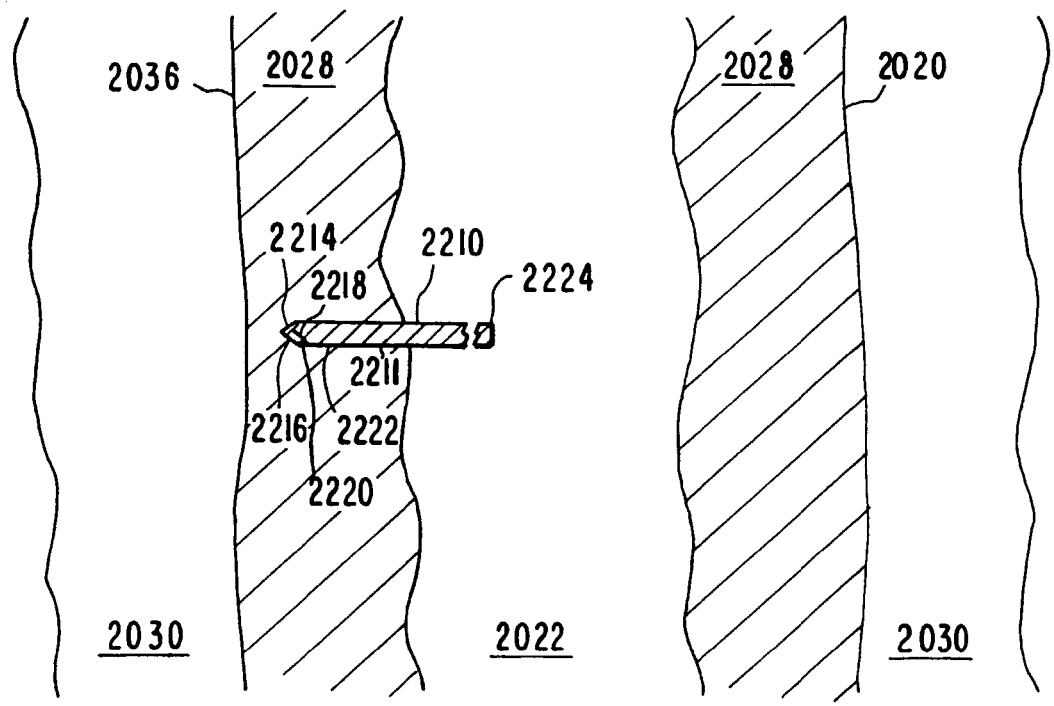
FIG. 22 is a sectional view of an apparatus in accordance with the principles of the invention disposed in the biological passage shown in FIG. 20.

FIG. 22 shows anchor 2210 present in tubing 2020 passing through body cavity 2030. Anchor 2210, which may at least partially pass through wall 2028, may include stem 2211 and head 2214. Head 2214 may include flexible portion 2216. Flexible portion 2216, which may be a skived portion, may rest against anchor surface 2218 when head 2214 is present in wall 2028. In some embodiments, surface 2220 of flexible portion 2216 may align flush or nearly flush with surface 2222 of stem 2211. Interior portion 2224 may be coupled to apparatus for reducing the diameter of lumen 2022.

Figure 22A:
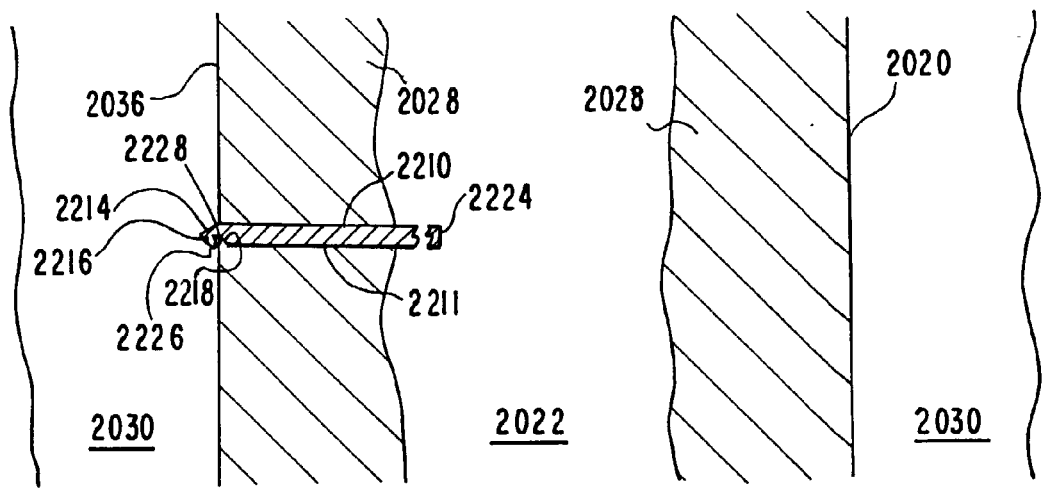
FIG. 22A is a sectional view of the apparatus shown in FIG. 22, disposed in the biological passage shown in FIG. 20, in a different stage of operation.

FIG. 22A shows anchor 2210 at a later stage of insertion in wall 2028 than that shown in FIG. 22. Head 2214 may have advanced through outer face 2036 of wall 2028 and be at least partially disposed in body cavity 2030. Flexible portion 2216, which may be biased away from surface 2218, may move away from surface 2218 of stem 2211. Tip 2226 may move away from stem 2211. Tip 2226 may engage surface 2036 to prevent anchor 2210 from moving toward lumen 2022. Surface 2228 may separate from surface 2218. Surface 2228 may engage or partially engage surface 2036 to prevent anchor 2210 from moving toward lumen 2022.

Figure 23:
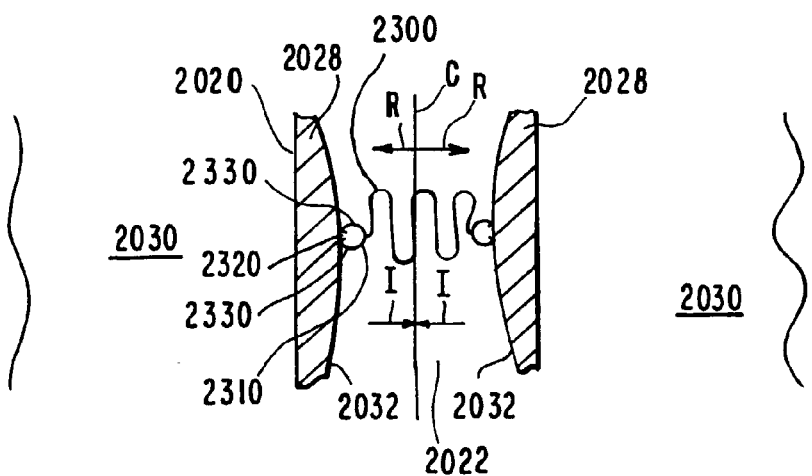
FIG. 23 is a schematic view of apparatus in accordance with the principles of the invention disposed in the biological passage shown in FIG. 20.

FIGS. 23–34 show features of some embodiments of the invention that may involve attaching a band to biological tubing using crimping technology. FIG. 23 shows open cell device 2300 present in lumen 2022 of biological tubing 2020. Device 2300 may be expanded outwardly away from axis C in radial direction R. Device 2300 may be contracted toward axis C in radial direction I. Device 2300 may include on or more crimpable anchors such as anchor 2310, which may have prongs 2330. In some embodiments of the invention, a crimpable anchor may be a staple. Anchor 2310 may be C-shaped. Anchor 2310 may be U-shaped. Anchor 2310 may be used in conjunction with one or more dart anchors. Anchor 2310 may include one or more barbs such as barb 2320 for engaging tissue. FIG. 23 shows anchors 2310 positioned near (or in contact with) inner face 2032 of wall 2028.

Figure 24:
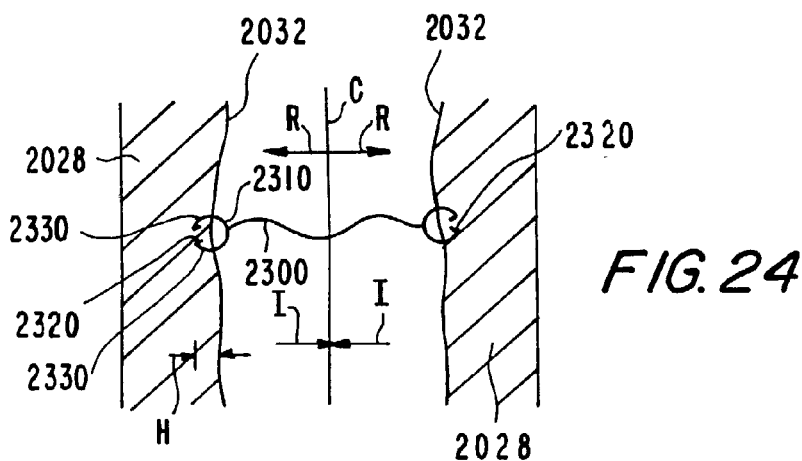
FIG. 24 is a schematic view of apparatus in accordance with the principles of the invention disposed in the biological passage shown in FIG. 20.

FIG. 24 shows device 2300 expanded in direction R relative to the state shown in FIG. 23. Prongs 2330 have at least partially penetrated through inner face 2032 into the tissue of wall 2028. One of prongs 2330 is shown to have penetrated wall 2028 to depth H. In some embodiments, the maximum value of H may be limited by the shape of anchor 2310. In some embodiments, the maximum value of H may be limited by the length of prongs 2330. Barbs 2320 may prevent prongs 2330 from pulling out of wall 2028 when band 2300 is allowed to contract along inner radial direction I toward axis C.

Figure 25:
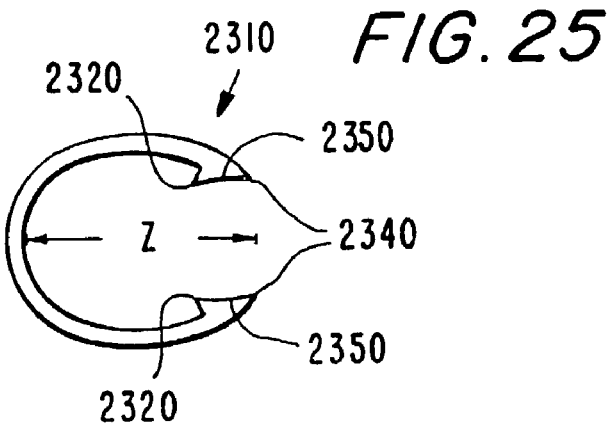
FIG. 25 is a sectional view of an apparatus in accordance with the principles of the invention.

FIG. 25 shows open anchor 2310 which may have maximum penetration depth Z. Anchor 2310 may have one or more sharpened points such as 2340. Anchor 2310 may have one or more sharpened edges such as 2350. Anchor 2310 may have one or more barbs such as 2320.

Figure 26:
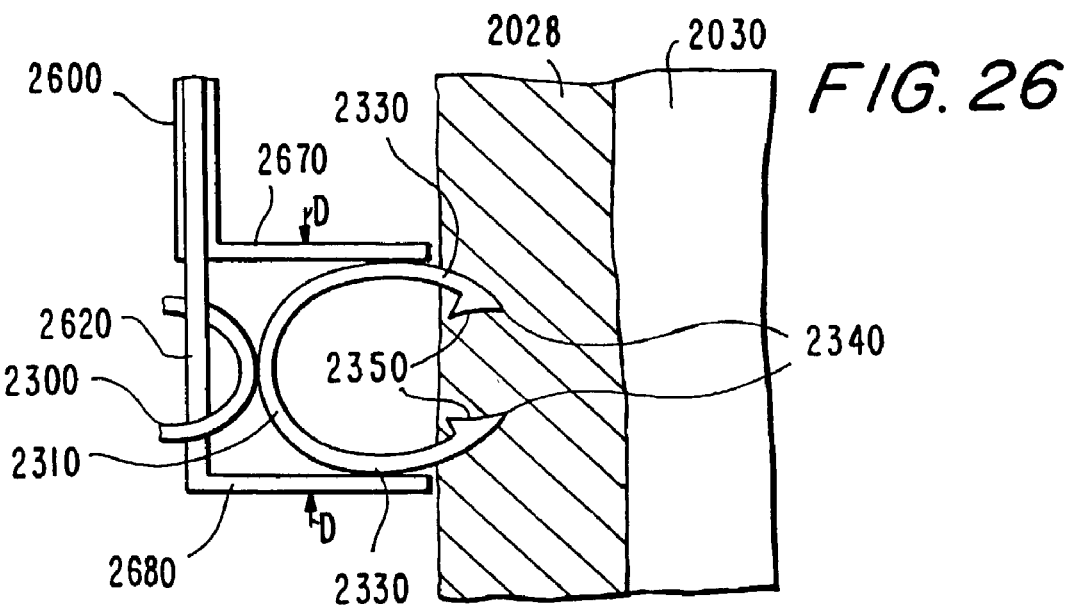
FIG. 26 is a partial sectional view of apparatus in accordance with the principles of the invention disposed in a portion of the biological passage shown in FIG. 20.

FIG. 26 shows illustrative crimping tool 2600 which may be used to crimp anchor 2310. Tool 2600 may be inserted into lumen 2022. Elongated portion 2620 may be extended distally past a portion of device 2300 to support crimping member 2680. Crimping member 2670 may be positioned proximally of a portion of device 2300. Crimping members 2670 and 2680 may be drawn together in directions D against prongs 2330 of anchor 2310. Crimping members 2670 and 2680 may force sharp points 2340 into tissue of wall 2028. Sharp edges 2350 may cut tissue of wall 2028 as prongs 2330 penetrate.

Figure 27:
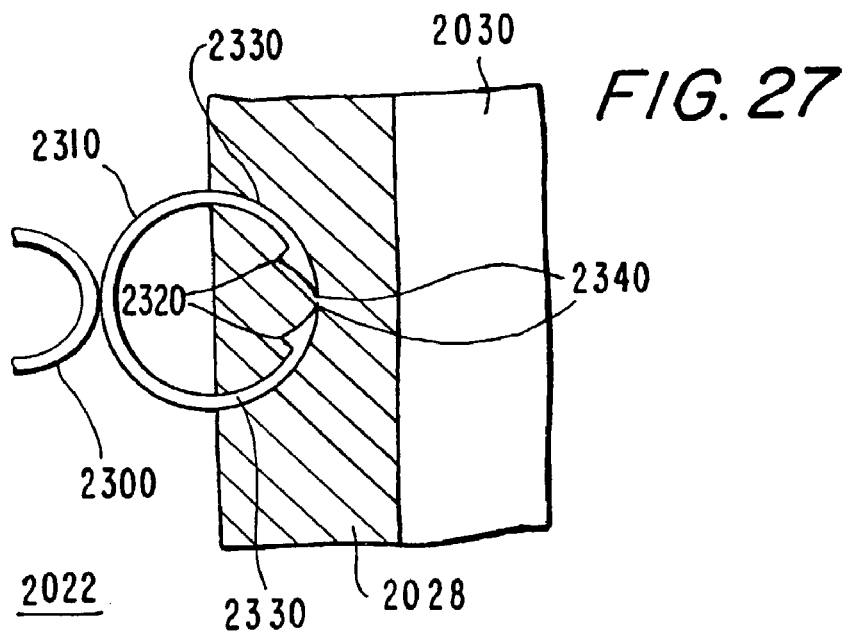
FIG. 27 is a partial sectional view of apparatus in accordance with the principles of the invention disposed in a portion of the biological passage shown in FIG. 20.

FIG. 27 shows anchor 2310 secured in the tissue of wall 2028 after crimping by tool 2600. Prongs 2330 are at least partially inserted in wall 2028. Prongs 2330 may be held in place by barbs 2320. Prongs 2330 may be held in place by the closure of anchor 2310 by tool 2600. Sharp points 2340 may be drawn toward each other as anchor 2310 is closed. Device 2300 in lumen 2022 may be used to pull wall 2028 toward the central portion of lumen 2022.

Figure 28:
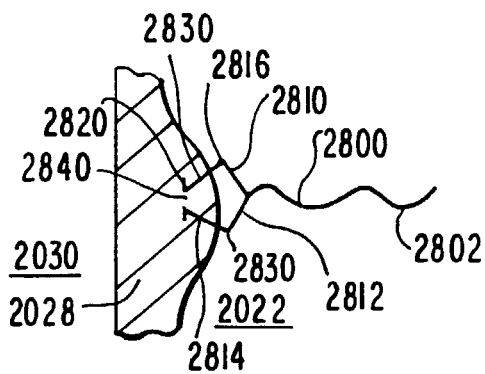
FIG. 28 is a schematic view of apparatus in accordance with the principles of the invention disposed in the biological passage shown in FIG. 20.
Figure 29:
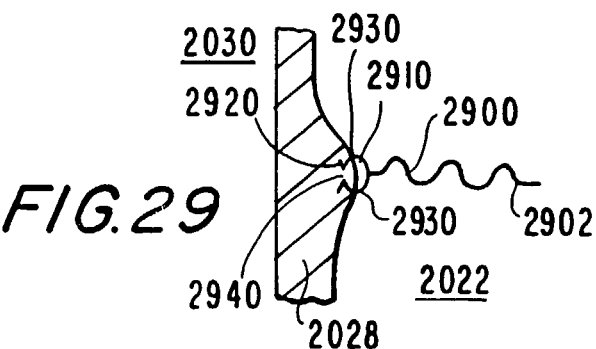
FIG. 29 is a schematic view of apparatus in accordance with the principles of the invention disposed in the biological passage shown in FIG. 20.

FIGS. 28 and 29 show illustrative embodiments of crimpable anchors. FIG. 28 shows device 2800 in lumen 2022. Device 2800 may include band 2802. Band 2802 may include crimpable anchor 2810. Anchor 2810 may have one or more prongs such as 2830. Prong 2830 may have one or more elongated members such as 2812 and 2814. Elongated members 2812 and 2814 may be coupled at angled junction 2816. One or more barbs such as barb 2820 may be present on prong 2830 to engage tissue of wall 2028. Barbs 2820 extend away from interior region 2840 of anchor 2810. In some embodiments, one or more barbs may extend toward the central portion of lumen 2022. In some embodiments, both internally directed and externally directed (i.e., away from region 2840) barbs may be present.

FIG. 29 shows device 2900 in lumen 2022. Device 2900 may include band 2902. Device 2900 may include crimpable anchor 2910. Anchor 2910 may have one or more curved prongs such as 2930. One or more barbs such as barb 2920 may be present on prong 2930 to engage tissue of wall 2028. Barbs 2820 extend away from interior region 2940 of anchor 2910. In some embodiments, one or more barbs may extend toward interior region 2940. In some embodiments, both internally directed and externally directed barbs may be present.

Figure 32:
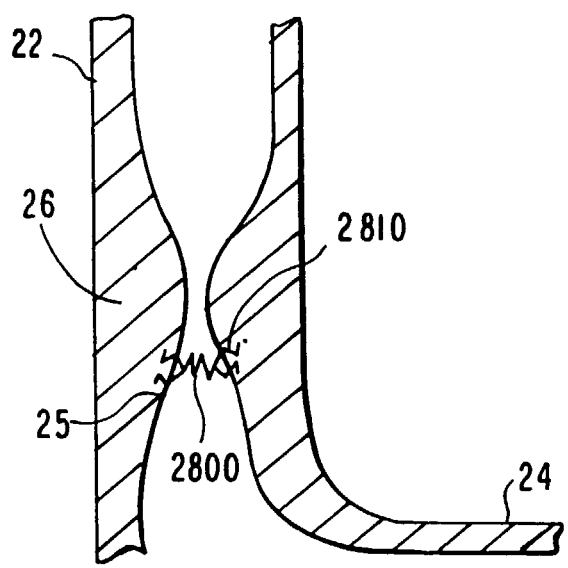
FIG. 32 is a schematic view of apparatus in accordance with the principles of the invention disposed in the biological passage shown in FIG. 20.
Figure 30:
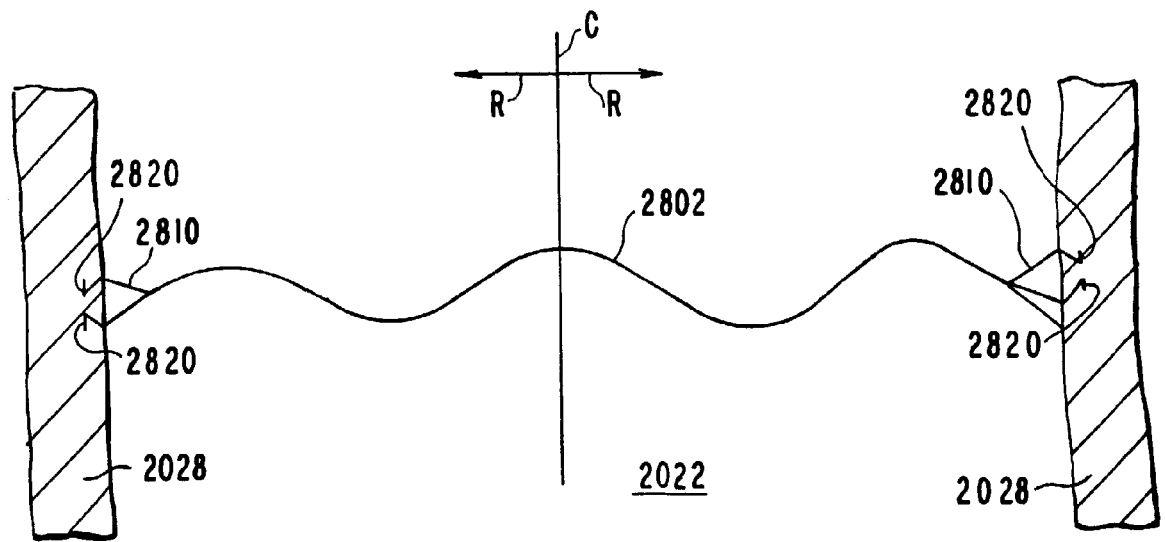
FIG. 30 is a schematic view of apparatus in accordance with the principles of the invention disposed in the biological passage shown in FIG. 20.
Figure 31:
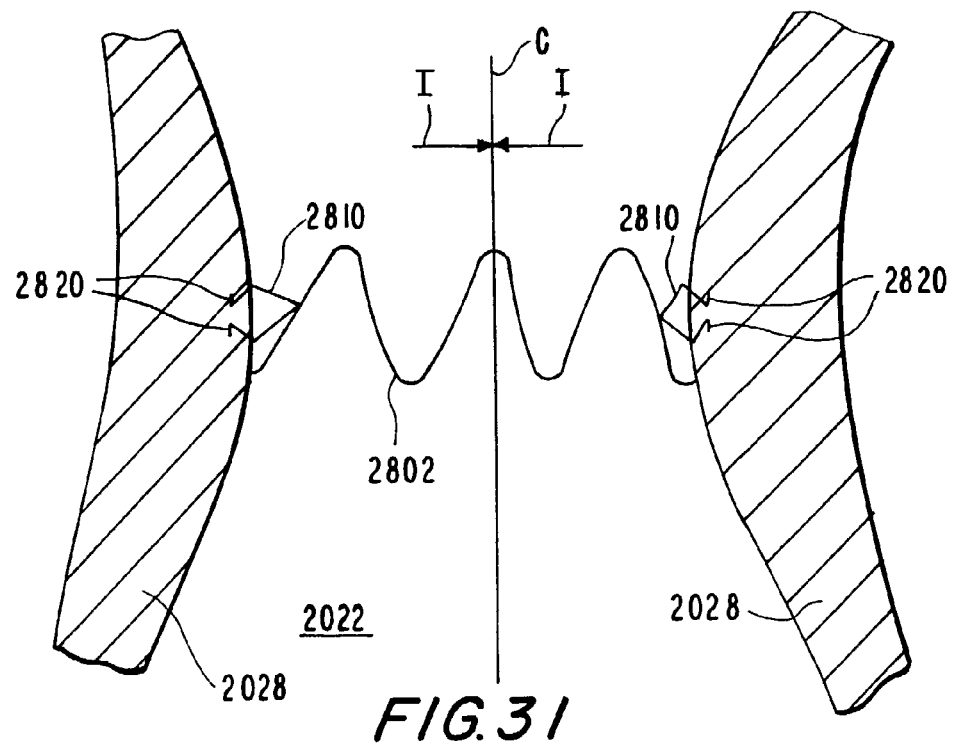
FIG. 31 is a schematic view of apparatus in accordance with the principles of the invention disposed in the biological passage shown in FIG. 20.

FIG. 30 shows band 2802 in lumen 2022 expanded away from axis C in direction R. Band 2800 may be expanded by dilation of a balloon (not shown). Anchors 2810 may be crimped, for example using tool 2600, into portions of wall 2028. FIG. 31 shows wall 2028 drawn in direction I toward axis C by band 2800 after band 2802 is allowed to contract. Barbs 2820 may prevent anchors 2810 from pulling out of wall 2028. FIG. 32 shows band 2802 deployed below and supporting LES 26 in esophagus 22 above stomach 24.

Figure 33:
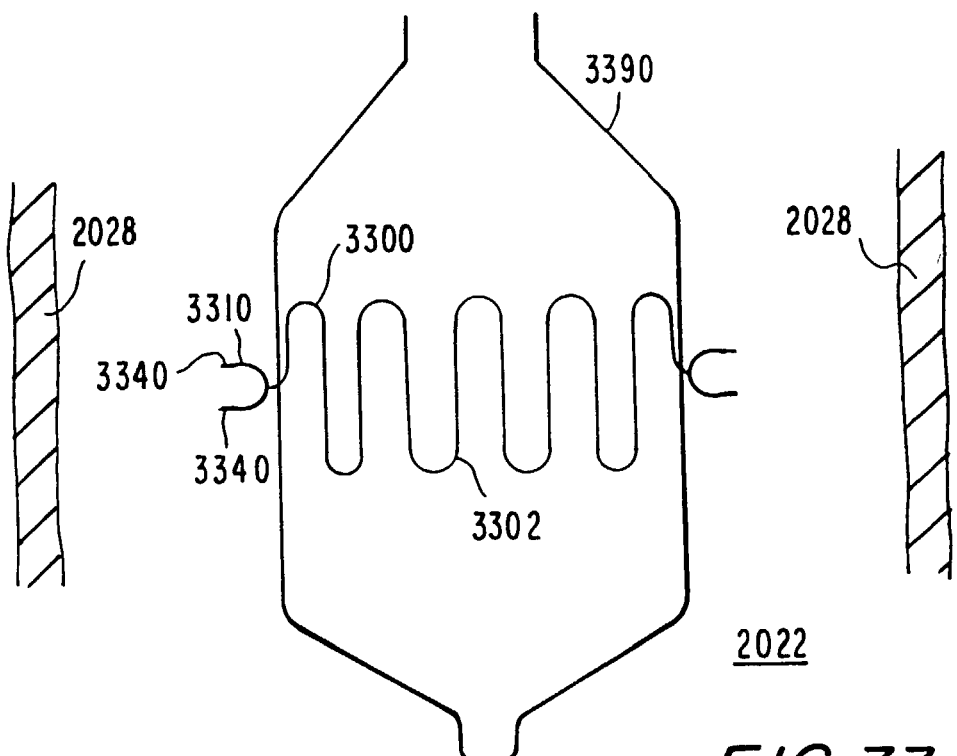
FIG. 33 is a schematic view of apparatus in accordance with the principles of the invention disposed in the biological passage shown in FIG. 20.
Figure 34:
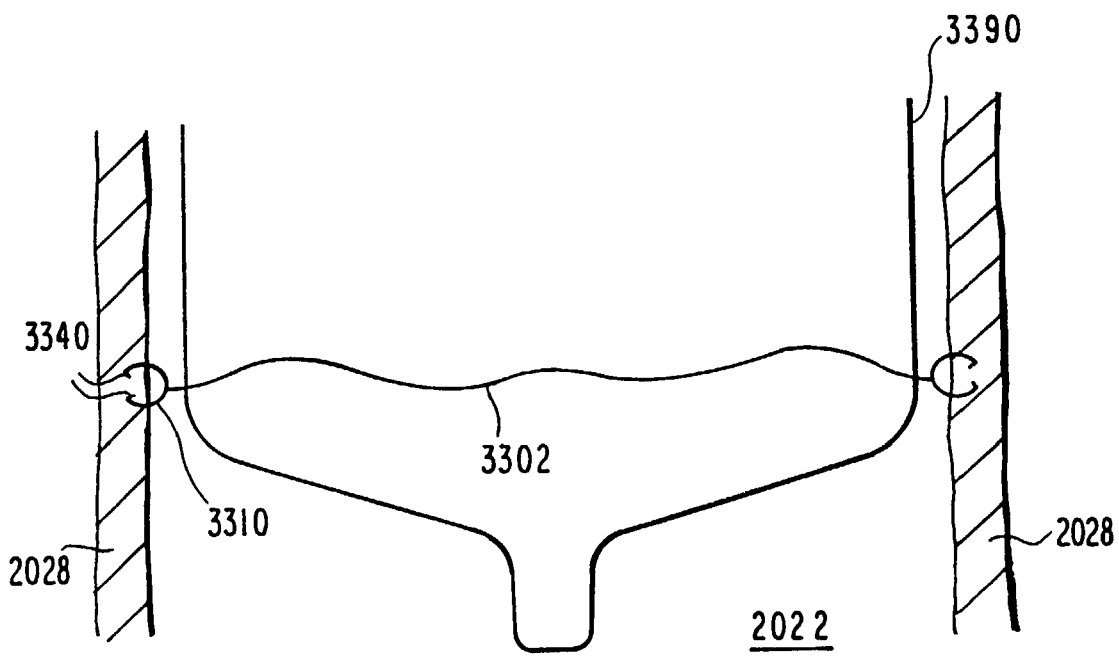
FIG. 34 is a schematic view of apparatus in accordance with the principles of the invention disposed in the biological passage shown in FIG. 20.
Figure 35:
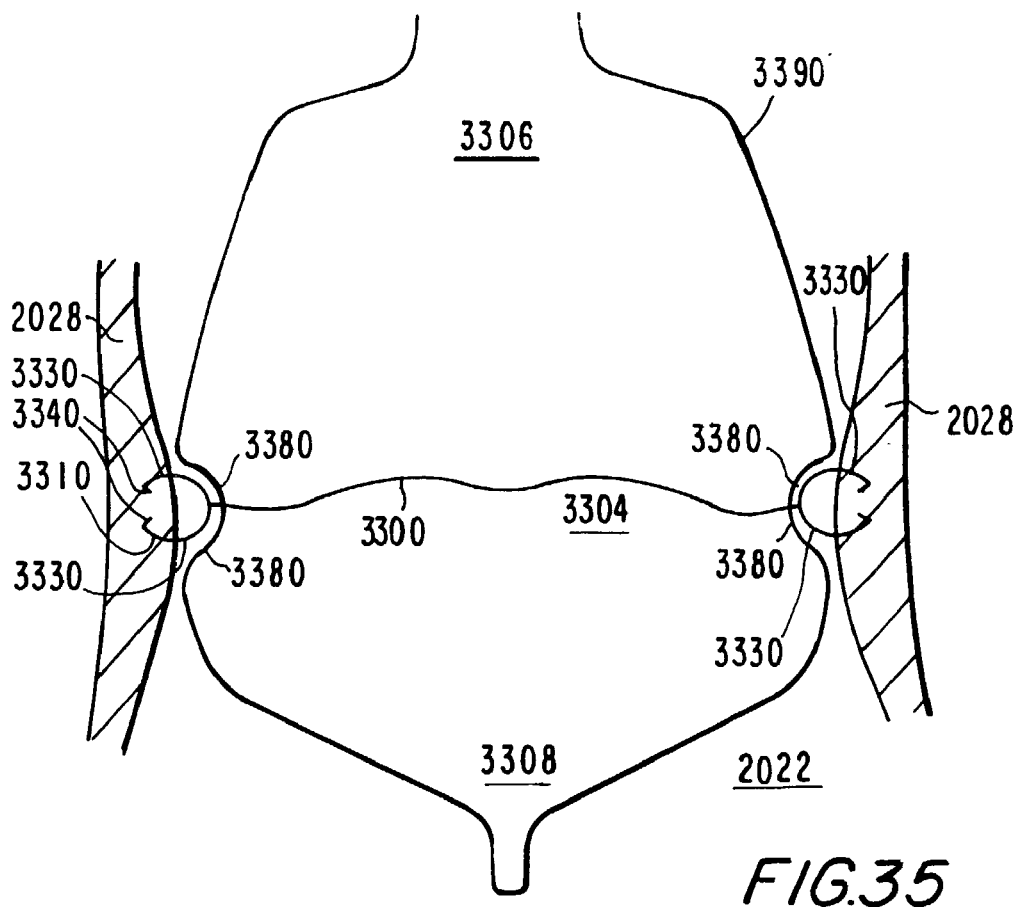
FIG. 35 is a schematic view of apparatus in accordance with the principles of the invention disposed in the biological passage shown in FIG. 20.

FIGS. 33–35 illustrate embodiments of the invention that may include balloon-actuated anchor crimping. Although illustrated in relation to open cell device 3300 and anchor 3310, any suitable type of band and any suitable type of anchor or anchors, including band types and anchor types described and illustrated herein, may be used for balloon-actuated crimping. FIG. 33 shows device 3300 in lumen 2022. Device 3300 may include band 3302. Device 3300 may include one or more crimpable anchors such as anchor 3310. For clarity, only two anchors are shown in FIG. 33, but other anchors may be present in device 3300. Anchor 3310 may include sharp points 3340 for penetrating wall 2028. Balloon 3302 may be neutrally inflated within device 3300, for example, with sufficient pressure to retain device 3300 and position band 3302 at a selected location in lumen 2202.

FIG. 34 shows that in some embodiments of the invention, balloon 3390 may be dilated within band 3302 to drive anchors 3310 into wall 2028. In some of those embodiments, balloon 3390 may drive anchor 3310 into wall 2028 when the pressure inside balloon 3390 is about 10 atmospheres above the ambient pressure in lumen 2202. In some embodiments, dilation sufficient to cause sharp points 3340 to penetrate wall 2028 may be a first stage of dilation of balloon 3390.

FIG. 35 shows that balloon 3390 may be dilated to a state greater than that shown in FIG. 34. This stage may be a second dilation stage. In the second dilation stage, anchor 3310 may be crimped by balloon 3390 to secure anchors 3310 in wall 2028. In the second dilation stage, balloon 3390 may have an internal pressure about 20 atmospheres greater than the pressure external to balloon 3390 in lumen 2022.

Balloon 3390 may include regions of variable compliance. For example, central region 3304 of balloon 3390 may have a first compliance, proximal region 3306 may have a second compliance, and distal region 3308 may have a third compliance. In some embodiments, regions 3306 and 3308 may have approximately the same compliance. In some of those embodiments, region 3304 may have a compliance that is less than the compliance of regions 3306 and 3308.

In some embodiments, balloon 3390 may include central region 3304 having a compliance greater than the compliance of regions 3306 and 3308. In those embodiments, as balloon 3390 is dilated in the second dilation stage, regions 3306 and 3308 may expand more than central region 3304. Some embodiments may include balloon portions 3380, which may be near the transitions between regions of different compliances. Portions 3380 may apply force to anchor 3310 to crimp anchor 3310 into a secure configuration. Anchor 3310 may be permanently secured, or locked, into wall 2028.

In some embodiments, the force applied by portions 3380 may have a component that is parallel to the axial direction of lumen 2022. The axial force component may cause anchor 3310 to close. FIG. 35 shows sharp points 3340 of anchor 3310 in close proximity to each other.

In some embodiments, balloon 3390 may have a uniform compliance. In some of those embodiments, anchor 3310 may be crimped by balloon dilation. For example, the size of band 3302 may be chosen so that when band 3302 is maximally expanded, anchor 3310 is partially engaged in wall 2028. As balloon 3390 continues to dilate, regions 3380 may expand "around" and apply an axial crimping force to anchor 3310 as described above.

In some embodiments of the invention, band 3302 may have compound compliance. A first compliance may dominate when band 3302 is expanded toward wall 2028 and when anchor 3310 is partially engaged in wall 2028. A second compliance may dominate when anchor 3310 are crimped. The second compliance may be less than the first compliance to "bind" balloon 3390 to cause portions 3380 to generate axial forces on anchors 3310.

In some embodiments, anchor 3310 may be self-crimping. For example, balloon 3390, which in self-crimping embodiments may have compound or uniform compliance, may push anchor 3310 radially away from the center of lumen 2022 into wall 2028. The curvature of prongs 3330 (or, in the case of angled prongs like 2830, the angle of the prongs) may be selected to cause anchor 3310 to close in response to being radially driven into wall 2028.

Figure 36:
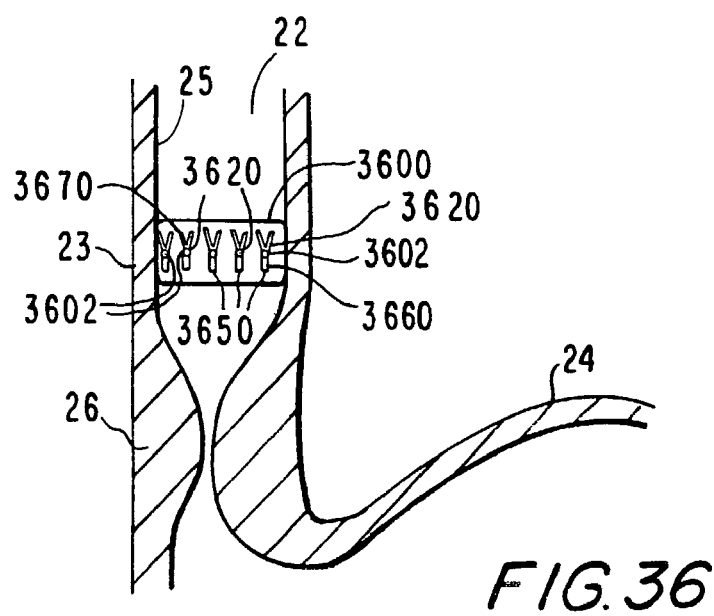
FIG. 36 is an elevational view of apparatus in accordance with the principles of the invention disposed in the biological passage shown in FIG. 2.

FIGS. 36–38 show features of embodiments of the invention that may involve clipping, pinning, suturing, or otherwise fastening a band to an inner wall of a portion of biological tubing. FIG. 36 shows band 3600 positioned in lower esophagus 23 above LES 26 and stomach 24. Tissue 3602 from wall 25 of esophagus 22 may be present in or emerging from openings 3620 in band 3600. (In FIG. 36, wall 25 is shown spanning esophagus 22 from left to right behind band 3600. Only the portion of band 3600 adjacent that portion of the wall is shown in FIG. 36.) Clips 3650 may be attached to portions of tissue 3602 to prevent the portions from receding back through the holes. Clips 3650 are shown having vertices 3660 positioned distally with respect to open ends 3670, but any suitable orientation of clips 3650 may be used. In some embodiments, tissue 3620 may be pinned or sutured to band 3600, or may be made secure by any combination of methods, which may include clipping.

In some embodiments of the invention, tissue 3602 may intrude through openings 3620 after band 3600 is attached to wall 25 using anchors (not shown). Band 3600 may be allowed to contract toward the central region of esophagus 22 and tissue 3602 may be forced through openings 3620 when the diameter of wall 25 is reduced by the pulling-in action of band 3600. Band 3600 is a type of closed cell band. Although a closed cell band is used to illustrate the clipping feature of some embodiments of the invention, the clipping feature may be present in embodiments of the invention involving any suitable type of band.

FIG. 37 shows tissue 3620 from wall 25 of esophagus 22 compressed through an opening in band 3600. Tissue 3620 may be held in place in the lumen of esophagus 22 (in the interior of band 3600) by clip 3650 which may include vertex 3660 and open end 3670. Clip 3650 may be made from spring metal, ductile metal, polymer, or any other suitable material. Clip 3650 may include one or more barbs to secure clip 3650 to tissue 3620. Although clip 3650 is a "V"-chip, any suitable form of clip may be used.

FIG. 38 shows clip 3650 seated in clip fastening device 3800. Stem 3830 may be inserted in biological tubing in which a band is to be secured. Clip 3650 seated between arms 3820 may be positioned around a portion of tissue to be secured (such as tissue 3620 shown in FIG. 37). Arms 3820 may be rotated about pins 3840. Arms 3820 may be actuated by one or more actuating members (not shown) present in or near stem 3830. In some embodiments, one arm may be fixed and the other arm may be actuated. Arms 3820 may be drawn together to compress clip 3650 into tissue 3620 (shown in FIG. 37). Device 3800 may be withdrawn from esophagus 22 to leave clip 3650 secured to tissue 3620.

FIG. 39 shows illustrative apparatus 3900 that may be used to reduce the diameter of a portion of biological tubing. In some embodiments of the invention, one or more apparatus such as apparatus 3900 may be deployed in a biological passage. In those embodiments, apparatus of different sizes or elastic properties may be used to provide different amounts of support to different parts of the passage. Apparatus 3900 may have a neutral state having a neutral diameter. Apparatus 3900 may be compressed to a state in which the diameter is less than that in the neutral state to facilitate the insertion of apparatus 3900 in a portion of body tubing.

Apparatus 3900 may by expandable radially away from axis C to an expanded state. From the expanded state, apparatus 3900 may automatically retract toward the neutral state. In some embodiments, apparatus 3900 may include an elastic material. In some of those embodiments, apparatus 3900 may include a polymer.

Apparatus 3900 may be inserted in a portion of tubing and expanded in direction R away from central axis C to engage one or more anchors such as anchor 3910 in the tubing wall. Anchor head 3914 may penetrate the wall. Apparatus 3900 may then be allowed to contract in direction I toward axis C. The contraction of apparatus 3900 may pull the tubing wall toward axis C and reduce the diameter of the tubing. Edge (or "catch") 3912 may engage wall tissue and prevent anchor 3914 from withdrawing from the wall during the contraction. Edge 3912 may prevent anchor 3914 from withdrawing from the wall after contraction.

Anchor 3910 may have one or more anchor heads such as head 3914. Anchor head 3914 may be coupled to stem 3920. In some embodiments, stem 3920 may extend radially away from axis C. In some embodiments, stem 3920 may extend away from axis C in a direction that has a non-radial component. In some of those embodiments, numerous stems curving away from band 3902 may be present to permit apparatus 3900 to be installed in the wall by rotating apparatus 3900 about axis C. For example, stem 3920 may curve away from band 3902 in an axial plane. In some embodiments, stem 3920 may extend away from band 3902 in a direction that is oblique with respect to both axis C and radial direction R. In some embodiments, stem 3920 may curve away from band 3902 in directions that are oblique with respect to both axis C and radial direction R.

Stem 3920 may be coupled to base 3930. Base 3930 may be embedded in band 3902 of apparatus 3900. In some embodiments, band 3902 may be formed from a moldable material such as a flexible polymer. In some of those embodiments, anchor 3910 may be at least partially insert molded into band 3902. Base 3930 may be inserted in band 3902 before band 3902 is solidified. Stem 3920 may be allowed to protrude out of band 3920 to expose head 3914. In some embodiments, one or more anchors may be attached to band 3902 after band 3902 is solidified.

In some embodiments, band 3902 may be of uniform material properties. In some embodiments, band 3902 may include regions of different material properties. For example, band 3902 may include sections such as 3940 and 3950. Section 3940 may be less flexible than section 3950. Section 3940 may be less elastic than section 3950. Anchor 3910 may be embedded in or otherwise supported by a section or sections such as 3940. A section or sections such as 3950 may be free from anchors. In embodiments in which anchor 3910 is embedded in or otherwise supported by a section such as 3940, stress concentration near anchor 3910 may be less than in embodiments in which anchor 3910 is embedded or otherwise supported by a section such as 3950. In some embodiments, sections 3940 and 3950 may be formed in different molding stages and bonded together, for example at bond 3960, after at least one has already at least partially solidified.

Figure 40:
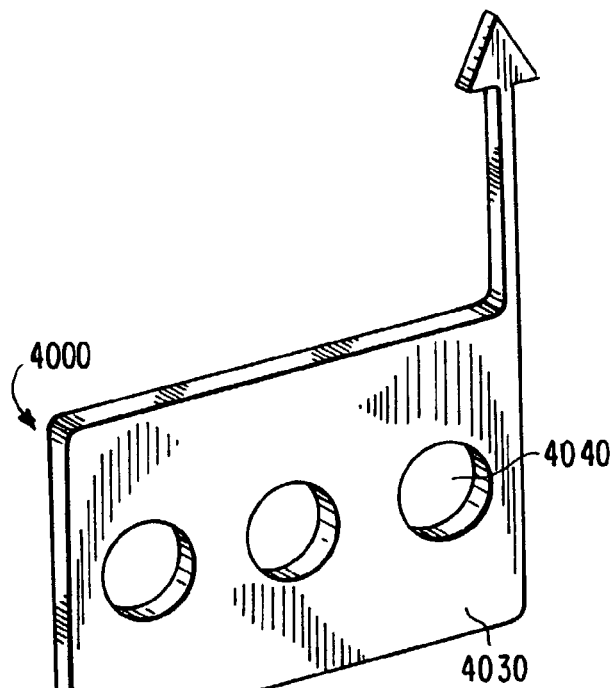
FIG. 40 is a perspective view of an apparatus in accordance with the principles of the invention.

FIG. 40 shows a preliminary formation stage of illustrative anchor 4000 that may be used in conjunction with some embodiments of the invention. Anchor 4000 may be cut or punched from a sheet of material. The sheet may include metal, rigid polymer, or any other suitable material. Anchor 4000 may include one or more stems such as 4020. Stem 4020 may support anchor head 4014, which may include edge 4012. Holes such as hole 4040 may be provided to receive molding material during the formation of a band such as 3902 shown in FIG. 39. In some embodiments of the invention, hole 4040 may not be present.

Figure 41:
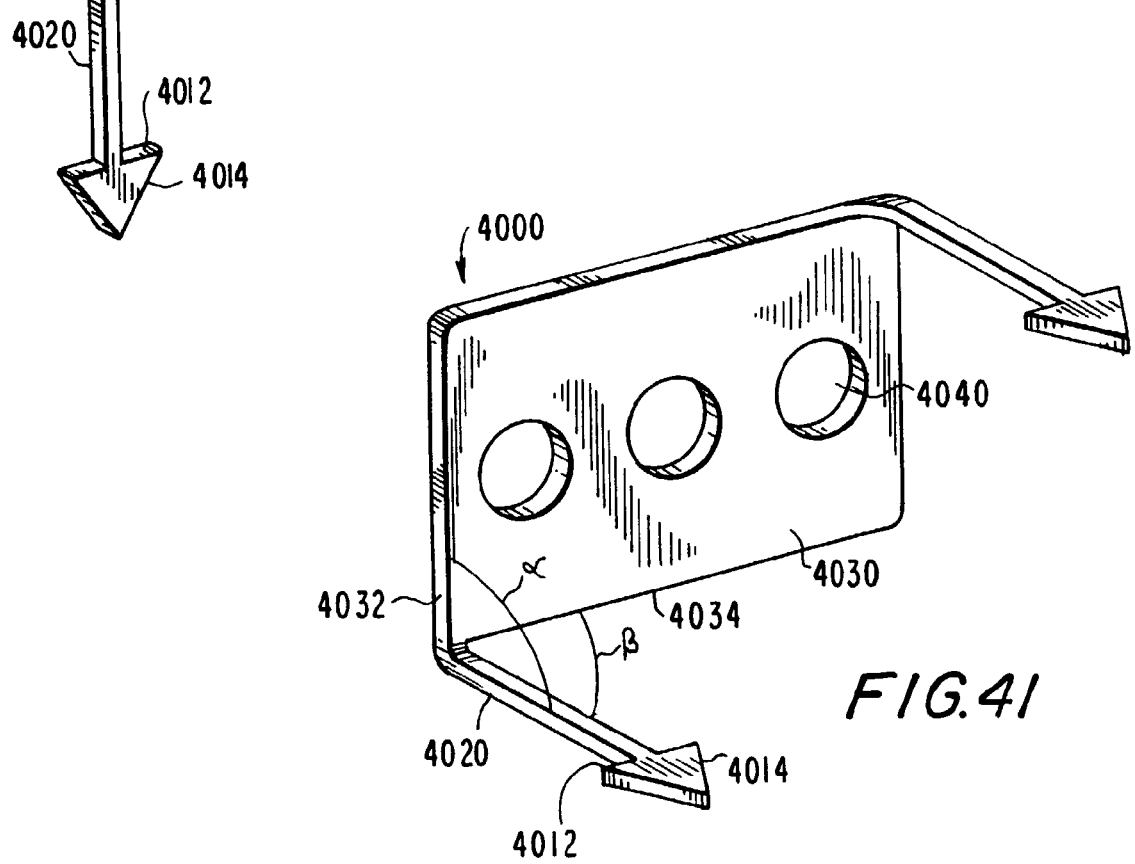
FIG. 41 is a perspective view of an apparatus in accordance with the principles of the invention.

FIG. 41 shows a stage of formation of anchor 4000 that is later than that shown in FIG. 40. FIG. 41 shows stems such as stem 4020 bent to angle α with respect to edge 4032 of base 4030. Angle α may be 90° or any other suitable angle. Stem 4020 may be positioned at angle β with respect to edge 4034 of base 4030. Angle β may be 90° or any other suitable angle. Stem 4020 may curve away from base 4034 in any suitable manner. Anchor 4000 may include different stems that are positioned at different angles with respect to base 4030. In some embodiments, stem 4020 may extend in a curved manner away from base 4030.

Figure 42:
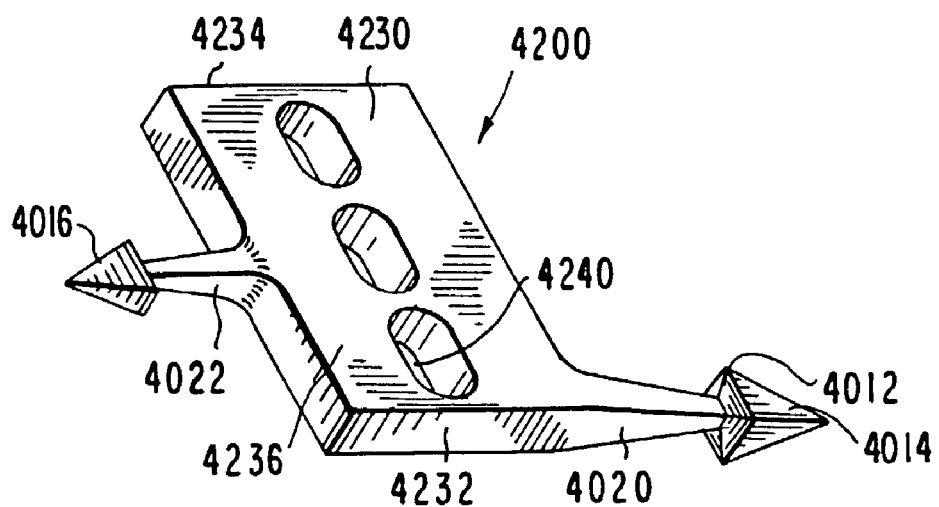
FIG. 42 is a perspective view of an apparatus in accordance with the principles of the invention.

FIG. 42 shows a preliminary formation stage of illustrative anchor 4200 that may be used in conjunction with some embodiments of the invention. Anchor 4200 may include one or more stems such as stem 4022 coupled to base 4230 between edges 4232 and 4234 of base 4230. In some embodiments, stem 4022 may be tapered to narrow toward head 4016. Some embodiments may include stem 4020 extending from edge 4232 of base 4230. Stem 4020 may become more narrow toward head 4014. Edge 4012 may be present on head 4014 to prevent anchor 4200 from withdrawing from tissue. In some embodiments, edge 4012 may be continuous around the perimeter of stem 4020. At a later stage of formation, one or more of stems 4020 and 4022 may be repositioned at an angle with respect to face 4236 of base 4230. Holes such as 4240 may be used to receive material during an insert molding process.

Figure 43:
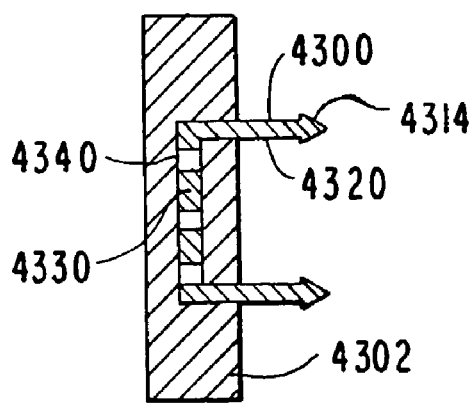
FIG. 43 is a sectional view of apparatus in accordance with the principles of the invention.

FIG. 43 shows anchor 4300 embedded in material 4302 that may be part of a band such as band 3902 shown in FIG. 39. Base 4330 may be molded into material 4302. Material 4302 may be present in holes such as 4340 in base 4330. One or more stems such as stem 4320 may protrude through material 4302 and support anchor head 4314 that may be used to engage biological tissue.

Figure 44:
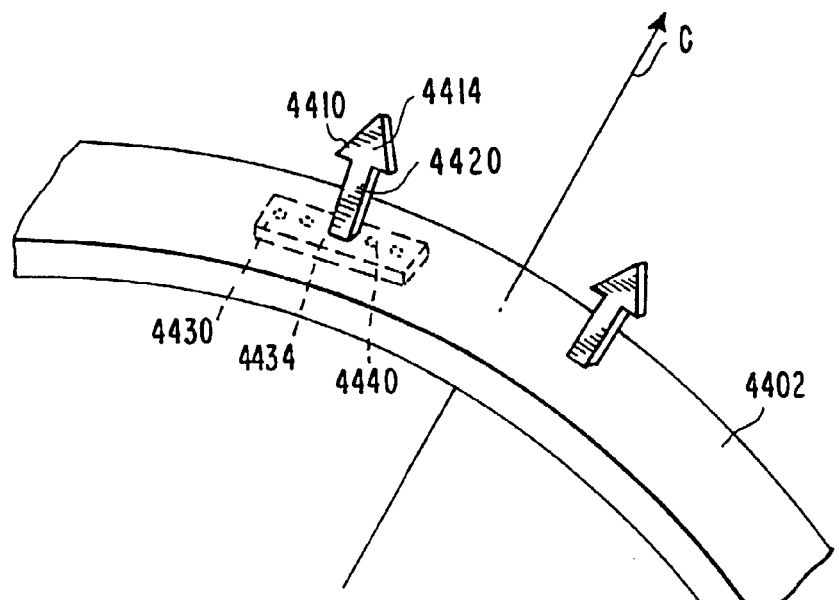
FIG. 44 is a perspective view of apparatus in accordance with the principles of the invention.

FIG. 44 shows illustrative anchor 4410 that may be used in conjunction with some embodiments of the invention. Anchor 4410 may be insert molded into a portion of band 4402 (shown in part). Anchor 4410 may include anchor head 4414 joined to stem 4420. Stem 4420 may extend away from central axis C of band 4402 in any suitable direction. In some embodiments, stem 4420 may be curved. Stem 4420 may be joined to base 4430 which may have one or more holes such as 4440 to receive material during a molding process. Stem 4420 may be joined to face 4434 of base 4430.

Figure 45:
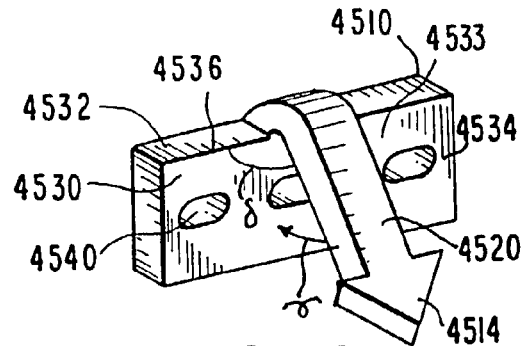
FIG. 45 is a perspective view of an apparatus in accordance with the principles of the invention.

FIG. 45 shows illustrative anchor 4510 that may be used in conjunction with some embodiments of the invention. Anchor 4510 may include stem 4520, which may extend from edge 4532 of base 4530. Stem 4520 may be positioned at angle γ with respect to face 4533 of base 4530. Angle γ may be any suitable angle. Stem 4520 may be positioned at angle δ with respect to edge 4536 of base 4530. Angle δ may be any suitable angle.

Figure 46:
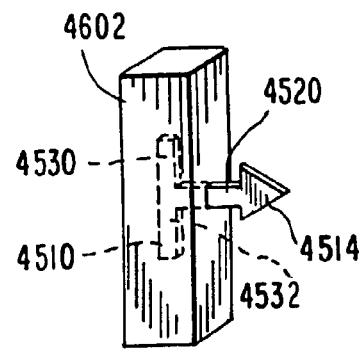
FIG. 46 is a perspective view of apparatus in accordance with the principles of the invention.
Figure 47:
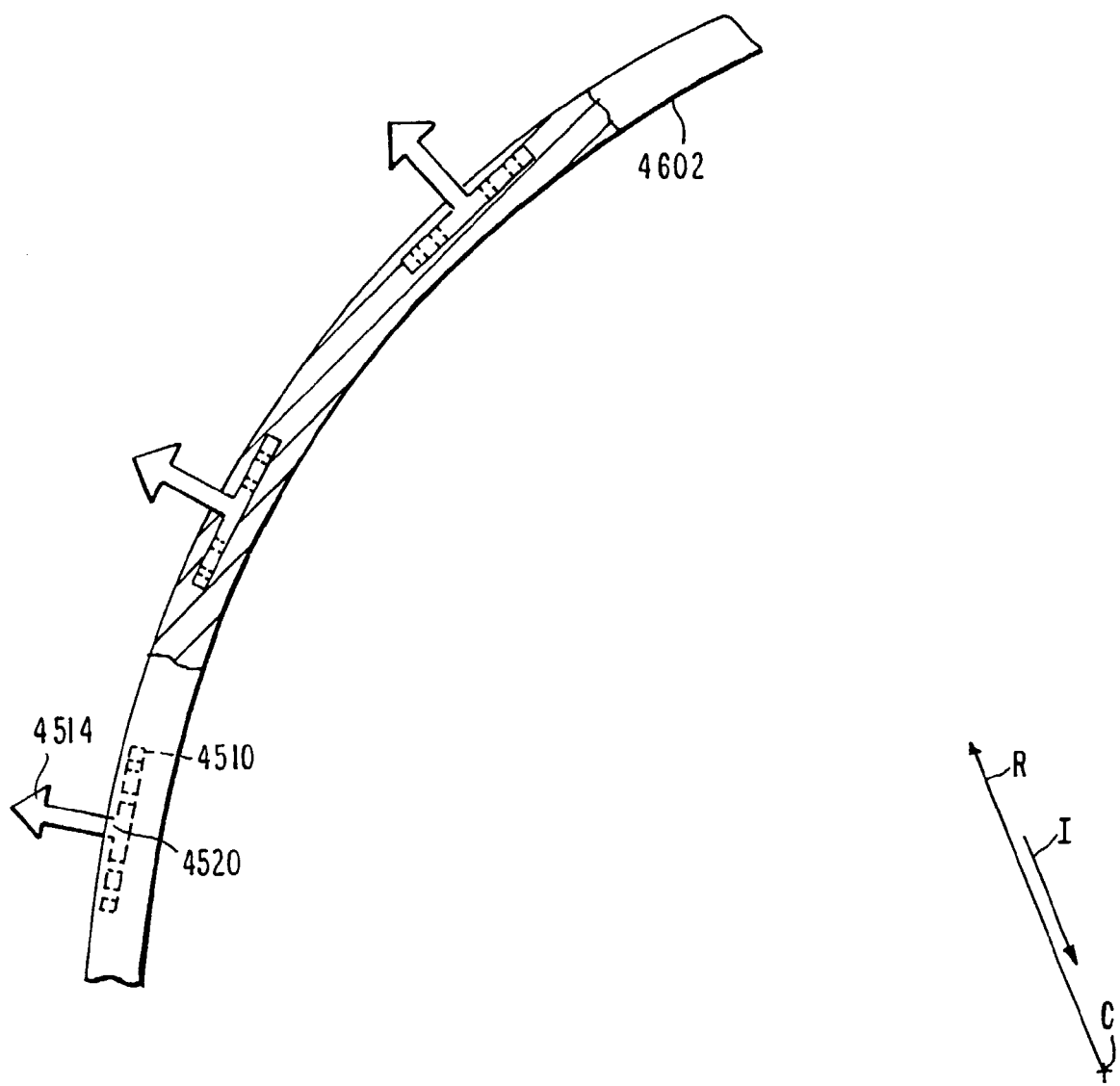
FIG. 47 is a top view of apparatus in accordance with the principles of the invention.

Base 4530 may have one or more holes such as hole 4540 for receiving material during a molding process. FIG. 46 shows anchor 4510 at least partially embedded in band 4602 (shown in part). Base 4530 may be encased in band 4602. Stem 4520 may extend from edge 4532 of base 4530 to anchor head 4514 outside band 4602. FIG. 47 shows a larger portion of band 4602 than that shown in FIG. 46. Band 4602 may house numerous anchors such as anchor 4510, each including one or more anchor heads such as 4514 joined to a stem such as stem 4520 extending away from central axis C in radial direction R. Band 4602 may expand away from axis C in direction R. Band 4602 may contract toward axis C in direction I.

Figure 48:
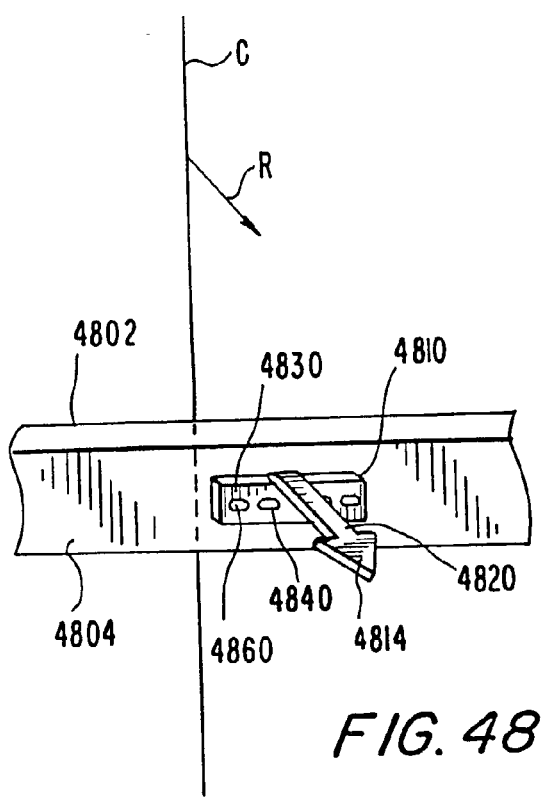
FIG. 48 is a perspective view of apparatus in accordance with the principles of the invention.

FIG. 48 shows illustrative anchor 4810 that may be used in conjunction with some embodiments of the invention. Anchor 4810 may include one or more stems such as stem 4820. Stem 4820 may be joined to anchor head 4814. Stem 4820 may be coupled to base 4830. Stem 4820 may extend radially away from central axis C. Stem 4820 may extend away from base 4830 in any suitable direction. Stem 4820 may curve away from base 4830 in any suitable direction or directions. Base 4830 may be coupled to radially outer face 4804 of band 4802 (shown in part). Holes such as hole 4840 may receive a boss or stud such as boss 4860 extending away from face 4804. Boss 4860 may be terminated in a knob to secure base 4830 to face 4804. Any suitable fastener may be used to fasten boss 4860 to base 4830.

Figure 49:
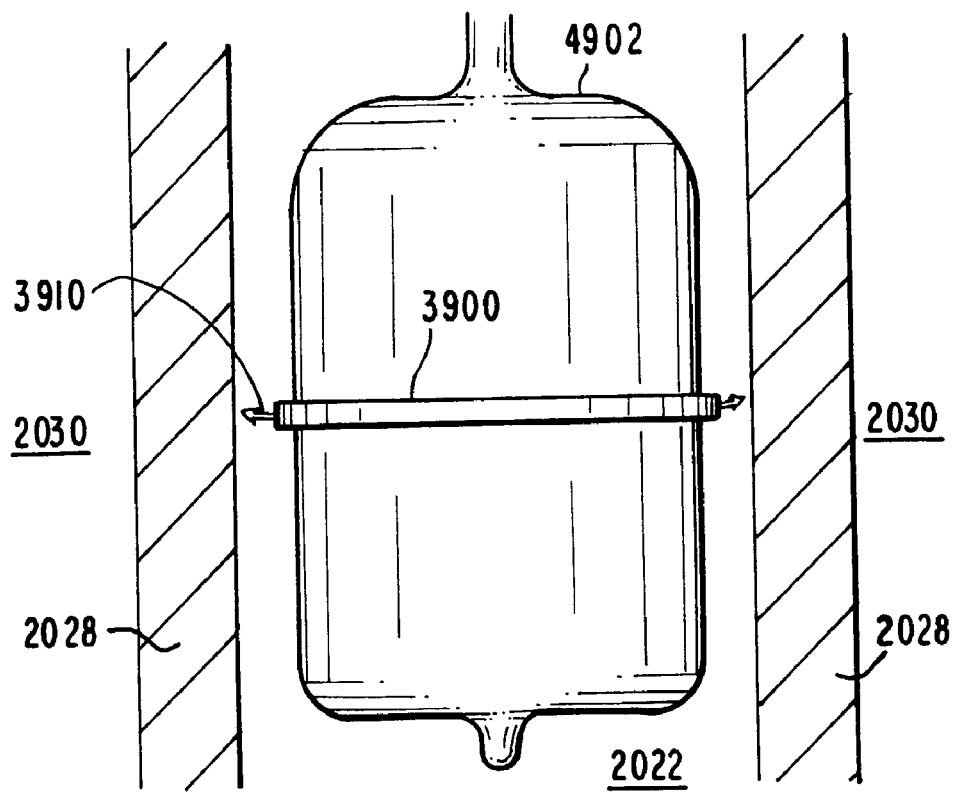
FIG. 49 is an elevational view of apparatus in accordance with the principles of the invention disposed in the biological passage shown in FIG. 20.

FIG. 49 shows apparatus 3900 (shown also in FIGS. 39ff) positioned in lumen 2022 of a biological passageway having walls 2028 using balloon 4902. Numerous anchors such as anchor 3910 may be present for engaging wall 2028. For the sake of clarity, only two anchors are shown.

Figure 50:
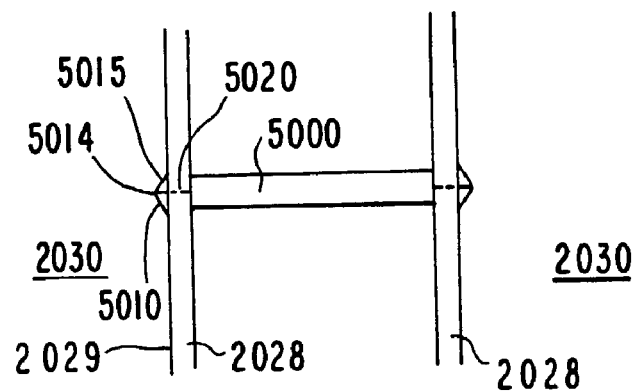
FIG. 50 is a partial elevational view of apparatus in accordance with the principles of the invention disposed in the biological passage shown in FIG. 20.

FIG. 50 shows apparatus 5000, which may be similar to apparatus 3900, in a stage of deployment later than that shown in FIG. 50 in connection with apparatus 3900. Apparatus 5000 may include one or more anchors such as anchor 5010. Anchor 5010 may include stem 5020 that may pass through wall 2028 into body cavity 2030. Anchor 5010 may include anchor head 5014. Anchor 5010 may include one or more barbs such as barb 5015. In some embodiments, barb 5015 may springingly rotate about an end joined to anchor head 5014. In some of those embodiments, barb 5015 may retract toward stem 5020 as head 5014 penetrates wall 2028. Barb 5015 may spring away from stem 5020 after a free end of barb 5015 clears outer surface 2029 of wall 2028. In some embodiments, apparatus 5000 may include any suitable anchor, including any of the anchors described herein.

Figure 51:
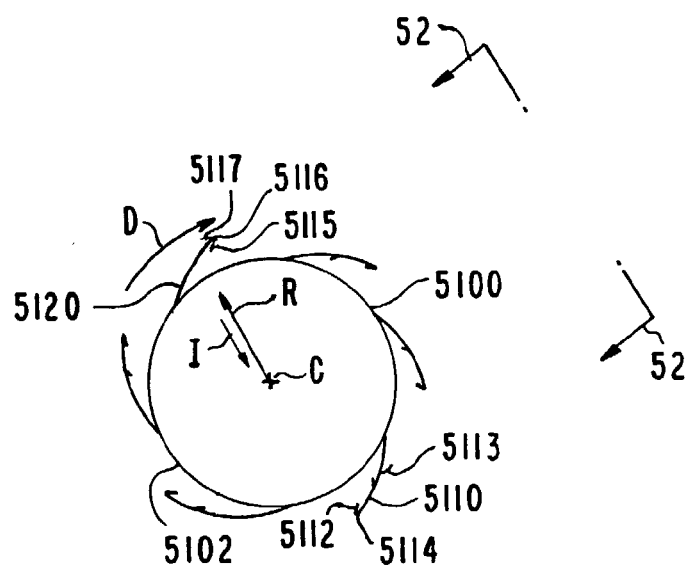
FIG. 51 is a schematic view of apparatus in accordance with the principles of the invention.

FIG. 51 shows apparatus 5100 that may be used to reduce the diameter of a portion of a biological passage. Band 5102 may be expandable away from central axis C in radial direction R to engage anchors such as anchor 5110 in the inner wall of the passage. Anchor 5110 may extend away from band 5102 in a direction generally the same as direction D.

Anchor 5510 may include one or more primary barbs such as primary barb 5112 extending from tip 5114 of anchor 5510. Anchor 5510 may include one or more secondary barbs such as secondary barb 5112 joined to anchor 5110 at a position away from tip 5114. A barb may extend from anchor 5110 in any direction. A barb may extend from a portion of anchor 5110 that faces generally toward band 5102 (as does barb 5112). A barb may extend from a portion of anchor 5110 that faces generally away from band 5102 (as does barb 5113). An anchor may include barbs facing in more than one direction. Anchor 5120 is an illustrative example of an anchor that includes two primary barbs, 5115 and 5117, joined to barb tip 5116.

Apparatus 5100 may be rotated in direction D to cause anchor 5110 to penetrate into the wall. Apparatus 5100 may be rotated in the direction opposite D to engage a barb in the wall tissue. A barb or barbs may help secure apparatus 5100 to the inner wall of the biological passage. After band 5102 is expanded to engage anchors in the inner wall, band 5102 may automatically contract toward axis C and may draw the inner wall inward in direction I. The diameter of the biological passage may be reduced.

Figure 52:
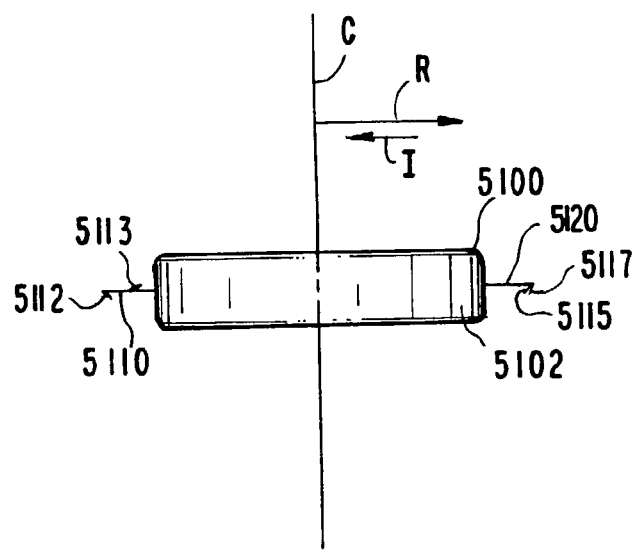
FIG. 52 is an elevational view taken from line 52—52 of FIG. 51.

FIG. 52 shows anchors 5110 and 5120 extending away from band 5102. (Some of the anchors shown in FIG. 51 are not shown in FIG. 52 for the sake of clarity.) FIG. 52 shows that in some embodiments, one or more of barbs 5112, 5113, 5115, and 5117 may extend away from a plane defined by band 5102. In some embodiments, one or more barbs may be contained in an axial plane of apparatus 5100.

Figure 53:
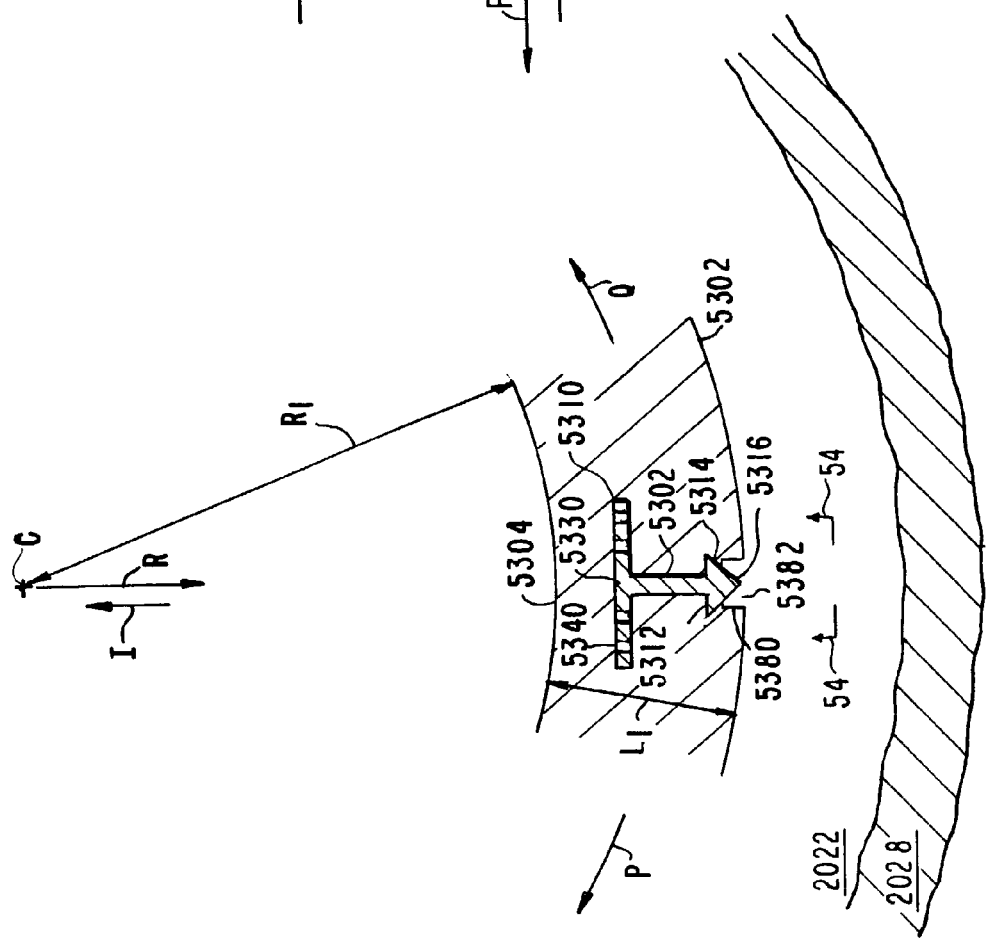
FIG. 53 is a sectional view of apparatus in accordance with the principles of the invention disposed in the biological passage shown in FIG. 20.

FIGS. 53–56 illustrate a feature of some embodiments of the invention in which at least a portion of an anchor may be projected through an aperture in a band to engage tissue of a biological passage wall. The anchor portion may then be retracted back toward the band to secure the tissue. FIG. 53 shows a portion of band 5302 in a neutral state positioned in lumen 2022 near biological passage wall 2028. Radially inner edge of band 5302 may be at a distance R1 from central axis C. Band 5302 may have neutral state radial thickness $L_1$. Anchor 5310 may be coupled to band 5302. Anchor 5310 may be insert molded into band 5302. Anchor 5310 may have one or more holes such as hole 5340 in base 5330 to receive material during a molding process. Stem 5320 may extend away from base 5330 in radial direction R. Recess 5380, which may include aperture 5382 may be present in band 5302 near anchor head 5314. In some embodiments, in the neutral state a portion of head 5314, which may include tip 5316, may be present in recess 5380. In some embodiments, in the neutral state recess 5380 may extend in circumferential directions P and Q no farther than does trailing edge 5312 of head 5314. In an expanded state, recess 5380 may expand in directions P and Q to allow head 5314 to project out of band 5302 as the thickness of band 5302 is reduced.

Figure 54:
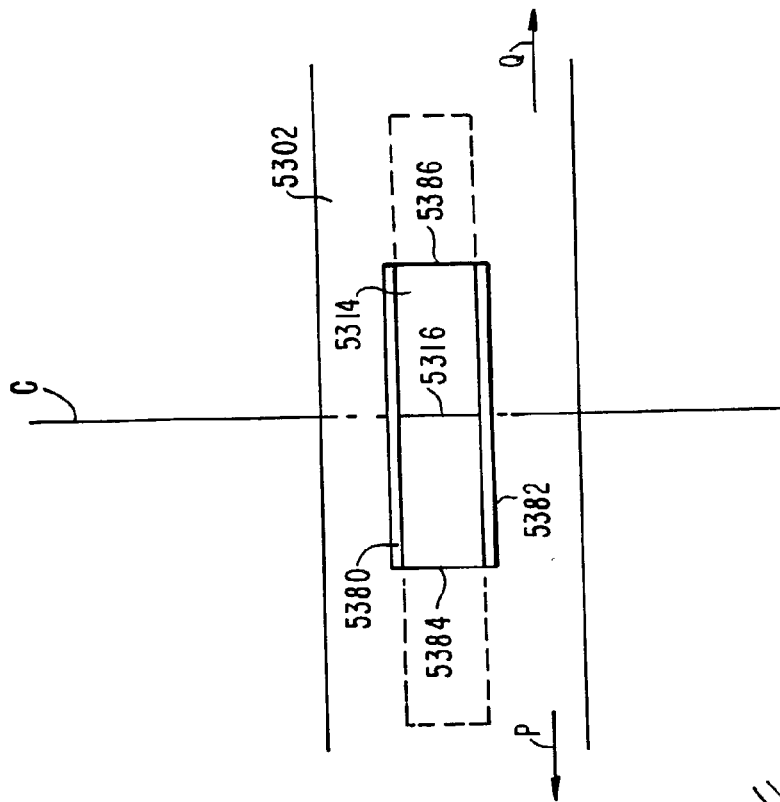
FIG. 54 is an elevational view taken from line 54—54 of FIG. 53.

FIG. 54 shows recess 5380 in band 5302. Head 5314, including tip 5316, is partially exposed through aperture 5382. Portions of head 5314 that are not exposed through aperture 5382 are shown using broken lines. When band 5302 is expanded radially away from axis C, edges 5384 and 5386 of aperture 5382 may be pulled away from tip 5316 in directions P and Q, respectfully, to allow head 5314 to emerge from band 5302.

Although anchor 5310 is illustrated as a "flat" anchor such as anchor 4410 shown in FIG. 44, some embodiments of the invention in which an anchor may project through a band aperture may include one or more anchors of different types, including one or more the anchors described herein. The shapes and sizes of recess 5380 and aperture 5382 may be chosen to allow an anchor to emerge from band 5302. The shapes and sizes of recess 5380 and aperture 5382 may be chosen to allow an anchor stem to at least partially retract back into band 5302.

Figure 55:
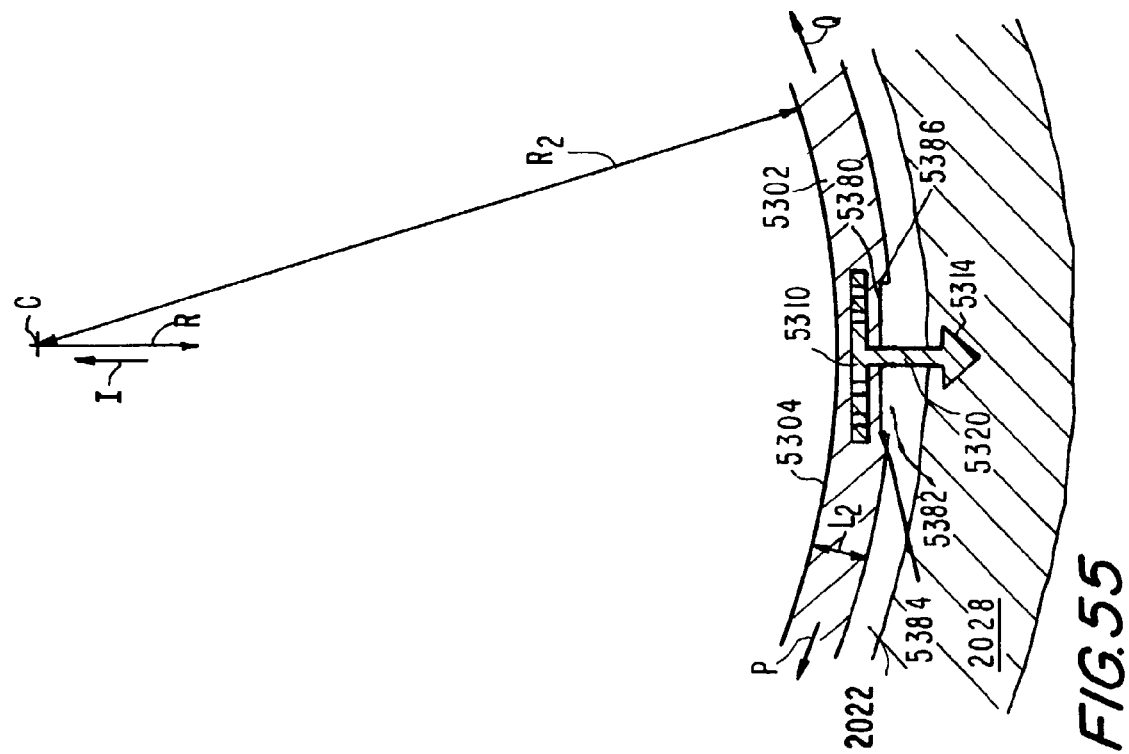
FIG. 55 is a sectional view of apparatus in accordance with the principles of the invention disposed in the biological passage shown in FIG. 20.

FIG. 55 shows band 5302 in an expanded state. Inner radial edge 5304 is positioned at distance $R_2$, which may be greater than distance $R_1$ (shown in FIG. 53), from central axis C. The radial thickness of band 5302 in the expanded state is $L_2$, which may be less than thickness $L_1$, (shown in FIG. 53). Recess 5380 in the expanded state may have increased (relative to the neutral state) in circumferential directions P and Q (edge 5384 in direction P and edge 5386 in direction Q, e.g.) and may have decreased in radial thickness. Anchor 5310, which may include material that is more rigid than band 5302 may not be deformed as much as band 5302 during the expansion of band 5302. Stem 5320 may project out of recess 5380 through aperture 5382. Head 5314 may engage tissue of wall 2028.

Figure 56:
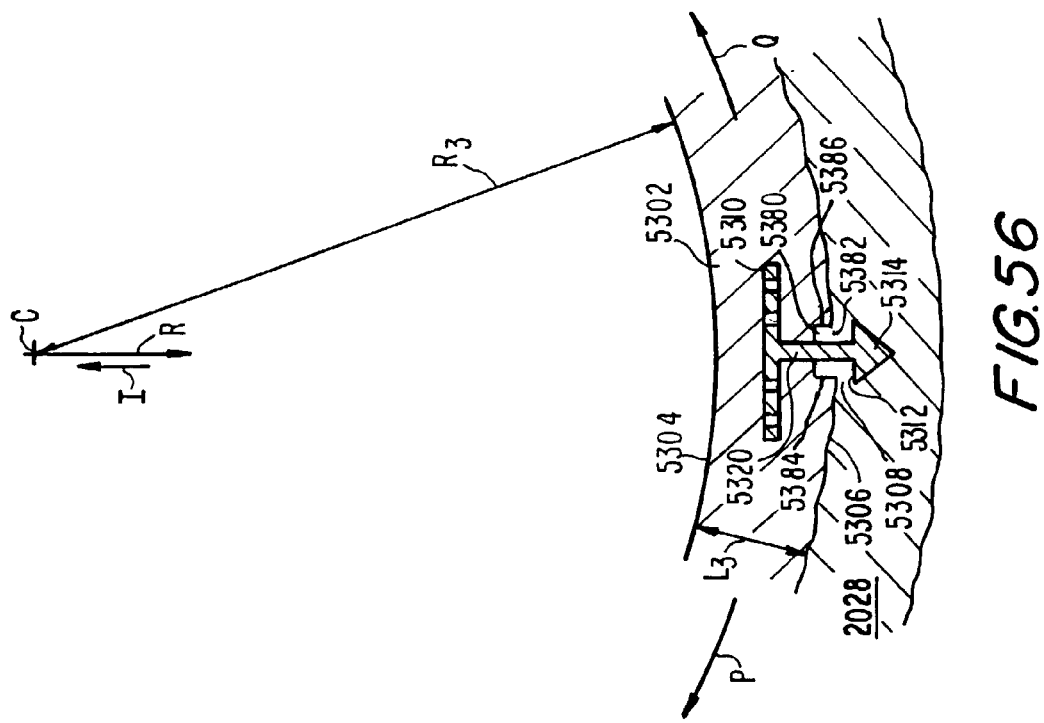
FIG. 56 is a sectional view of apparatus in accordance with the principles of the invention disposed in the biological passage shown in FIG. 20.

FIG. 56 shows band 5302 in a retracted state. In the retracted state, band 5302 may not be fully retracted to the neutral state shown in FIG. 53 because outward radial forces from wall 2028 may act on band 5302 after anchor 5310 engages tissue of wall 2028. In the retracted state, inner radial edge 5304 of band 5302 may be positioned at distance $R_3$ from central axis C. $R_3$ may be greater than $R_1$ (shown in FIG. 53). $R_3$ may be less than $R_2$ (shown in FIG. 55). In the retracted state, band 5302 may have radial thickness $L_3$. $L_3$ may be less than $L_1$ (shown in FIG. 35). $L_3$ may be greater than $L_2$ (shown in FIG. 55). Stem 5320 may have partially retracted behind outer radial edge 5306 of band 5302 drawing edge 5312 of head 5314 toward outer radial edge 5306 and trapping or pinching tissue of wall 2028 in area 5308. Aperture 5382 may have contracted toward stem 5320. (Edges 5384 and 5386 of recess 5380 may have migrated in directions Q and P, respectively, during retraction of band 5302.) Wall 2028 may be closer to central axis C when band 5302 is secured to wall 2028 and is retracted than before anchor 5310 engaged wall 2028 (as shown in FIG. 53, for example).

Figure 57:
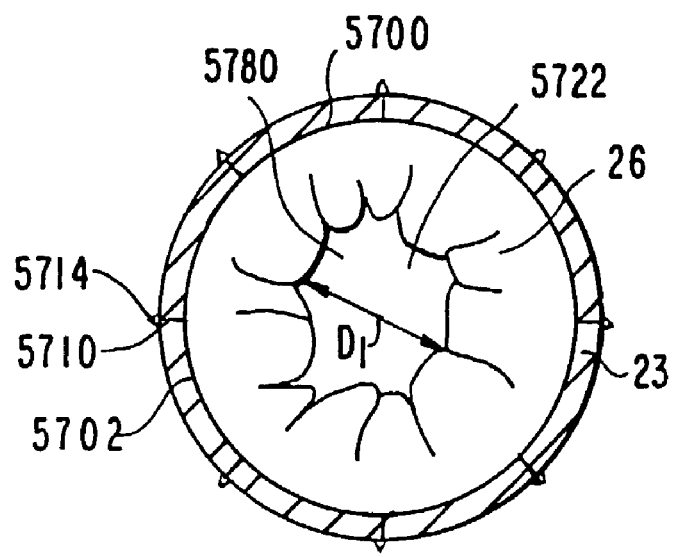
FIG. 57 is a schematic view of apparatus in accordance with the principles of the invention disposed in the biological passage shown in FIG. 2.
Figure 58:
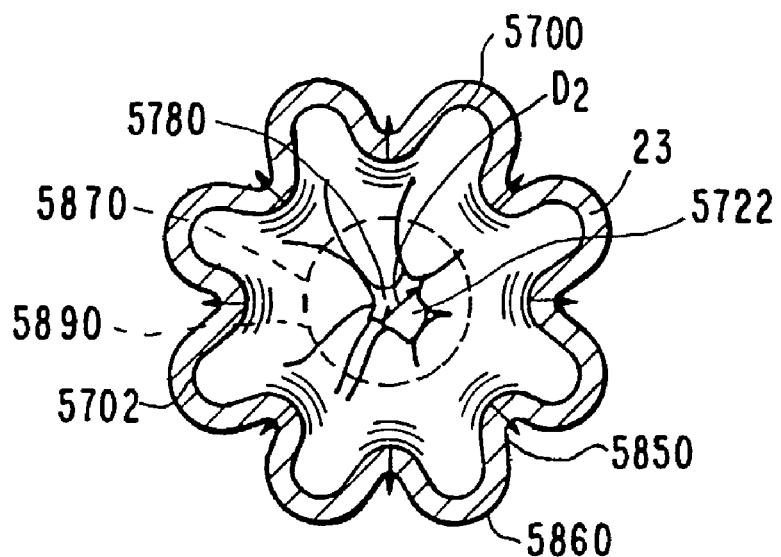
FIG. 58 is a schematic view of apparatus in accordance with the principles of the invention disposed in the biological passage shown in FIG. 2.

FIGS. 57–58 show apparatus 5700 positioned in distal esophagus 23 above LES 26. Apparatus 5700, which may include band 5702 and one or more anchors such as anchor 5710, may have any suitable features for engaging distal esophagus 23 and reducing the diameter of distal esophagus 23, LES 26, or both. Apparatus 5700 may include one or more of the bands, anchors, and other apparatus described herein.

FIG. 57 shows band 5702 in an expanded state. Anchor heads such as head 5714 may extend away from central region 5722 of apparatus 5700. Head 5714 may extend all the way through the wall of distal esophagus 23. Opening 5780 of relaxed LES 26 has approximate diameter $D_1$.

FIG. 58 shows band 5702 in a retracted state. Portions of distal esophagus 23, such as portion 5850, may be drawn toward central region 5722 of apparatus 5700. Some portions of distal esophagus 23, such as portion 5860, may not be drawn toward central region 5722. Some portions of distal esophagus 23, such as portion 5860, may be drawn toward central region 5722, but not to the extent that portions such as 5850 are drawn toward region 5722. When band 5702 is in the retracted state, opening 5780 of relaxed LES 26 may be reduced. When band 5702 is retracted, opening 5780 may have approximate diameter $D_2$, which may be less than approximate diameter $D_1$ (shown in FIG. 57.) Broken line 5870 shows the approximate size of opening 5780 when band 5702 is in the expanded state (as shown in FIG. 57).

Figure 59:
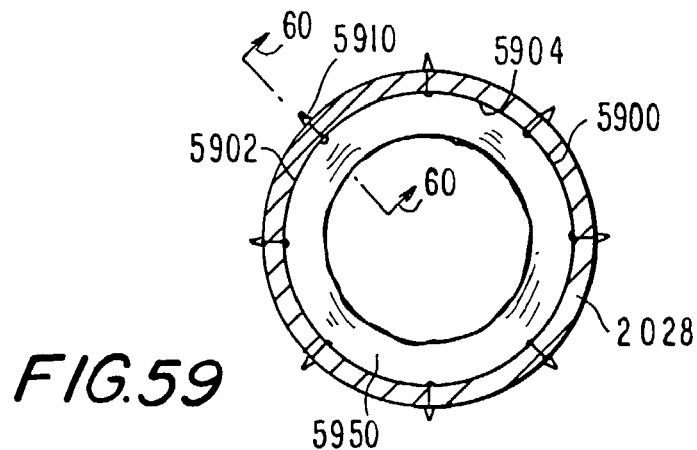
FIG. 59 is a partial sectional view of apparatus in accordance with the principles of the invention disposed in the biological passage shown in FIG. 20.
Figure 60:
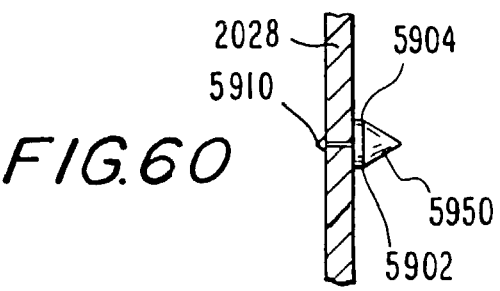
FIG. 60 is a sectional view taken from line 60—60 in FIG. 59.
Figure 61:
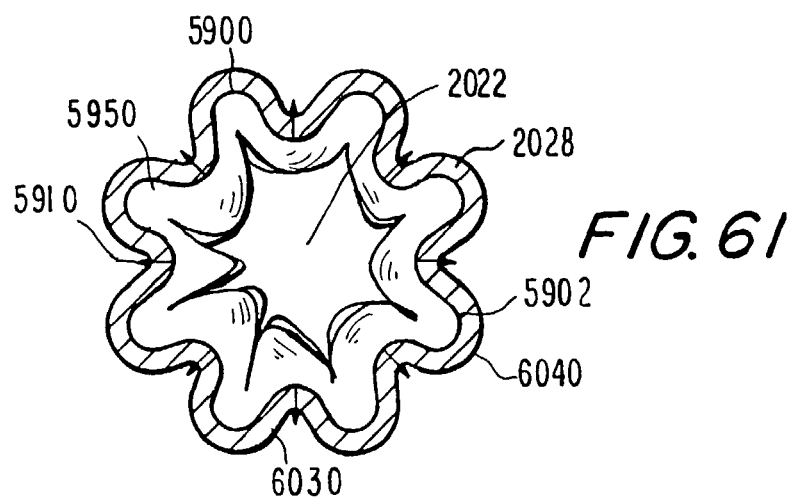
FIG. 61 is a partial sectional view of apparatus in accordance with the principles of the invention disposed in the biological passage shown in FIG. 20.

FIGS. 59–61 show features of some embodiments of the invention that may include a deposit of substance on an apparatus that may be used to reduce the diameter of a biological passage. The substance may have a therapeutic effect on the biological passage. The substance may help seal the apparatus to the passage. In some embodiments, the substance may be a foam. In some embodiments, the substance may be a gel. In some embodiments, the substance may include a drug. In some embodiments, the substance may include an adhesive.

FIG. 59 shows apparatus 5900 positioned in biological passage having wall 2028. Apparatus 5900 may include band 5902 and one or more anchors such as 5910. Apparatus 5900 may have any suitable features for engaging wall 2028. Apparatus 5900 may have any suitable features for reducing the diameter of the biological passage. Apparatus 5900 may include one or more of the bands, anchors, and other apparatus described herein.

FIG. 59 shows band 5902 in an expanded state. Anchors such as anchor 5910 may extend through wall 2028. Substance 5950 may be present on band 5902. In some embodiments, substance 5950 may be disposed on inner surface 5904 of band 5902. In some embodiments, substance 5950 may be present in pores that may be present in band 5902. In some embodiments, substance 5950 may be present in pores that may be present in one or more anchors such as anchor 5910. Substance 5950 present in pores or on the surface of apparatus 5900 may elute from the apparatus. In some embodiments, substance 5950 may be soluble. In some embodiments, substance 5950 may gradually migrate to portions of the passage including wall 2028.

FIG. 60 shows substance 5950 disposed on inner surface 5904 of band 5902 near anchor 5910 protruding through wall 2028.

FIG. 61 shows band 5902 in a retracted state. Portions of wall 2028 such as portion 6030 may be drawn toward the central region of lumen 2022 of the biological passage. Portions of wall 2028 such as portion 6040 may be drawn toward the central region of lumen 2022, but may not be drawn as far as portions such as portion 6030. Some portions of wall 2028 may not be drawn toward the central region of lumen 2022. Substance 5950 may be squeezed toward central region of lumen 2022. Substance 5950 may be deposited on portions of wall 2028 by apparatus 5900.

Figure 62:
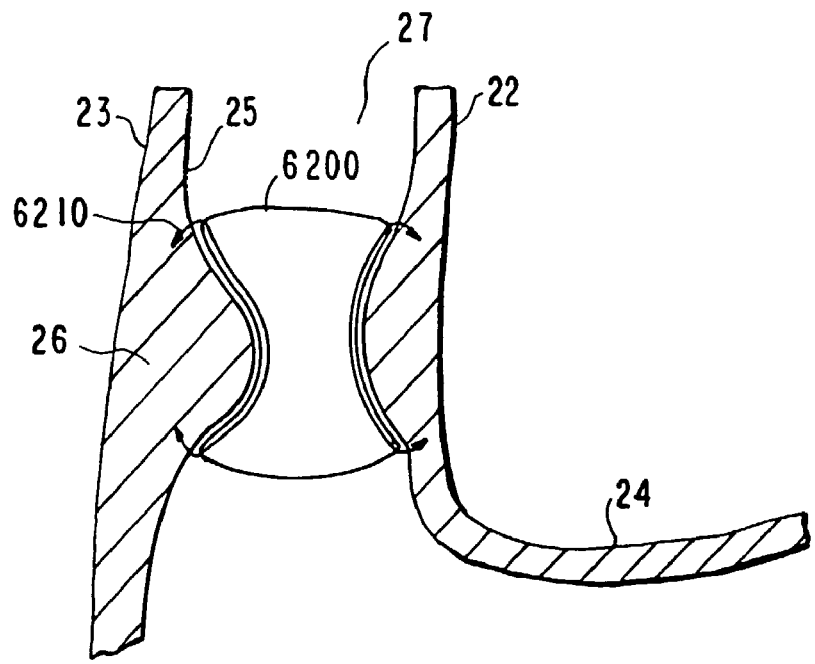
FIG. 62 is a partial elevational view of apparatus in accordance with the principles of the invention disposed in the biological passage shown in FIG. 2.

FIGS. 62–65 show illustrative examples of features that may be present in some embodiments of the invention that may be used to line a portion of a biological passage. FIG. 62 shows liner 6200 that may be disposed in lumen 27 of esophagus 22 adjacent LES 26. (In some embodiments of the invention, liner 6200 may be prophylactically disposed in a healthy esophagus.) Liner 6200 may include inert material for protecting tissue of LES 26 from irritation, degradation, or any other effects of chemicals or biological materials that may be present in esophagus 22. Liner 6200 may include flexible material. Liner 6200 may include elastic material. In some embodiments of the invention, liner 6200 may be secured to wall 25 of esophagus 22 by anchors such as anchor 6210.

In some embodiments, liner 6200 may be held in place by one or more balloon-expandable frames. In some of those embodiments, the frame or frames may be plastically deformed. The frame or frames may retain a shape established by the balloon when the balloon is dilated.

In some embodiments, liner 6200 may be held in place by a self-expanding frame (not shown). In some of those embodiments, the frame may include elastic material. The frame may be compressed for insertion in esophagus 22 and may expand in lumen 27 sufficiently to conform to wall 25. In some embodiments, liner 6200 may not include an anchor. In some embodiments, liner 6200 may be held in place using any suitable structure or structures, including any band or bands, anchor or anchors, or any combination thereof described herein. In some embodiments, liner 6200 may be deployed using any suitable device or devices, including any suitable device or device described herein.

Figure 63:
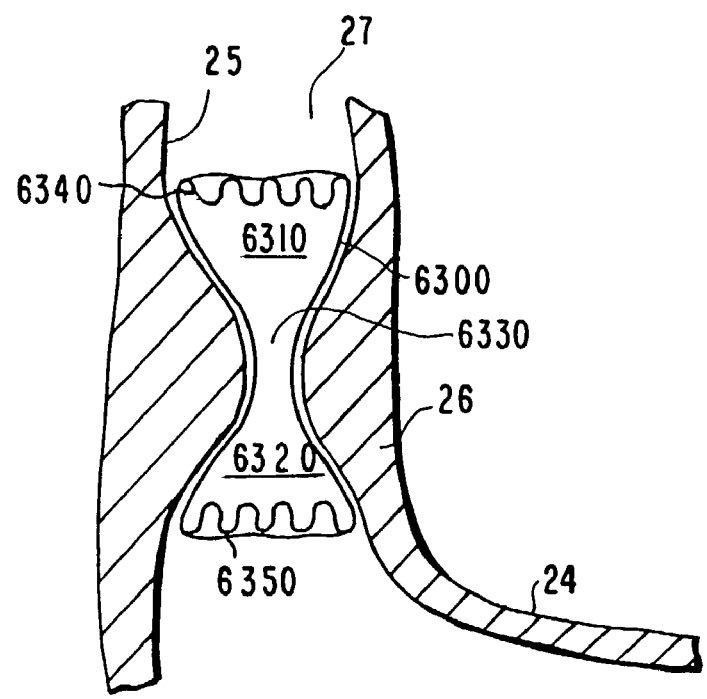
FIG. 63 is a schematic view of apparatus in accordance with the principles of the invention disposed in the biological passage shown in FIG. 2.

FIG. 63 shows liner 6300 positioned adjacent LES 26. Liner 6300 may include end portion 6310. Liner 6300 may include end portion 6320. Liner 6300 may include medial portion 6330. Medial portion 6330 may be positioned at the narrowest constriction of lumen 27.

Frame 6340 may be present near end portion 6310 to conform end portion 6310 to wall 25. Frame 6350 may be present near end portion 6320 to conform end portion 6320 to wall 25. Medial portion 6330 may not have a corresponding frame to allow medial portion 6330 to closely contour wall 25. In some embodiments, a frame may be present near medial portion 6330 to secure medial portion 6330 to wall 25. Frames may be positioned internal to liner 6300 or external to liner 6300. In some embodiments numerous frames may be present to conform liner 6300 to wall 25. In some embodiments, liner 6300 may be held in place using any suitable structure or structures, including any band or bands, anchor or anchors, or any combination thereof described herein. In some embodiments, liner 6300 may be deployed using any suitable device or devices, including any suitable device or device described herein.

Figure 64:
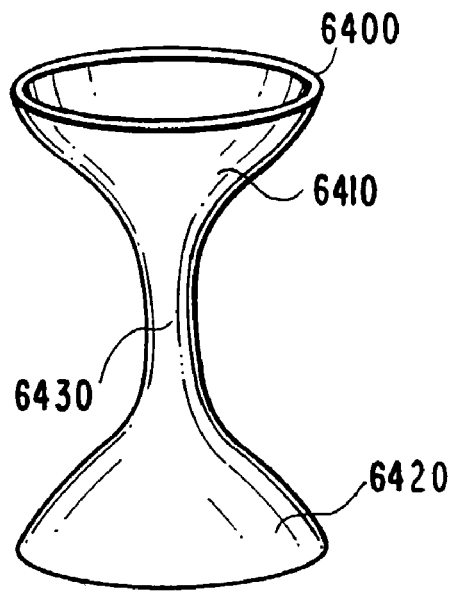
FIG. 64 is a perspective view of an apparatus in accordance with the principles of the invention.

FIG. 64 shows illustrative pre-shaped liner 6400. Pre-shaped liner 6400 may be shaped outside of a biological passage and inserted into the passage. In some embodiments, liner 6400 may be shaped in accordance with a known profile of the biological passage in which line 6400 will be deployed. Liner 6400 may be shaped in accordance with passage profile data that may be collected from the passage (for example, by direct measurement or by medical imaging). Liner 6400 may include any suitable inert material that is formable. In some embodiments, liner 6400 may include a thermoplastic material. In some embodiments, line 6400 may be molded. In some embodiments, liner 6400 may be held in place using any suitable structure or structures, including any band or bands, anchor or anchors, or any combination thereof described herein.

Figure 65:
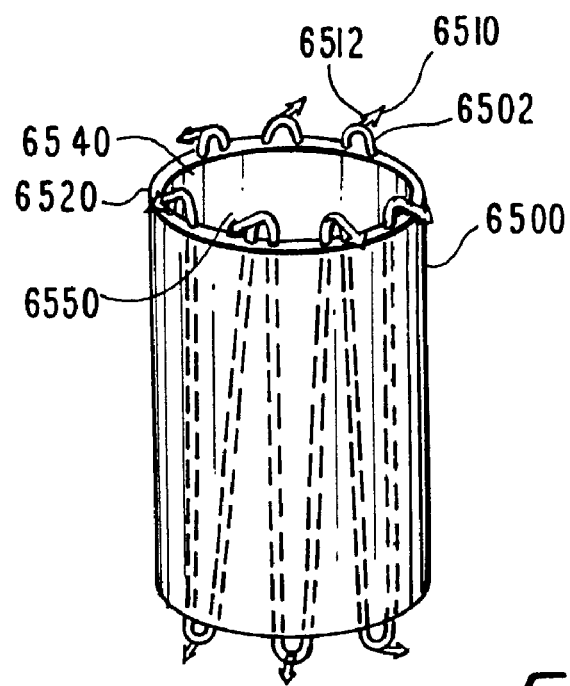
FIG. 65 is a perspective view of apparatus in accordance with the principles of the invention.

FIG. 65 shows apparatus 6500 that may include liner 6520, which may include inert material. Apparatus 6500 may include inner liner 6540, which may include inert material. Apparatus 6500 may be positioned in the lumen of a biological passage to protect a portion of the passage from harmful materials. In some embodiments, apparatus 6500 may include frame 6502. Frame 6502 may be positioned between inner liner 6540 and outer liner 6520. Anchors such as anchor 6510, which may include barb 6512, may be present on frame 6502 to attach apparatus 6500 to the biological passage wall. Anchor 6510 may include inert material. Some embodiments may not include an anchor.

Frame 6502 may include inert material. In some embodiments, frame 6502 may be self-expanding. In those embodiments, frame 6502 may include elastic material that can be compressed to insert frame 6502 in a biological passage. After positioning frame 6502 in the passage, frame 6502 may expand to cause liner 6520 to contact the passage wall. In some embodiments, frame 6502 may include ductile or plastically deforming material. In those embodiments, frame 6502 may be inserted in a state in which frame 6502 is of smaller diameter than the passage. Frame 6502 may then be expanded by dilating a balloon in bore 6550. After expansion, frame 6502 may remain in an expanded state.

In some embodiments, apparatus 6500 may be held in place using any suitable structure or structures, including any band or bands, anchor or anchors, or any combination thereof described herein. In some embodiments, apparatus 6500 may be deployed using any suitable device or devices, including any suitable device or device described herein.

Figure 66:
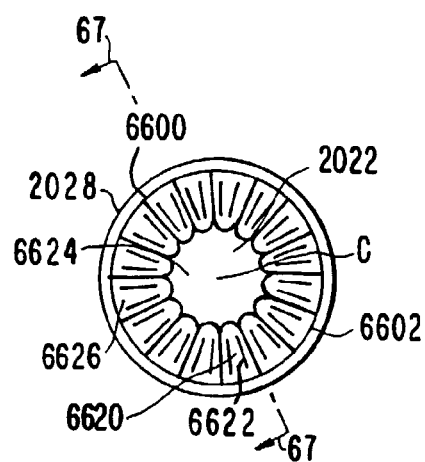
FIG. 66 is a partial top view of apparatus in accordance with the principles of the invention disposed in the biological passage shown in FIG. 20.

FIGS. 66–69 show illustrative examples of features that may be present in some embodiments of the invention and that may regulate the flow of matter through a biological passage. In some embodiments, these features may promote chemical or biochemical reactions. FIG. 66 shows apparatus 6600 that may be deployed in a biological passage having lumen 2022 and wall 2028. Wall 2028 and lumen 2022 are shown in sectional view.

Apparatus 6600 may include band 6602 that may be secured against wall 2028. One or more fingers such as finger 6620 may extend from band 6602 into lumen 2022. Finger 6620 may be flexible. In some embodiments, finger 6620 may include one or more fibers. In some embodiments, finger 6620 may include one or more surface area enhancing features such as feature 6622.

Feature 6622 may be a fold, a pleat, a groove, a bend, a projection, a protuberance, or any other suitable type of surface area feature. In some embodiments, finger 6620 may include more than one type of surface area enhancing feature. In some embodiments, apparatus 6600 may include more than one type of finger. In some embodiments, fingers may be closely spaced with respect to each other. In some embodiments, space may be present between fingers.

In some embodiments, one or more fingers may extend to central region 6624 of apparatus 6600. In some embodiments, one or more fingers may extend only into marginal region 6626 of apparatus 6600. In some embodiments, apparatus 6600 may include short fingers and long fingers. In some embodiments, apparatus 6600 may include fingers that are curved. In some of those embodiments, the fingers may curve in the distal direction, in the proximal direction, or in a direction that is non-radial (with respect to axis C).

In some embodiments, apparatus 6600 may be held in place using any suitable structure or structures, including any band or bands, anchor or anchors, or any combination thereof described herein. In some embodiments, apparatus 6600 may be deployed using any suitable device or devices, including any suitable device or device described herein.

Figure 67:
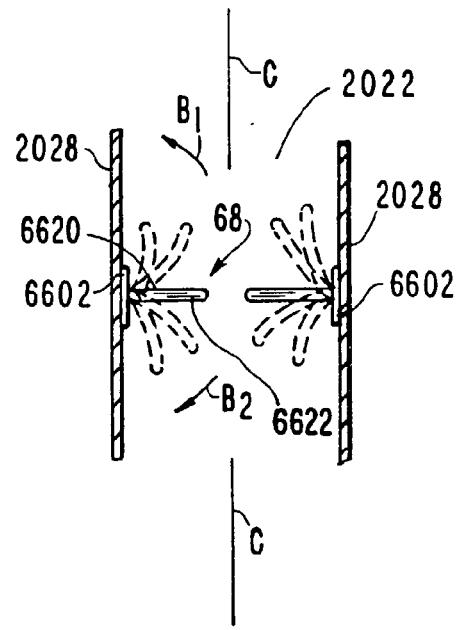
FIG. 67 is a partial elevational view taken from line 67—67 in FIG. 66.

FIG. 67 shows finger 6620 and a finger opposite finger 6620 on band 6602. In some embodiments, finger 6620 may bend from the rest position shown (approximately perpendicular to wall 2028) in direction $B_1$. In some embodiments, finger 6620 may bend in direction $B_2$. Broken lines show different positions that may be occupied by finger 6620 and the opposite finger as the fingers flex. The flexibility of finger 6620 may be preselected to regulate the amount of flex that will occur in response to a given force. In some embodiments, finger 6620 may have a rest position that is at an angle to wall 2028. In some of those embodiments, numerous fingers may have a rest position that is at an angle to wall 2028 to provide a directional bias to material that may flow through lumen 2022.

Figure 68:
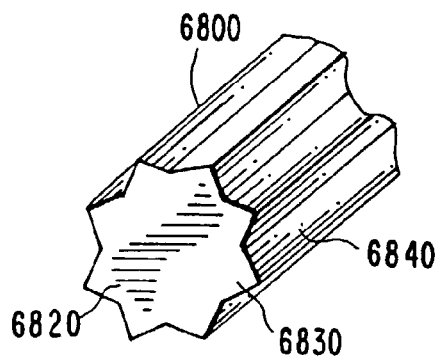
FIG. 68 is a perspective view of an apparatus in accordance with the principles of the invention.

FIG. 68 shows finger 6800 that may be included in an apparatus such as 6600. Finger 6800 may have tip 6820 which may project into lumen 2022. In some embodiments, finger 6800 may taper to a narrow terminus or cone that may project into lumen 2022. Finger 6800 may include one or more secondary members such as member 6830. In some embodiments, member 6830 may extend away from finger 6800 to a greater extent than that shown in FIG. 68. Member 6830 may include one or more surfaces such as surface 6840.

FIG. 69 shows finger 6900 that may be included in an apparatus such as 6600. Finger 6900 may have tip 6920 which may project toward lumen 2022. In some embodiments, finger 6900 may taper to a narrow terminus or cone that may project into lumen 2022. Finger 6900 may include one or more secondary members such as member 6930. In some embodiments, member 6930 may extend away from finger 6900 to a greater extent than that shown in FIG. 69. Member 6930 may include one or more surfaces such as surface 6940.

It will be appreciated by one skilled in the art that any feature illustrated with or without a reference numeral in any of the FIGS. herein, including, but not limited to, any anchor, portion of an anchor, band, portion of a band, liner, portion of a liner, finger, and/or portion of a finger, if present in an embodiment of the invention, may include any suitable attribute or suitable combination of attributes shown (with or without a reference numeral) or described in connection with any of the embodiments herein.

Thus it is seen that improved apparatus and methods for reducing the diameter of a portion of a biological passage have been provided. Apparatus and methods for lining a portion of a biological passage have been provided. Apparatus and methods deploying a baffle in a portion of a biological passage have been provided. One skilled in the art will appreciate that the present invention can be practiced by other than the described embodiments, which are presented for purposes of illustration and not of limitation, and the present invention is limited only by the claims which follow.

What is claimed is:

1. An apparatus for reducing the diameter of a portion of a biological passage, said passage having a wall, said apparatus comprising:
    a polymeric body having a bore, said bore defining a central axis, at least a portion of said body configured to move from a first position to a second position, said second position at a greater distance from said axis than said first position, said portion having an outer peripheral surface; and
    a metal anchor coupled to said portion, said anchor having a tip;
wherein:
    said tip moves away from said outer peripheral surface when said portion moves from said first to said second position; and
    said anchor is configured to pull said wall toward said axis when said portion moves from said second position toward said first position.

2. An apparatus for reducing the diameter of a portion of a biological passage, said passage having a wall and a central axis said apparatus comprising:
    at least one first portion having a first elasticity;
    at least one second portion coupled to said first portion, said second portion having a second elasticity; and
    at least one anchor coupled to said first portion, said anchor configured to pull said wall toward said axis;
    wherein said first elasticity is less than said second elasticity.

3. The apparatus of claim 2 wherein said first and second portions are included in a lobed strip.

4. The apparatus of claim 3 wherein said strip has a sinusoidal form.

5. The apparatus of claim 3 wherein said strip forms a closed loop.

6. An apparatus for reducing the diameter of a portion of a biological passage, said passage having a wall and a central axis said apparatus comprising:
    at least one first portion having a first elasticity;
    at least one second portion coupled to said first portion, said second portion having a second elasticity; and
    at least one anchor coupled to said first portion, said anchor configured to pull said wall toward said axis;
wherein:
    said second elasticity is more than about 10% greater than said first elasticity.

* * * * *